(12) United States Patent
Phipps et al.

(10) Patent No.: US 10,548,911 B2
(45) Date of Patent: Feb. 4, 2020

(54) SMALL MOLECULE ANTI-SCARRING AGENTS

(71) Applicant: UNIVERSITY OF ROCHESTER, Rochester, NY (US)

(72) Inventors: Richard P. Phipps, Pittsford, NY (US); Collynn Woeller, Webster, NY (US)

(73) Assignee: University of Rochester, Rochester, NY (US)

( * ) Notice: Subject to any disclaimer, the term of this patent is extended or adjusted under 35 U.S.C. 154(b) by 47 days.

(21) Appl. No.: 15/319,254

(22) PCT Filed: Jun. 16, 2015

(86) PCT No.: PCT/US2015/036059
§ 371 (c)(1),
(2) Date: Dec. 15, 2016

(87) PCT Pub. No.: WO2015/195684
PCT Pub. Date: Dec. 23, 2015

(65) Prior Publication Data
US 2017/0216332 A1 Aug. 3, 2017

Related U.S. Application Data

(60) Provisional application No. 62/114,932, filed on Feb. 11, 2015, provisional application No. 62/201,602, filed on Jun. 16, 2014.

(51) Int. Cl.
| | |
|---|---|
| *A61K 31/7048* | (2006.01) |
| *A61K 45/06* | (2006.01) |
| *A61K 31/167* | (2006.01) |
| *A61K 31/351* | (2006.01) |
| *A61K 31/166* | (2006.01) |
| *A61K 31/341* | (2006.01) |
| *A61K 31/381* | (2006.01) |
| *A61K 31/415* | (2006.01) |
| *A61K 31/4184* | (2006.01) |
| *A61K 31/4409* | (2006.01) |
| *A61K 31/4412* | (2006.01) |
| *A61K 31/47* | (2006.01) |
| *A61K 31/519* | (2006.01) |
| *A61K 31/5375* | (2006.01) |
| *A61K 31/549* | (2006.01) |
| *A61K 31/551* | (2006.01) |
| *A61K 31/635* | (2006.01) |

(52) U.S. Cl.
CPC ........ *A61K 31/7048* (2013.01); *A61K 31/166* (2013.01); *A61K 31/167* (2013.01); *A61K 31/341* (2013.01); *A61K 31/351* (2013.01); *A61K 31/381* (2013.01); *A61K 31/415* (2013.01); *A61K 31/4184* (2013.01); *A61K 31/4409* (2013.01); *A61K 31/4412* (2013.01); *A61K 31/47* (2013.01); *A61K 31/519* (2013.01); *A61K 31/5375* (2013.01); *A61K 31/549* (2013.01); *A61K 31/551* (2013.01); *A61K 31/635* (2013.01); *A61K 45/06* (2013.01)

(58) Field of Classification Search
None
See application file for complete search history.

(56) References Cited

U.S. PATENT DOCUMENTS

| | | |
|---|---|---|
| 2,353,735 A | 7/1944 | Kunz et al. |
| 2,760,988 A | 8/1956 | Schetty et al. |
| 3,212,900 A | 10/1965 | Oguchi et al. |
| 3,332,768 A | 7/1967 | Freund et al. |
| 3,468,898 A | 9/1969 | Cutler et al. |
| 3,907,700 A | 9/1975 | Grier |
| 4,255,431 A | 3/1981 | Junggren et al. |
| 4,366,168 A | 12/1982 | Clinton et al. |
| 4,472,582 A | 9/1984 | Cain et al. |
| 4,473,692 A | 9/1984 | Miyasaka et al. |
| 4,764,534 A | 8/1988 | Clinton et al. |
| 5,041,604 A | 8/1991 | Saito et al. |
| 5,252,561 A | 10/1993 | Hornykiewytsch et al. |
| 5,630,882 A | 5/1997 | de Miniac |
| 6,509,360 B1 | 1/2003 | Malamas et al. |

(Continued)

FOREIGN PATENT DOCUMENTS

| | | | |
|---|---|---|---|
| EP | 0289879 A1 | 11/1988 | |
| EP | 0671174 A2 | 9/1995 | |
| GB | 1460559 | 1/1977 | |
| GB | 2055094 A | * 2/1981 | ............ C07H 19/01 |
| JP | S5721320 A | 2/1982 | |
| JP | H02145588 A | 6/1990 | |
| WO | 2013/110077 A1 | 7/2013 | |
| WO | 2014/066622 A2 | 5/2014 | |
| WO | 2014/099837 A1 | 6/2014 | |

OTHER PUBLICATIONS

Rogers, N. E., & Allen, R. J. (2002). Radiation effects on breast reconstruction with the deep inferior epigastric perforator flap. Plastic and reconstructive surgery, 109(6), 1919-24. (Year: 2002).*

(Continued)

*Primary Examiner* — Dale R Miller
(74) *Attorney, Agent, or Firm* — Pepper Hamilton LLP

(57) ABSTRACT

Disclosed are methods of treating fibrosis in a patient in need thereof that includes administering to the patient an amount of an active agent, as identified herein, that is therapeutically effective to inhibit myofibroblast formation and thereby treat the fibrosis. Also disclosed is a recombinant cell line that includes a recombinant gene that expresses a detectable expression product in a dose-dependent response to TGFβ, as well as methods of identifying a compound that inhibits TGFβ-mediated expression of the detectable expression product.

10 Claims, 26 Drawing Sheets
Specification includes a Sequence Listing.

(56) References Cited

U.S. PATENT DOCUMENTS

| | | |
|---|---|---|
| 6,596,726 B1 | 7/2003 | Bridges et al. |
| 7,132,438 B2 | 11/2006 | Frenkel et al. |
| 8,318,737 B2 | 11/2012 | Foley et al. |
| 8,609,663 B2 | 12/2013 | Finberg et al. |
| 8,796,285 B2 | 8/2014 | Zhang et al. |
| 2004/0171603 A1 | 9/2004 | Pato et al. |
| 2006/0040980 A1 | 2/2006 | Lind et al. |
| 2006/0269485 A1 | 11/2006 | Friedman et al. |
| 2007/0202051 A1 | 8/2007 | Schuschnig |
| 2009/0054381 A1 | 2/2009 | Letts |
| 2009/0130078 A1 | 5/2009 | Kivlighn et al. |
| 2009/0143368 A1 | 6/2009 | Shiraki et al. |
| 2010/0093613 A1 | 4/2010 | Kunkel et al. |
| 2011/0274703 A1 | 11/2011 | Agarwal et al. |
| 2013/0225595 A1 | 8/2013 | Gillies et al. |
| 2013/0274215 A1* | 10/2013 | Thies .................. A61K 31/00 514/30 |

OTHER PUBLICATIONS

Otoguro, K., Ishiyama, A., Ui, H., Kobayashi, M., Manabe, C., Yan, G., . . . & Omura, S. (2002). In vitro and in vivo antimalarial activities of the monoglycoside polyether antibiotic, K-41 against drug resistant strains of Plasmodia. The Journal of antibiotics, 55(9), 832-834. (Year: 2002).*

Keisslich et al., "Epigenetic Control of Epithelial-mesenchymal-transition in Human Cancer," 1:3-11 (2013).

Classen et al., "Fibrotic Changes After Postmastectomy Radiotherapy and Reconstructive Surgery in Breast Cancer," Strahlenther Oncol. 186:630-636 (2010).

Huczynski, "Polyether Ionophores—Promising Bioactive Molecules for Cancer Therapy," Bioorg. Med. Chem. Lett. 22:7002-7010 (2012).

Liang et al., "The Optimal Concentration of Topical Hydroxycamptothecin in Preventing Intraarticular Scar Adhesion," Scientific Reports 4:4621, pp. 1-4 (2014).

PCT International Search Report and Written Opinion corresponding to PCT/US2015/036059, filed Jun. 16, 2015 (dated Dec. 14, 2015).

Chapman et al., "Forty Years of Monensin for the Control of Coccidiosis in Poultry," Poultry Science 89:1788-1801 (2010).

International Preliminary Report on Patentability for corresponding International Patent Application No. PCT/US2015/036059 (dated Dec. 20, 2016).

Nagao et al., "Synthesis and Structure-Activity Relationships of Novel, Potent, Orally Active Hypoxia-Inducible Factor-1 Inhibitors," Bioorganic & Medicinal Chemistry 22:5513-5529 (2014).

Karthikeyan et al., "Synthesis and Antimicrobial Studies of Novel Dichlorofluorophenyl Containing Aminotriadiazines," European J. of Medicinal Chemistry 43:309-314 (2008).

* cited by examiner

SEQUENCE LISTING

```
<160> NUMBER OF SEQ ID NOS: 5

<210> SEQ ID NO 1
<211> LENGTH: 170
<212> TYPE: DNA
<213> ORGANISM: Artificial
<220> FEATURE:
<223> OTHER INFORMATION: TK Promoter

<400> SEQUENCE: 1
cggccccgcc cagcgtcttg tcattggcga attcgaacac gcagatgcag tcggggcggc      60
gcggtccgag gtccacttcg catattaagg tgacgcgtgt ggcctcgaac accgagcgac     120
cctgcagcga cccgcttaac agcgtcaaca gcgtgccgca gatctcgaga                170

<210> SEQ ID NO 2
<211> LENGTH: 83
<212> TYPE: DNA
<213> ORGANISM: Artificial
<220> FEATURE:
<223> OTHER INFORMATION: TGF-beta Response Element
```

<400> SEQUENCE: 2
tactaagtct agacggcagt ctagacgtac taagtctaga cggcagtcta gacgtagagc    60
tcggccccgc ccagcgtctt gtc    83

<210> SEQ ID NO 3
<211> LENGTH: 1719
<212> TYPE: DNA
<213> ORGANISM: Artificial
<220> FEATURE:
<223> OTHER INFORMATION: Luciferase Open Reading Frame

<400> SEQUENCE: 3
atggaagatg ccaaaaacat taagaagggc ccagcgccat tctacccact cgaagacggg    60
accgccggcg agcagctgca caaagccatg aagcgctacg ccctggtgcc cggcaccatc   120
gcctttaccg acgcacatat cgaggtggac attacctacg ccgagtactt cgagatgagc   180
gttcggctgg cagaagctat gaagcgctat gggctgaata caaaccatcg gatcgtggtg   240
tgcagcgaga atagcttgca gttcttcatg cccgtgttgg gtgccctgtt catcggtgtg   300
gctgtggccc cagctaacga catctacaac gagcgcgagc tgctgaacag catgggcatc   360
agccagccca ccgtcgtatt cgtgagcaag aaagggctgc aaaagatcct caacgtgcaa   420
aagaagctac cgatcataca aaagatcatc atcatggata gcaagaccga ctaccagggc   480
ttccaaagca tgtacacctt cgtgacttcc catttgccac ccggcttcaa cgagtacgac   540
ttcgtgcccg agagcttcga ccgggacaaa accatcgccc tgatcatgaa cagtagtggc   600
agtaccggat tgcccaaggg cgtagcccta ccgcaccgca ccgcttgtgt ccgattcagt   660
catgcccgcg accccatctt cggcaaccag atcatccccg acaccgctat cctcagcgtg   720
gtgccatttc accacggctt cggcatgttc accacgctgg gctacttgat ctgcggcttt   780
cgggtcgtgc tcatgtaccg cttcgaggag gagctattct tgcgcagctt gcaagactat   840
aagattcaat ctgccctgct ggtgcccaca ctatttagct tcttcgctaa gagcactctc   900
atcgacaagt acgacctaag caacttgcac gagatcgcca gcggcggggc gccgctcagc   960
aaggaggtag gtgaggccgt ggccaaacgc ttccacctac caggcatccg ccagggctac  1020
ggcctgacag aaacaaccag cgccattctg atcacccccg aaggggacga caagcctggc  1080
gcagtaggca aggtggtgcc cttcttcgag gctaaggtgg tggacttgga caccggtaag  1140
acactgggtg tgaaccagcg cggcgagctg tgcgtccgtg gccccatgat catgagcggc  1200
tacgttaaca cccccgaggc tacaaacgct ctcatcgaca aggacggctg gctgcacagc  1260
ggcgacatcg cctactggga cgaggacgag cacttcttca tcgtggaccg gctgaagagc  1320
ctgatcaaat acaagggcta ccaggtagcc ccagccgaac tggagagcat cctgctgcaa  1380
caccccaaca tcttcgacgc cggggtcgcc ggcctgcccg acgacgatgc cggcgagctg  1440
cccgccgcag tcgtcgtgct ggaacacggt aaaaccatga ccgagaagga gatcgtggac  1500
tatgtggcca gccaggttac aaccgccaag aagctgcgcg gtggtgttgt gttcgtggac  1560
gaggtgccta aaggactgac cggcaagttg gacgcccgca agatccgcga gattctcatt  1620
aaggccaaga agggcggcaa gatcgccgtg aattctcacg gcttccctcc cgaggtggag  1680
gagcaggccg ccggcaccct gcccatgagc tgcgcccag                        1719

<210> SEQ ID NO 4
<211> LENGTH: 90
<212> TYPE: DNA
<213> ORGANISM: Artificial

```
<220> FEATURE:
<223> OTHER INFORMATION: Forward PCR Primer

<400> SEQUENCE: 4
aggtacctac taagtctaga cggcagtcta gacgtactaa gtctagacgg cagtctagac      60
gtagagctcg gccccgccca gcgtcttgtc                                       90

<210> SEQ ID NO 5
<211> LENGTH: 28
<212> TYPE: DNA
<213> ORGANISM: Artificial
<220> FEATURE:
<223> OTHER INFORMATION: Reverse PCR Primer

<400> SEQUENCE: 5
taaagcttct cgagatctgc ggcacgct                                         28
```

SMALL MOLECULE ANTI-SCARRING AGENTS

This application is a national stage application under 35 U.S.C. § 371 of PCT Application No. PCT/US2015/036059, filed Jun. 16, 2015, which claims the benefit of U.S. Provisional Patent Application Ser. No. 62/012,602, filed Jun. 16, 2014, and U.S. Provisional Patent Application Ser. No. 62/114,932, filed Feb. 11, 2015, each of which is hereby incorporated by reference in its entirety.

This invention was made with government support under grant numbers ES023032, EY023239, and ES024037 awarded by the National Institutes of Health. The government has certain rights in the invention.

FIELD OF THE DISCLOSURE

This application is directed to the identification of compounds and pharmaceutical compositions, and methods of using the same for the treatment or prevention of fibrosis and fibrotic-related disorders in an individual.

BACKGROUND OF THE DISCLOSURE

Formation of excess scar tissue, called fibrosis in organs, affects billions of people world-wide. Fibrosis of the lung, heart, kidney, liver, eye, bone marrow, etc. is responsible for morbidity and mortality. Scarring is a consequence of the normal wound healing response. However, scar formation can be exuberant leading to hypertrophic scarring and/or fibrosis that can ultimately lead to a loss of tissue function (Friedlander M., "Fibrosis and diseases of the eye," *J. Clin. Invest.* 117:576-586 (2007); Noble et al., "Pulmonary fibrosis: patterns and perpetrators," *J. Clin. Invest.* 122:2756-2762 (2012); Bahn R. S., "Graves' ophthalmopathy," *N. Engl. J. Med.* 362:726-738 (2010); and Hinz B., "Formation and function of the myofibroblast during tissue repair," *J. Invest. Dermatol.* 127:526-537 (2007)). While there is a major knowledge gap as to why scarring sometimes proceeds out of control, hypertrophic scarring usually results from physical injury, such as laceration or surgery or from burns either thermally, chemically or radiation induced (Niessen et al., "On the nature of hypertrophic scars and keloids: a review," *Plast. Reconstr. Surg.* 104:1435-1458 (1999)). For example, an unfortunate consequence of severe heat-induced burns is the development of debilitating hypertrophic scars (Gauglitz et al., "Hypertrophic scarring and keloids: pathomechanisms and current and emerging treatment strategies," *Mol. Med.* 17:113-125 (2011)). Chronic inflammation and autoimmune disease can also lead to aberrant tissue reorganization and scarring (Lehmann et al., "Immune mechanisms in thyroid eye disease," *Thyroid: official journal of the American Thyroid Association* 18:959-965 (2008); Phan S. H., "The myofibroblast in pulmonary fibrosis," *Chest* 122:286S-289S (2002)). Thyroid eye disease (TED) is an example of an autoimmune disease in which immune cells target the muscle and connective tissue in the ocular orbit leading to orbital tissue remodeling and excessive scarring (Bahn R. S., "Graves' ophthalmopathy," *N. Engl. J. Med.* 362:726-738 (2010); Kuriyan et al., "The eye and thyroid disease," *Curr. Opin. Ophthalmol.* 19:499-506 (2008)). While aberrant scarring is observed in numerous pathologies, there are few, if any effective therapies that limit or prevent scarring.

The key effector cell in scar formation is the contractile and secretory myofibroblast (Hinz et al., "The myofibroblast: one function, multiple origins," *Am. J. Pathol.* 170: 1807-1816 (2007)). Myofibroblasts are derived from tissue resident fibroblasts, epithelial-mesenchymal transitions, circulating fibrocytes, mesenchymal stem cells or other progenitor cells (Desmouliere et al., "Tissue repair, contraction, and the myofibroblast," *Wound Repair Regen.* 13:7-12 (2005)). Myofibroblasts highly express alpha-smooth muscle actin ($\alpha$SMA), an important protein required for wound contraction, and these cells produce large amounts of extracellular matrix (ECM) material including collagen, fibronectin and glycosaminoglycans (Hinz et al., "Recent developments in myofibroblast biology: paradigms for connective tissue remodeling," *Am. J. Pathol.* 180:1340-1355 (2012); Smith et al., "Fibroblasts as sentinel cells. Synthesis of chemokines and regulation of inflammation," *Am. J. Pathol.* 151:317-322 (1997)). The contraction of myofibroblasts and their excessive production of ECM material such as collagen result in rigid tissue formation and increases in tissue size. In addition to their contractile phenotype, myofibroblasts also secrete a variety of cytokines including IL-6, MCP-1 and TGF$\beta$ that recruit immune cells and lead to further myofibroblast formation (Micallef et al., "The myofibroblast, multiple origins for major roles in normal and pathological tissue repair," *Fibrogenesis & Tissue Repair* 5:S5 (2012)).

Despite the magnitude of the problem there are no effective anti-scarring approaches of consequence. New directed therapies to prevent scar formation are urgently needed. It would be desirable, therefore, to identify small molecule compounds that possess an ability to disrupt myofibroblast differentiation and thereby modulate scarring or fibrosis.

The present invention is directed to overcoming these and other deficiencies in the art.

SUMMARY OF THE DISCLOSURE

A first aspect of the disclosure relates to a method of treating fibrosis in a patient in need thereof. This method includes administering to the patient an amount of a polyether antibiotic that is therapeutically effective to inhibit myofibroblast formation and thereby treat the fibrosis.

A second aspect of the disclosure relates to a method of treating fibrosis in a patient in need thereof. This method includes administering to the patient an amount of one or more of amsacrine, alexidine, bithionate, or a combination thereof, wherein the amount is therapeutically effective to inhibit myofibroblast formation and thereby treat the fibrosis.

A third aspect of the disclosure relates to a method of treating fibrosis in a patient in need thereof. This method includes administering to the patient an amount of one or more compounds according to formula (I) as disclosed herein, formula (II) as disclosed herein, formula (III) as disclosed herein, formula (IV) as disclosed herein, formula (V) as disclosed herein, formula (VI) as disclosed herein, formula (VII) as disclosed herein, formula (VIII) as disclosed herein, formula (IX) as disclosed herein, formula (X) as disclosed herein, formula (XI) as disclosed herein, formula (XII) as disclosed herein, formula (XIII) as disclosed herein, formula (XIV) as disclosed herein, formula (XV) as disclosed herein, formula (XVI) as disclosed herein, formula (XVII) as disclosed herein, formula (XVIII) as disclosed herein, formula (XIX) as disclosed herein, formula (XX) as disclosed herein, formula (XXI) as disclosed herein, formula (XXII) as disclosed herein, formula (XXIII) as disclosed herein, formula (XXIV) as disclosed herein, or a combination thereof, wherein the amount is therapeutically effective to inhibit myofibroblast formation and thereby treat the fibrosis.

A fourth aspect of the disclosure relates to a method of treating fibrosis in a patient in need thereof. This method includes administering to the patient an amount of one or more agents selected from the group of 10-hydroxycamptothecin, omeprazole, esomeprazole, flutamide, 4,5-dichloro-2-methyl-N-(4-pyridinylmethyl)benzenesulfonamide, N-(2-methoxyphenyl)-3-phenyl-2-propynamide, 3-amino-4-chloro-N,N-diethylbenzamide, 4-ethoxy-2,3-dimethyl-N-(4-pyridinylmethyl)benzenesulfonamide, {5-[(4-chlorophenyl)thio]-2-furyl}methanol, N-(1-phenylethyl)[1]benzofuro[3,2-d]pyrimidin-4-amine hydrochloride, 3-[3-(2-chlorophenyl)acryloyl]-4,6-dimethyl-2(1H)-pyridinone, ethyl 2-amino-7-(hydroxyimino)-4,5,6,7-tetrahydro-1-benzothiophene-3-carboxylate, 4-fluoro-3-methyl-N-(4-pyridinylmethyl)benzenesulfonamide, 3-(4-fluorophenyl)-2-methyl-5-phenylpyrazolo[1,5-a]pyrimidin-7(4H)-one, N-[4-(allyloxy)phenyl]-4-(4-morpholinomethyl)benzamide, 3-fluoro-N-(4-pyridinylmethyl)benzenesulfonamide, N-{4-[(tert-butylamino)sulfonyl]phenyl}isonicotinamide, N-methyl-2-(2-phenoxyethoxy)benzamide, N-1H-benzimidazol-2-yl-2-bromobenzamide, 3-benzyl-N-(4-methylphenyl)-7H-[1,2,4]triazolo[3,4-b][1,3,4]thiadiazin-6-amine, 5-(4-chlorophenyl)-2-methyl-3-phenylpyrazolo[1,5-a]pyrimidin-7(4H)-one, 4-chloro-N-[1-(3,4-dimethylphenyl)ethyl]-1-methyl-1H-pyrazole-5-carboxamide, and 3-(2-furyl)-11-methyl-2,3,4,5-tetrahydro-1H-dibenzo[b,e][1,4]diazepin-1-one, wherein the amount is therapeutically effective to inhibit myofibroblast formation and thereby treat the fibrosis.

A fifth aspect of the disclosure relates to a pharmaceutical or veterinary composition that includes a carrier, an effective amount of a polyether antibiotic and an effective amount of a compound according to formula (I) as disclosed herein, formula (II) as disclosed herein, formula (III) as disclosed herein, formula (IV) as disclosed herein, formula (V) as disclosed herein, formula (VI) as disclosed herein, formula (VII) as disclosed herein, formula (VIII) as disclosed herein, formula (IX) as disclosed herein, formula (X) as disclosed herein, formula (XI) as disclosed herein, formula (XII) as disclosed herein, formula (XIII) as disclosed herein, formula (XIV) as disclosed herein, formula (XV) as disclosed herein, formula (XVI) as disclosed herein, formula (XVII) as disclosed herein, formula (XVIII) as disclosed herein, formula (XIX) as disclosed herein, formula (XX) as disclosed herein, formula (XXI) as disclosed herein, formula (XXII) as disclosed herein, formula (XXIII) as disclosed herein, or formula (XXIV) as disclosed herein, which is intended to include one or more of amsacrine, alexidine, bithionate, benzbromarone, piperlongumine, 10-hydroxycamptothecin, omeprazole, esomeprazole, flutamide, 4,5-dichloro-2-methyl-N-(4-pyridinylmethyl)benzenesulfonamide, N-(2-methoxyphenyl)-3-phenyl-2-propynamide, 3-amino-4-chloro-N,N-diethylbenzamide, 4-ethoxy-2,3-dimethyl-N-(4-pyridinylmethyl)benzenesulfonamide, {5-[(4-chlorophenyl)thio]-2-furyl}methanol, N-(1-phenylethyl)[1]benzofuro[3,2-d]pyrimidin-4-amine hydrochloride, 3-[3-(2-chlorophenyl)acryloyl]-4,6-dimethyl-2(1H)-pyridinone, ethyl 2-amino-7-(hydroxyimino)-4,5,6,7-tetrahydro-1-benzothiophene-3-carboxylate, 4-fluoro-3-methyl-N-(4-pyridinylmethyl)benzenesulfonamide, 3-(4-fluorophenyl)-2-methyl-5-phenylpyrazolo[1,5-a]pyrimidin-7(4H)-one, N-[4-(allyloxy)phenyl]-4-(4-morpholinomethyl)benzamide, 3-fluoro-N-(4-pyridinylmethyl)benzenesulfonamide, N-{4-[(tert-butylamino)sulfonyl]phenyl}isonicotinamide, N-methyl-2-(2-phenoxyethoxy)benzamide, N-1H-benzimidazol-2-yl-2-bromobenzamide, 3-benzyl-N-(4-methylphenyl)-7H-[1,2,4]triazolo[3,4-b][1,3,4]thiadiazin-6-amine, 5-(4-chlorophenyl)-2-methyl-3-phenylpyrazolo[1,5-a]pyrimidin-7(4H)-one, 4-chloro-N-[1-(3,4-dimethylphenyl)ethyl]-1-methyl-1H-pyrazole-5-carboxamide, and 3-(2-furyl)-11-methyl-2,3,4,5-tetrahydro-1H-dibenzo[b,e][1,4]diazepin-1-one. Effective amounts are those which are effective to inhibit myofibroblast formation and thereby treat fibrosis.

A sixth aspect of the disclosure relates to a recombinant cell line. This recombinant cell line includes a recombinant gene that expresses a detectable expression product in a dose-dependent response to TGFβ concentration. The HEK293-Thy1 SBE-Luc cell line described in the Examples represents a non-limiting example thereof.

A seventh aspect of the disclosure relates to a method of identifying a compound that inhibits TGFβ-mediated cellular activity. The method includes growing a recombinant cell line according to the fifth aspect of the disclosure in the presence of TGFβ and a compound of interest, and measuring the amount of the detectable expression product and comparing the measured amount to a control lacking the compound of interest and/or a control lacking TGFβ, wherein a significant difference in the measured amount of the detectable expression product, relative to the control, indicates that the compound of interest inhibits TGFβ-mediated cellular activity.

While scarring is a component of wound healing, excessive scar formation is a debilitating condition that results in pain, loss of tissue function and even death. Many tissues including the lung, heart, skin, and eye can develop excessive scar tissue as a result of tissue injury, chronic inflammation or autoimmune disease. Unfortunately, there are few, if any, effective treatments to prevent excess scarring and new treatment strategies are needed. Using HEK293FT cells stably transfected with a TGFβ-dependent luciferase reporter, a small molecule screen was performed to identify novel compounds with anti-scarring activity. Several small molecules were identified that could disrupt TGFβ-dependent myofibroblast formation, and thereby mitigate excessive scarring and fibrosis. These results reveal that several polyether antibiotics, including salinomycin, are potent inhibitors of TGFβ-dependent human myofibroblast formation. Salinomycin potently inhibited the formation of scar-forming myofibroblasts, and salinomycin (250 nM) blocked TGFβ-dependent expression of the cardinal myofibroblast products alpha smooth muscle actin, calponin and collagen in primary human fibroblasts without causing cell death. Expression of constitutively active mitogen activated kinase kinase (MKK) 6, which activates p38 MAPK, attenuates the ability of salinomycin to block myofibroblast formation indicating that salinomycin targets the p38 kinase pathway to disrupt TGFβ signaling. These data identify salinomycin and other polyether antibiotics as a novel class of compounds useful as anti-scarring therapeutic agents.

Using this same novel reporter cell line, both the Spectrum library of natural compounds and Chembridge library of 20,000 synthetic molecules (designed by medicinal chemists) were screened, and a significant number of small molecules that inhibit myofibroblast formation in human and mouse fibroblasts were discovered. Importantly, many of the compounds disclosed herein lack overt cytotoxic effects and, consequently, should also be useful candidates for the therapeutic treatment or prevention of fibrosis.

BRIEF DESCRIPTION OF THE DRAWINGS

FIG. 1A is a diagram of Smad-dependent reporter construct. Four tandem Smad binding elements (SBE) were inserted upstream of the minimal Thymidine Kinase (TK) promoter. Downstream of the promoter is a destabilized version of the firefly luciferase gene (luc2P) present in the pLuc2P-Hygro plasmid which also harbors the hygromycin resistance gene. The plasmid was introduced into HEK293FT cell line and individual colonies were selected with hygromycin (200 ug/ml) to develop a Smad/TGFβ dependent-luciferase reporter cell line. FIG. 1B is a graph illustrating the response of the reporter cell line to 1 ng/ml treatment of TGFβ for 20 hours, which results in an approximately 20-fold increase of luciferase activity. FIG. 1C illustrates the structure of salinomycin (SNC), which is one of several members of the 2300 compound Spectrum collection that blocked TGFβ-induced luciferase activity when screened with the HEK293FT-luc reporter line of FIG. 1A. The polyether ionophore salinomycin was further tested in a dual luciferase screen including a constitutive renilla luciferase to normalize the SBE-luciferase activity, which demonstrated that it was a potent inhibitor of TGFβ. FIG. 1D shows that salinomycin exhibited a dose dependent decrease in TGFβ-induced SBE-luciferase activity. 1 uM salinomycin reduced SBE-luciferase activity to below baseline levels while 100 nM salinomycin reduced SBE-luciferase activity more than 3-fold. Experiments were repeated three times in triplicate and similar results were observed in all tests. * $p<0.05$.

FIG. 2A shows that human fibroblasts were treated with varying doses of salinomycin and treated with TGFβ (1 ng/ml) for 72 hours. The cells were then lysed and analyzed by Western blot for the myofibroblast markers alpha-smooth muscle actin (αSMA) and calponin. β-tubulin was used as a loading control. FIG. 2B shows densitometry analysis of blots in panel A, where a dose-dependent decrease in myofibroblast markers αSMA and calponin was observed. Salinomycin treatments of 100 and 200 nM reduced expression of myofibroblast markers to below baseline levels. FIG. 2C shows the results of a slot blot analysis for collagen I using culture supernatants from cells treated as in panel FIG. 2A. Salinomycin similarly reduced collagen I levels in a dose-dependent manner.

FIG. 3A shows molecular structures of narasin, monensin and clioquionol. Narasin, a methylated derivative of salinomycin, and monensin are polyether ionophores whereas clioquinol is an unrelated ionophore. FIG. 3B shows Western blot results using cell lysates from human fibroblasts treated with vehicle (DMSO), TGFβ or TGFβ plus 250 nM of the indicated compounds for 72 hours, followed by analysis of the myofibroblast markers αSMA and calponin. FIG. 3C shows densitometry analysis of Western blots shown in FIG. 3B. Salinomycin, narasin and monensin all inhibited expression of αSMA and calponin whereas clioquinol did not.

FIG. 4A shows the results of a cell viability assay using human fibroblasts treated with vehicle (DMSO), 50, 100 or 250 nM salinomycin, TGFβ, TGFβ plus 250 nM salinomycin or puromycin (5 ug/ml) for 72 hours in the presence of alamar blue, a redox sensitive fluorescent dye. After 72 hours, fluorescence was measured to check cellular viability. Puromycin, which served as a positive control resulted in a total loss of cell viability, whereas salinomycin did not significantly affect cell viability at doses tested, either in the presence or absence of TGFβ. FIG. 4B shows the results of a TGFβ-induced proliferation assay using human fibroblasts treated with vehicle (DMSO), 250 nM salinomycin, 250 nM narasin, TGFβ alone or TGFβ plus salinomycin or narasin (250 nM) for 24 hours before addition of bromodeoxyuridine (BrdU). BrdU treatment was an additional 24 hours and then cells were fixed and stained for BrdU incorporation, which serves as a measure of cell proliferation. Salinomycin and narasin did not affect basal fibroblast proliferation (first 3 columns), however, salinomycin and narasin significantly blocked TGFβ induced proliferation (last 3 columns). Results are from a representative experiment performed in triplicate. * $p<0.01$.

FIG. 5A shows a Western blot of cell lysates obtained from human orbital fibroblasts treated with vehicle, TGFβ or TGFβ plus 250 nM salinomycin. Cells were harvested at various time points and analyzed for phosphorylated versions of SMAD2/3 and p38. Salinomycin reduced Smad2/3 and p38 phosphorylation at 5 hour and 24 hour TGFβ treatments. FIG. 5B is a pair of graphs that together show densitometry of Western blots in FIG. 5A. Salinomycin reduced TGFβ induced phospho-Smad2/3 levels by 2-fold at 5 hours and by 5-fold at 24 hours. Likewise, salinomycin reduced phospho-p38 levels by more than 2-fold at 5 hours and by 10-fold at 24 hours. Data are representative of two different experiments performed with human fibroblasts.

FIG. 6A shows that a Smad-luc reporter, constitutive renilla reporter and either a control plasmid or the pcDNA3.1 flag-MKK6 (glu) plasmid were introduced into human orbital fibroblasts by electroporation. After electroporation, cells were treated with vehicle (DMSO), TGFβ or TGFβ plus 250 nM salinomycin. After 24 hours, cells were lysed and luciferase activity was measured. Smad-luc activity was normalized to renilla activity. Salinomycin blocked TGFβ induced Smad-luc activity. However, the presence of MKK6(glu) attenuated the effect of salinomycin on the Smad reporter. FIG. 6B shows Western blot results for human orbital fibroblasts into which a control plasmid or the pcDNA3.1 flag-MKK6 (glu) plasmid was introduced by electroporation. Cells were then treated with vehicle, TGFβ or TGFβ plus 250 nM salinomycin for 24 hours. FIG. 6C shows Western blot results for cells treated as in FIG. 6B, however, cells were cultured for 72 hours to allow sufficient time for myofibroblast differentiation. The experiment was repeated three times in different fibroblast strains, results are from one representative set.

DETAILED DESCRIPTION

Figure 1A:
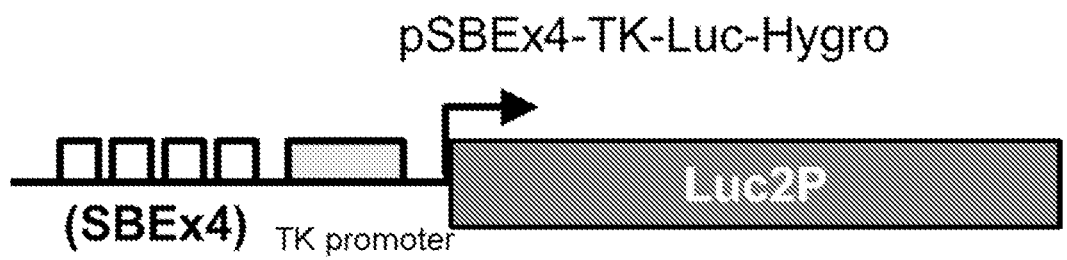
FIGS. 1A-D show that small molecule screen identified salinomycin as a potential anti-scarring compound.

The present invention relates to a method of treating fibrosis in a patient in need thereof. This method includes administering to the patient an amount of a compound (or active agent) that is therapeutically effective to inhibit myofibroblast formation and thereby treat the fibrosis.

The patient can be any mammal susceptible to fibrosis or exhibiting signs of fibrosis, including without limitation, humans, non-human primates, and various domesticated animals including livestock (dairy cows, steer, pigs, horses, mules, donkeys, llamas, alpaca, sheep, etc.), household animals (dogs, cats, rabbits, ferrets, chinchilla, rodents), and lab animals (typically rodents and rabbits).

Because myofibroblasts are fundamentally involved in scar formation, they represent ideal targets for new therapeutic options to limit or even reverse scarring.

Myofibroblast differentiation is driven by the cytokine transforming growth factor-beta (TGFβ), which is produced during the natural healing process (Bourlier et al., "TGFbeta family members are key mediators in the induction of myofibroblast phenotype of human adipose tissue progenitor cells by macrophages," *PloS one* 7:e31274 (2012); George, "Regulation of myofibroblast differentiation by convergence of the Wnt and TGF-beta1/Smad signaling pathways," *J. Mol. Cell. Cardiol.* 46:610-611 (2009), each of which is hereby incorporated by reference in its entirety). TGFβ is also involved in many other cellular responses including immune suppression, cell migration and extracellular matrix remodeling (Massague, "TGFbeta signalling in context," *Nat. Rev. Mol. Cell Biol.* 13:616-630 (2012), which is hereby incorporated by reference in its entirety). While TGFβ is normally tightly regulated at multiple levels to limit its powerful effects, TGFβ is often highly expressed in conditions such as cancer, chronic inflammation and in fibrosis (Massague, "TGFbeta signalling in context," *Nat. Rev. Mol. Cell Biol.* 13:616-630 (2012), which is hereby incorporated by reference in its entirety). While driving myofibroblast formation, TGFβ regulates numerous cell signaling pathways. One key pathway activated by TGFβ is Smad dependent signaling. Smads are a family of highly conserved transcription factors that regulate expression of many genes that contain Smad-binding element (SBEs) in their promoter and/or regulatory regions (Weiss et al., "The TGFbeta superfamily signaling pathway," *Wiley Interdiscip. Rev. Dev. Biol.* 2:47-63 (2013), which is hereby incorporated by reference in its entirety). TGFβ binding to its cognate receptor on the cell surface triggers phosphorylation of the Smad family members, Smad2 and Smad3. Once phosphorylated, these transcription factors bind their binding partner namely, the coSmad, Smad4. This Smad complex is then shuttled into the nucleus where it activates transcription of myofibroblast genes including αSMA, calponin and collagen (Usuki et al., "Sequential analysis of myofibroblast differentiation and transforming growth factor-beta1/Smad pathway activation in murine pulmonary fibrosis," *J. Nippon Med. Sch.* 79:46-59 (2012); Carthy et al., "Wnt3a induces myofibroblast differentiation by upregulating TGF-beta signaling through SMAD2 in a beta-catenin-dependent manner," *PloS one* 6:e19809 (2011); and Gu et al., "Effect of TGF-beta/Smad signaling pathway on lung myofibroblast differentiation," *Acta Pharmacol. Sin.* 28:382-391 (2007), each of which is hereby incorporated by reference in its entirety).

As used herein, the expressions "fibrosis", "fibrosis conditions", and "fibrotic conditions" are intended to have the same meaning. In certain embodiments, the fibrotic conditions are those mediated by a fibrotic stimulator. Exemplary fibrotic stimulators include, without limitation, TGF-β, endothelin, lactic acid (via lactate dehydrogenase), IL-1, Thy-1 (CD90), connective tissue growth factor ("CTGF"), as well as combinations thereof. In certain embodiments, the fibrotic condition is one that is mediated by TGF-β.

In certain embodiments, the fibrotic condition is related to an autoimmune condition. In other embodiments, the fibrotic condition is subsequent to injury, including radiation, alkali burn, physical burn, surgery, physical trauma, or a combination thereof. In certain embodiments, the fibrotic condition is not secondary to a microbial infection that is treatable with a polyether antibiotic.

A number of fibrotic conditions can be treated in accordance with the present invention, including those involving internal organs such as lung, liver, kidney, heart, pancreas, gastrointestinal organs, and genitourinary organs; vascular tissue; and ocular tissue such as corneal tissue, retinal tissue, and lacrimal gland tissues.

Exemplary fibrotic conditions of the lung (i.e., pulmonary fibrosis) include, but are not limited to, idiopathic pulmonary fibrosis (IPF); idiopathic pulmonary upper lobe fibrosis (Amitani disease); familial pulmonary fibrosis; pulmonary fibrosis secondary to systemic inflammatory diseases such as, rheumatoid arthritis, scleroderma, lupus, cryptogenic fibrosing alveolitis, chronic obstructive pulmonary disease (COPD) or chronic asthma; cystic fibrosis; non-specific interstitial pneumonia (NSIP); cryptogenic organizing pneumonia (COP); progressive massive fibrosis, a complication of coal worker's pneumoconiosis; scleroderma/systemic sclerosis; bronchiolitis obliterans-organizing pneumonia; pulmonary hypertension; pulmonary tuberculosis; silicosis; asbestosis; acute lung injury; and acute respiratory distress (ARD; including bacterial pneumonia induced, trauma-induced, and viral pneumonia-induced, ventilator-induced, non-pulmonary sepsis induced).

Exemplary fibrotic conditions of the liver (i.e., liver fibrosis) include, but are not limited to, liver cirrhosis due to all etiologies; congenital hepatic fibrosis; obesity; fatty liver; alcohol induced liver fibrosis; non-alcoholic steatohepatitis (NASH); biliary duct injury; primary biliary cirrhosis; infection- or viral-induced liver fibrosis (e.g., chronic hepatitis B and C virus infections); cystic fibrosis; autoimmune hepatitis; necrotizing hepatitis; primary sclerosing cholangitis; hemochromatosis; disorders of the biliary tree; hepatic dysfunction attributable to infections.

Exemplary fibrotic conditions of the heart and/or pericardium (i.e., heart or pericardial fibrosis, or fibrosis of the associate vasculature) include, but are not limited to, endomyocardial fibrosis; cardiac allograft vasculopathy (CAV); myocardial infarction; atrial fibrosis; congestive heart failure; arterioclerosis; atherosclerosis; vascular stenosis; myocarditis; congestive cardiomyopathy; coronary infarcts; varicose veins; coronary artery stenosis and other post-ischemic conditions; and idiopathic retroperitoneal fibrosis.

Exemplary fibrotic conditions of the kidney (i.e., kidney fibrosis) include, but are not limited to, glomerulonephritis (including membranoproliferative, diffuse proliferative, rapidly progressive or sclerosing, post-infectious and chronic forms); diabetic glomerulosclerosis; focal segmental glomerulosclerosis; IgA nephropathy; diabetic nephropathy; HIV-associated nephropathy; membrane nephropathy; glomerulonephritis secondary to systemic inflammatory diseases such as lupus, scleroderma and diabetes glomerulonephritis; idiopathic membranoproliferative glomerular nephritis; mesangial proliferative glomerulonephritis; crescentic glomerulonephritis; amyloidosis (which affects the kidney among other tissues); autoimmune nephritis; renal tubuloinsterstitial fibrosis; renal arteriosclerosis; Alport's syndrome; nephrotic syndrome; chronic renal failure; periglomerular fibrosis/atubular glomeruli; combined apical emphysema and basal fibrosis syndrome (emphysema/fibrosis syndrome); glomerular hypertension; nephrogenic fibrosing dermatopathy; polycystic kidney disease; Fabry's disease and renal hypertension.

Exemplary fibrotic conditions of the pancreas (i.e., pancreatic fibrosis) include, but are not limited to, stromal remodeling pancreatitis and stromal fibrosis.

Exemplary fibrotic conditions of the gastrointestinal tract (i.e., GI tract fibrosis) include, but are not limited to, Crohn's disease; ulcerative colitis; collagenous colitis; colorectal fibrosis; villous atrophy; crypt hyperplasia; polyp formation; healing gastric ulcer; and microscopic colitis.

Exemplary fibrotic conditions of the eye include, but are not limited to, ocular fibrosis, ophthalmic fibrosis, proliferative vitreoretinopathy; vitreoretinopathy of any etiology; fibrosis associated with retinal dysfunction; fibrosis associated with wet or dry macular degeneration; scarring in the cornea and conjunctiva; fibrosis in the corneal endothelium; anterior subcapsular cataract and posterior capsule opacification; anterior segment fibrotic diseases of the eye; fibrosis of the corneal stroma (e.g., associated with corneal opacification); fibrosis of the trabecular network (e.g., associated with glaucoma); posterior segment fibrotic diseases of the eye; fibrovascular scarring (e.g., in retinal or choroidal vasculature of the eye); retinal fibrosis; epiretinal fibrosis; retinal gliosis; subretinal fibrosis (e.g., associated with age related macular degeneration); tractional retinal detachment in association with contraction of the tissue in diabetic retinopathy; congenital orbital fibrosis; lacrimal gland fibrosis; corneal subepithelial fibrosis; and Grave's ophthalmopathy.

Additional fibrotic disorders or fibrosis resulting from any one of the aforementioned conditions include, but are not limited to, spinal cord injury/fibrosis or central nervous system fibrosis such as fibrosis after a stroke, fibrosis associated with neurodegenerative disorder such as Alzheimer's disease or multiple sclerosis; vascular restenosis; uterine fibrosis; endometriosis; ovarian fibroids; Peyronie's disease; polycystic ovarian syndrome; disease related pulmonary apical fibrosis in ankylosing spondylitis; and fibrosis incident to microbial infections (e.g., bacterial, viral, parasitic, fungal etc.).

As used herein, treatment of fibrosis or fibrotic conditions is meant to include disruption of the fibrotic processes so as to halt progression of the fibrotic condition, slow progression of the fibrotic condition, or cause regression of the fibrotic condition (i.e., improve the patient's state of health with respect to the degree of fibrosis in the affected tissue or organ). In certain embodiments, where treatment precedes onset of the fibrotic condition, i.e., treatment is performed prior to a known or an otherwise expected onset of fibrosis, then such treatment may include preventing development or onset of the fibrotic condition. Administration of the various active agents can therefore be carried out for a suitable duration to either control or halt progression of the fibrotic condition, or prevent onset thereof.

In certain embodiments, the compound or active agent is a polyether antibiotic. Exemplary polyether antibiotics include, without limitation, those selected from the group consisting of monensin, lasalocid, salinomycin, narasin, maduramycin, semduramycin, laidlomycin, lonomycin, ionomycin, nigericin, grisorixin, dianemycin, lenoremycin, antibiotic X206, alborixin, septamycin, antibiotic A204, Compound 47,224, mutalomycin, isolasalocid A, lysocellin, tetronasin, etheromycin, antibiotic X-14766A, antibiotic A-23187, antibiotic A-32887, Compound 51,532, and K41. In one particular embodiment, the polyether antibiotic is selected from the group consisting of monensin, lasalocid, salinomycin, narasin, maduramycin, semduramycin, and laidlomycin. Salinomycin and derivatives thereof are described in Hammann et al., "Anticoccidial Activity of Salinomycin Derivatives," *J. of Antibiotics* 46(3):523-525 (1993), which is hereby incorporated by reference in its entirety.

In another embodiment the compound or active agent has a structure according to formula (I), shown below, which is described in U.S. Pat. No. 6,509,360 to Malamas et al., which is hereby incorporated by reference in its entirety:

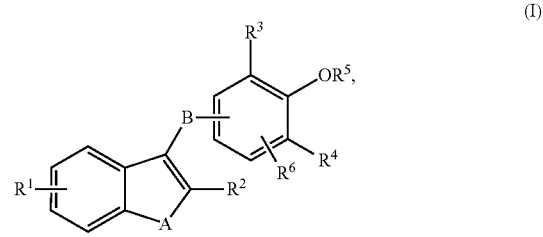

(I)

wherein:
A is O, S, or NH;
B is —(CH$_2$)$_m$—, —CH(OH)—, or carbonyl;
R$^1$ is hydrogen, nitro, halogen, alkyl of 1-6 carbon atoms, alkoxy of 1-6 carbon atoms, or trifluoromethyl;
R$^2$ is alkyl of 1-18 carbon atoms, aryl of 6-10 carbon atoms, arylalkyl of 7-15 carbon atoms, Het-alkyl wherein the alkyl moiety is 1-6 carbon atoms;
Het is

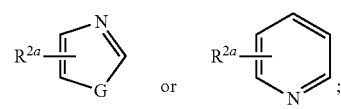

R$^{2a}$ is alkylene of 1-3 carbon atoms;
G is oxygen, sulfur, or nitrogen;
R$^3$ and R$^4$ are each, independently, hydrogen, halogen, alkyl of 1-3 carbon atoms, aryl of 6-10 carbon atoms or a heterocyclic ring of 5 to 7 ring atom containing 1 to 3 heteroatoms selected from oxygen, nitrogen, sulfur;

$R^5$ is hydrogen, alkyl of 1-6 carbon atoms, —CH($R^7$)$R^8$, —C(CH$_2$)CO$_2R^9$, —C(CH$_3$)$_2$CO$_2R^9$, CH($R^7$)(CH$_2$)CO$_2R^9$, or —CH($R^7$)C$_6$H$_4$CO$_2R^9$;

$R^6$ is hydrogen, halogen, alkyl of 1-6 carbon atoms, or —OR$^5$;

m=1-6;

n=1-6;

$R^7$ is hydrogen, alkyl of 1-6 carbon atoms, aryl of 6-10 carbon atoms, or arylalkyl of 7-15 carbon atoms;

$R^8$ is —CO$_2R^{10}$, —CONHR$^{10}$, tetrazole, or —PO$_3$H$_2$;

$R^9$ and $R^{10}$ are each, independently, hydrogen, alkyl of 1-6 carbon atoms, aryl of 6-10 carbon atoms, or arylalkyl of 7-15 carbon atoms;

or a pharmaceutically acceptable salt thereof.

One exemplary compound of formula (I) has the following structure:

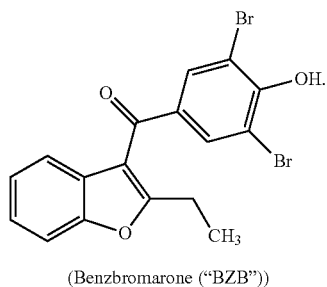 [SMILES: CCc1oc2ccccc2c1C(=O)c1cc(Br)c(O)c(Br)c1]

(Benzbromarone ("BZB"))

In another embodiment the compound has a structure according to formula (II), shown below, which is described in U.S. Pat. No. 8,318,737 to Foley et al., which is hereby incorporated by reference in its entirety:

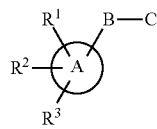

(II)

or a pharmaceutically acceptable salt or pharmaceutically acceptable derivative thereof, wherein:

Ring A is selected from the group consisting of one or more monocyclic aryl, one or more heteroaryl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen, or sulfur;

each $R^1$, $R^2$, and $R^3$ is independently selected from the group consisting of hydrogen, halogen, deuterium, CF$_3$, CN, OR, SR, NRR, NRCOR, NRCONRR, NRCO$_2$R, COR, CO$_2$R, NOR, NO$_2$, CONRR, OC(O)NRR, SO$_2$R, SO$_2$NRR, NRSO$_2$R, NRSO$_2$NRR, C(O)C(O)R, or C(O)CH$_2$C(O)R, alkyl, aryl, heteroaryl and morpholino, wherein either $R^1$ and $R^2$, or $R^2$ and $R^3$ are optionally taken together to form a 4-8 membered saturated, partially unsaturated, or fully unsaturated ring having 0-3 heteroatoms independently selected from nitrogen, oxygen, or sulfur;

each R is independently selected from hydrogen or an optionally substituted C$_1$-C$_4$ aliphatic moiety (i.e. alkyl, alkenyl, or alkynyl), or alternately, two R moieties bound to the same nitrogen atom are optionally taken together with the nitrogen atom to form a 3-7 membered saturated, partially unsaturated, or fully unsaturated ring having 1-2 additional heteroatoms independently selected from nitrogen, oxygen, or sulfur;

B is selected from:

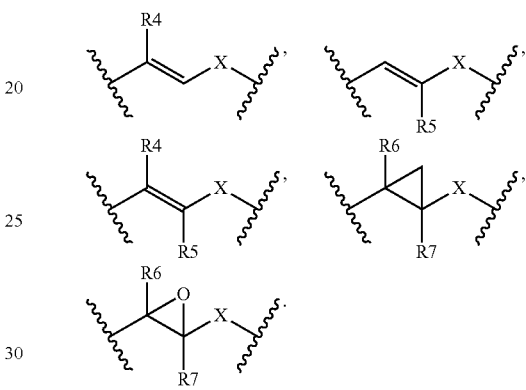

wherein $R^4$, $R^5$, $R^6$ and $R^7$ are independently selected from hydrogen, a substituted or unsubstituted C$_1$ to C$_{12}$ alkyl, a substituted or unsubstituted C$_2$ to C$_{12}$ alkenyl or a substituted or unsubstituted C$_2$ to C$_{12}$ alkynyl;

X is C(O), C(S), or S(O)$_2$; and

C is a saturated or unsaturated heteroaryl or a saturated or unsaturated C1 to C7 heterocyclic containing one or more heteroatoms wherein the heteroatoms are independently selected from N, O or S;

or C is a fused ring; and wherein any one or more H is optionally replaced by a deuterium.

In another embodiment, the compounds Formula (II) above have a structure wherein ring A is selected from:

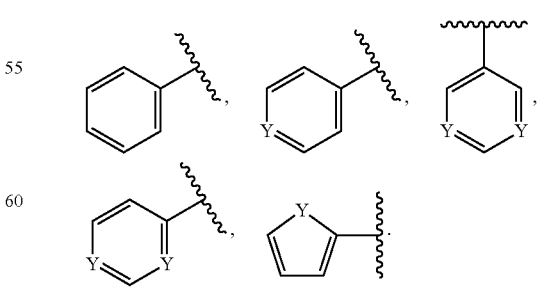

wherein the ring carries $R^1$, $R^2$ and $R^3$ as defined above;

wherein Y is N, O or S; and

C is selected from:

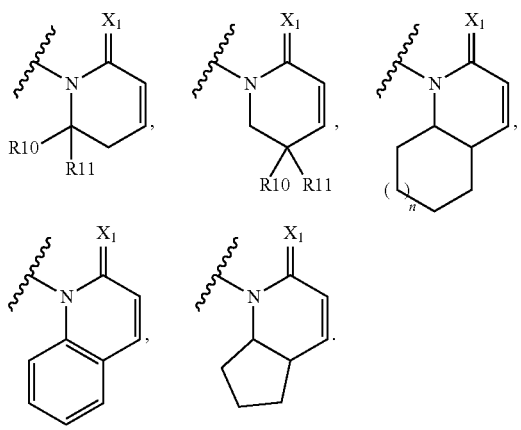

wherein the ring is optionally substituted with one or more $R^{10}$ and $R^{11}$, wherein $R^{10}$ and $R^{11}$ are independently selected from a substituted or unsubstituted $C_1$ to $C_{12}$ alkyl, a substituted or unsubstituted $C_1$ to $C_{12}$ alkenyl or a substituted or unsubstituted $C_1$ to $C_{12}$ alkynyl, an ether, a thioether, aryl, n is 1, 2 or 3;

$X_1$ is O or S;

Exemplary compounds of formula (II) have the structures shown below:

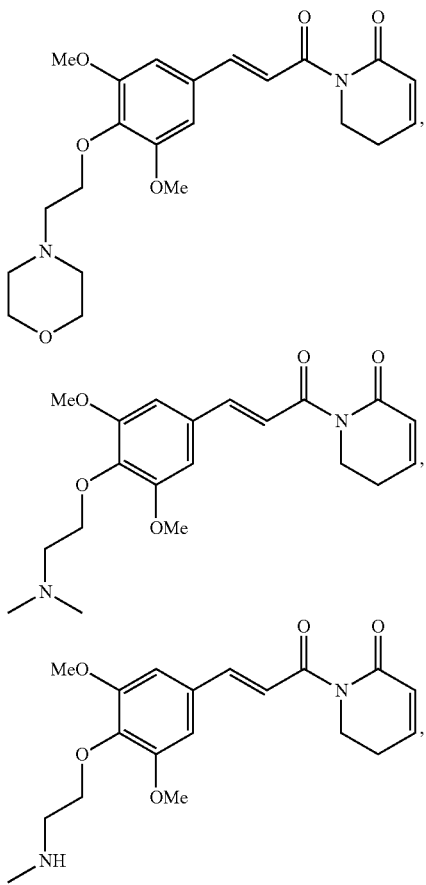

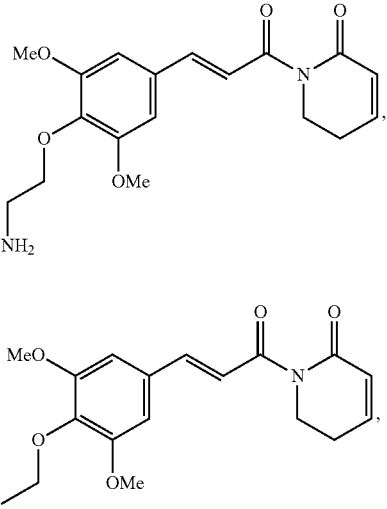

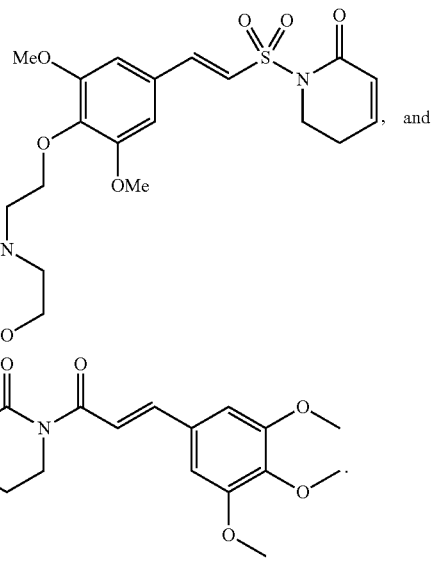

(Piplartine or piperlongumine, "PPT")

In another embodiment the compound is a 2,2'-dihydroxy halogenated diphenyl sulfide having the structure of formula (III), shown below, which is described in U.S. Pat. No. 2,353,735 to Kunz et al., which is hereby incorporated by reference in its entirety:

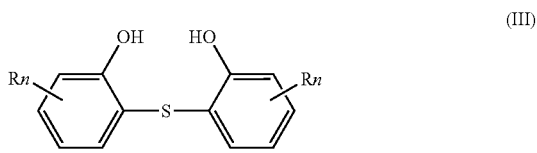

(III)

wherein R is halogen and n is an integer from 1 to 4 inclusive.

Exemplary 2,2'-dihydroxy halogenated diphenyl sulfide include

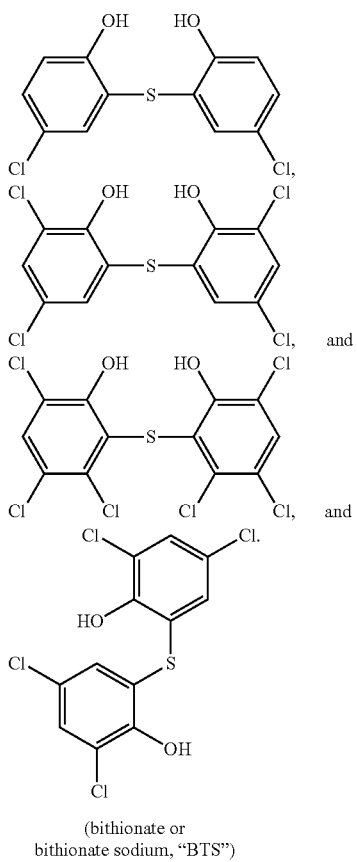

(bithionate or bithionate sodium, "BTS")

Alternatively, 2,2'-dihydroxydiphenyl sulfide having the structure shown below can be used (as described in U.S. Pat. No. 2,760,988 to Schetty et al., which is hereby incorporated by reference in its entirety):

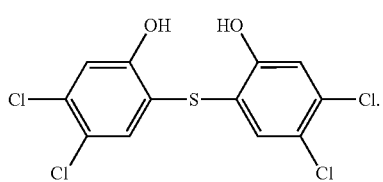 [SMILES: Oc1cc(Cl)c(Cl)cc1Sc1cc(Cl)c(Cl)cc1O]

In yet another embodiment the compound has a structure according to formula (IV), shown below, which is described in U.S. Pat. No. 3,468,898 to Cutler et al., which is hereby incorporated by reference in its entirety:

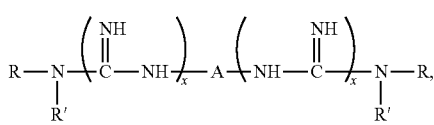

(IV)

wherein:
the bivalent bridge A is a member of the group consisting of:
(a) alkylene of from 2 to 12 carbon atoms having the valence bonds attached to different carbon atoms,
(b) —(CH$_2$)$_m$—Y—(CH$_2$)— wherein m and n each represent an integer from 2 to 6 and Y is a member of the group consisting of O and S,

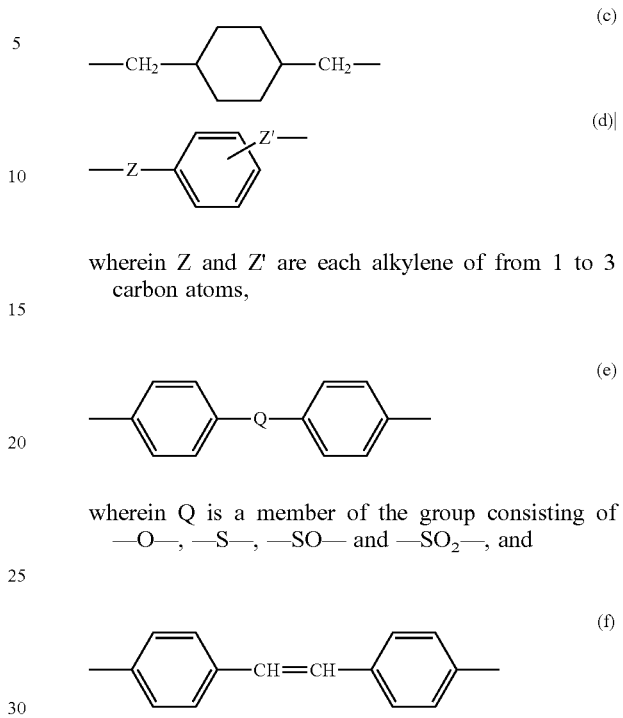

wherein Z and Z' are each alkylene of from 1 to 3 carbon atoms, wherein Q is a member of the group consisting of —O—, —S—, —SO— and —SO$_2$—, and R is a member of the group consisting of
(a) alkyl of from 6 to 16 carbon atoms, and
(b) alkyl-Y-alkylene, wherein Y is a member of the group consisting of O and S;
R' is a member of the group consisting of H and lower-alkyl; and
x is an integer from 1 to 2.

In Formula (IV), above, when representing (a), the alkylene bridge of from 2 to 12 carbon atoms, A has the formula C$_n$H$_{2n}$ (wherein n is an integer from 2 to 12), is bivalent, and has free valence bonds on different carbon atoms. The bivalent alkylene bridge can be polymethylene, represented by (CH$_2$)$_n$, —or equivalently by —(CH$_2$)$_{2-12}$— but it also includes branched-chain alkylene bridges. Thus in this sense, A includes the alpha,omega-divalent unbranched radicals ethylene, trimethylene, tetramethylene, pentamethylene, hexamethylene, heptamethylene, octamethylene, nonamethylene, decamethylene, undecamethylene, and dodecamethylene, and also includes for example the branched divalent radicals 1,3-propylene, 1,4-pentylene, 1,10-dodecamethylene, 2-methyl-1,4-butylene, 2-methyl-1,5-pentylene, and the like.

When representing the bridged grouping (CH$_2$)$_m$—Y—(CH$_2$)— (b)

A is an oxa- or thia-polymethylene radical containing from 5 to 13 atoms. The terms m and n can be the same or different, and each represents an integer of from 2 to 6. The term Y represents —O— or —S—. In this sense, therefore, A includes such radicals as

—CH$_2$CH$_2$—S—CH$_2$CH$_2$—

—CH$_2$CH$_2$—CH$_2$—S—CH$_2$—CH$_2$CH$_2$—

—CH$_2$CH$_2$CH$_2$CH$_2$—S—CH$_2$CH$_2$CH$_2$CH$_2$—

—CH$_2$CH$_2$CH$_2$CH$_2$CH$_2$—S—CH$_2$CH$_2$CH$_2$CH$_2$CH$_2$—

—CH$_2$CH$_2$CH$_2$CH$_2$CH$_2$CH$_2$—S—CH$_2$CH$_2$CH$_2$CH$_2$CH$_2$CH$_2$—

—CH$_2$CH$_2$—O—CH$_2$CH$_2$—

—CH$_2$CH$_2$CH$_2$—O—CH$_2$CH$_2$CH$_2$—

—CH$_2$CH$_2$CH$_2$CH$_2$—O—CH$_2$CH$_2$CH$_2$CH$_2$—

—CH$_2$CH$_2$CH$_2$CH$_2$CH$_2$—O—CH$_2$CH$_2$CH$_2$CH$_2$CH$_2$—

—CH$_2$CH H$_2$—S—CH$_2$—CH$_2$—CH$_2$—CH$_2$—

—CH$_2$CH$_2$CH$_2$—O—CH$_2$CH$_2$— and the like.

When A represents bridging groups (d) through (f), each of which contains one or more benzene rings, the said benzene rings can be unsubstituted or can be substituted with up to four inert substituents exemplified by, but not limited to, lower-alkyl, halogen (fluorine, chlorine, bromine, or iodine), lower-alkoxy, nitro, and hydroxy.

When representing the radical

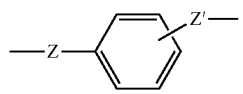

A is a divalent phenylene-bis(lower-alkylene) group. The terms Z and Z' can be the same or different and represent alkylene radicals of from 1 to 3 carbon atoms. Moreover the Z and Z' radicals can be in any of the ortho-, meta-, or para-positions relative to each other. Because of their ready availability, particularly preferred 1,4-phenylene-bis(lower-alkylene) groups are 1,2-, 1,3- or 1,4-xylylene and halo- and alkyl-substituted 1,2-, 1,3- and 1,4-xylylene. In this sense, therefore, A includes 2,3,5,6-tetramethyl-1,4-phenylene-bis(methylene), 2,5-dimethyl-1,4-phenylene-bis(methylene), 2-chloro-1,4-phenylenebis(methylene), 2,3,5,6-tetrachloro-1,4-phenylenebis(methylene) 1,2-phenylenebis(methylene), 1,3-phenylenebis(methylene), and 1,4-phenylenebis(methylene), and also 2-methyl-1,4-phenylenebis(ethylene), 1,4-phenylenebis(propylene), —CH$_2$-(1,4-phenylene)-CH$_2$CH$_2$—

—CH(CH$_3$)-(1,4-phenylene)-CH(CH$_3$)—

—CH$_2$—CH(CH$_3$)-(1,4-phenylene)-CH(CH$_3$)—CH$_2$ and the like.

In the above general Formula (IV), R is a member of the group consisting of alkyl of from 6 to 16 carbon atoms and lower-alkyl-Y-lower-alkylene, wherein Y, as above, is —O— or —S—. When representing an alkyl group of from 6 to 16 carbon atoms, R is a straight- or branched-chain saturated monovalent aliphatic radical. Thus, R includes n-hexyl, n-heptyl, n-octyl, n-nonyl, n-decyl, n-undecyl, n-dodecyl, n-tetradecyl, n-hexadecyl, 2-ethyl-1-hexyl, 2-heptyl, 2-octyl, 1,1,3,3-tetramethylbutyl, and the like.

When representing an alkyl-Y-alkylene radical, R is an oxa- or thia-interrupted alkyl group of from 6 to 16 atoms. The alkyl and alkylene radicals together contain from 5 to 15 carbon atoms, and Y is —O— or —S—. Particularly preferred alkyl-Y-alkylene groups are those wherein the alkylene moiety is propylene because of the ease of preparing the requisite alkylmercapto- and alkoxyamine intermediates from acrylonitrile by methods well-known in the art. When representing alkyl-Y-alkylene, R is thus exemplified by 3-(ethoxy)propyl, 3-(butoxy)propyl, 3-(pentoxy)propyl, 6-(propyloxy)hexyl, 3-(hexylmercapto)propyl, 3-(butylmercapto)propyl, 5-(pentylmercapto)pentyl, 7-(methoxy)heptyl, 6-(pentoxy)hexyl, 3-(tridecyloxy)propyl, 3-(dodecylmercapto)propyl, and the like.

In the above general Formula (IV), R' is H or lower-alkyl. When representing lower-alkyl, R is a straight- or branched-chain saturated aliphatic radical which contains from one to six carbon atoms. The group R' thus includes, H, methyl, ethyl, n-propyl, isopropyl, n-butyl, isobutyl, tert-butyl, n-amyl, n-hexyl, and the like.

The term x in general Formula (IV) is 1 or 2. When x represents the integer 1, the compounds are bridged-bis [guanidines], and when representing 2, the compounds are bridged-bis[biguanides].

One exemplary compound of formula (IV) has the following structure:

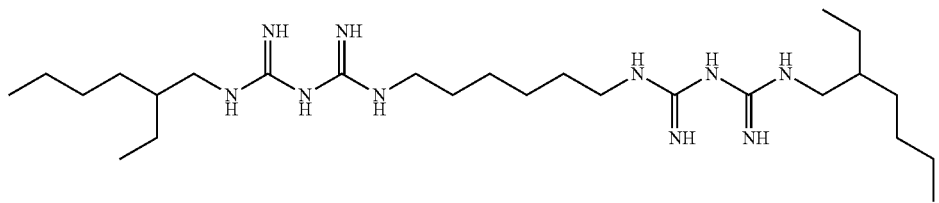

(Alexidine, "AXD")

In a further embodiment the compound is AMSA or m-AMSA or a derivative thereof according to the structure of formulae (Va, Vb, or Vc), shown below. AMSA has the following structure:

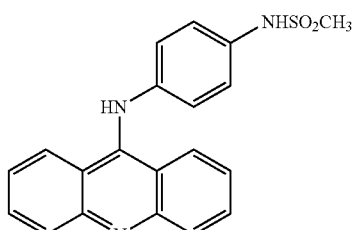

("AMSA")

(Va)

m-AMSA, amsacrine or ("ASC") has the following structure:

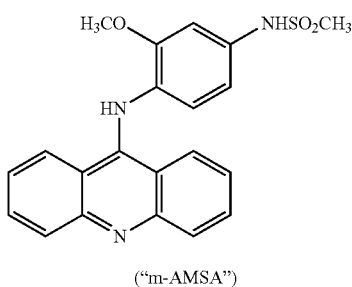

("m-AMSA")

m-AMSA derivatives are described in U.S. Pat. No. 4,472,582 to Cain et al., which is hereby incorporated by reference in its entirety. 3,5-Disubstituted m-AMSA compounds having the following formula:

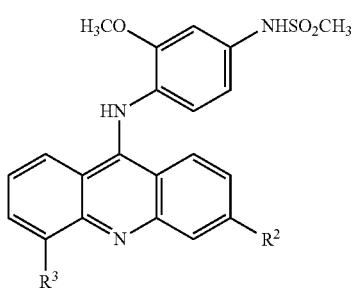

wherein $R^2$ and $R^3$ represent, respectively, —$CH_3$ and —$CONHCH_3$, —$CH_3$ and —$CONHCH_2CONH_2$, —Cl and —$CONHCH_2CONH_2$, —$CONHCH_3$ and —$CH_3$; and acid additional salts thereof.

In yet another embodiment the compound is a 10-substituted camptothecin derivative having the following structure according to formula (VI), shown below, which is described in U.S. Pat. No. 4,473,692 to Miyasaka et al., which is hereby incorporated by reference in its entirety:

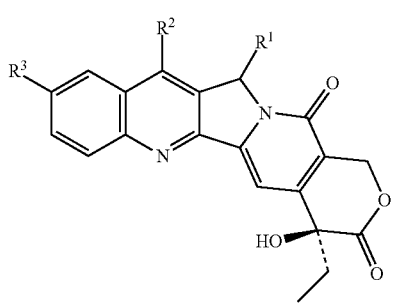

wherein $R^1$ is a hydrogen atom, an alkyl group, a hydroxyl group, an alkoxy group or an acyloxy group, $R^2$ is a hydrogen atom, an alkyl group, an aralkyl group, a hydroxymethyl group, a carboxymethyl group or an acyloxymethyl group, and $R^3$ is the grouping —XR' (where R' is a hydrogen atom, an alkyl group or an acyl group and X is an oxygen atom or a sulfur atom), a nitro group, an amino group, an alkylamino group, an acylamino group or a halogen atom, with the proviso that when both of $R^1$ and $R^2$ are hydrogen atoms, $R^3$ should not be a hydroxyl group, methoxy group or acetoxy group.

One exemplary compound of formula (VI) is 10-hydroxycamptothecin having the structure shown below:

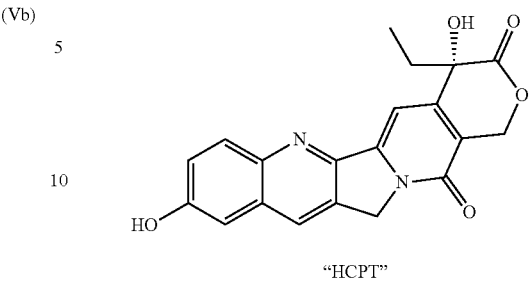

"HCPT"

In another embodiment the compound has a structure according to formula (VII), shown below), which is described in U.S. Pat. No. 4,255,431 to Junggren et al., which is hereby incorporated by reference in its entirety:

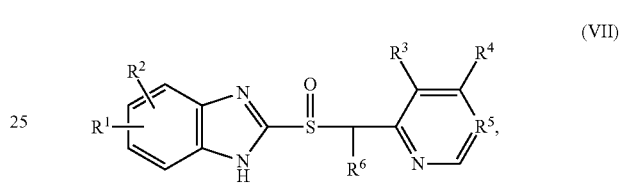

wherein $R^1$ and $R^2$ are same or different and are each selected from the group consisting of hydrogen, alkyl, halogen, carbomethoxy, carbethoxy, alkoxy, and alkanoyl, $R^6$ is selected from the group consisting of hydrogen, methyl, and ethyl, and $R^3$, and $R^5$ are the same or different and are each selected from the group consisting of hydrogen, methyl, methoxy, ethoxy, methoxyethoxy and ethoxyethoxy and $R^4$ is methoxy, ethoxy, methoxyethoxy or ethoxyethoxy whereby $R^3$, $R^4$ and $R^5$ are not all hydrogen, and whereby when two of $R^3$, $R^4$, and $R^5$ are hydrogen, the third of $R^3$, $R^4$ and $R^5$ is not methyl.

Exemplary compounds according to formula (VII) include omeprazole, which is a racemic mixture having the following structure:

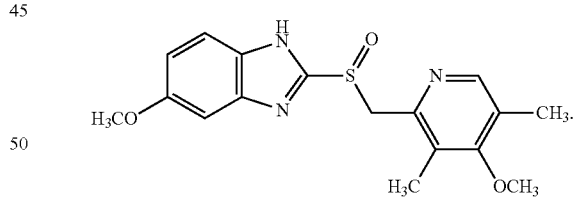

and esomeprazole, which is the substantially purified isomer having the following structure:

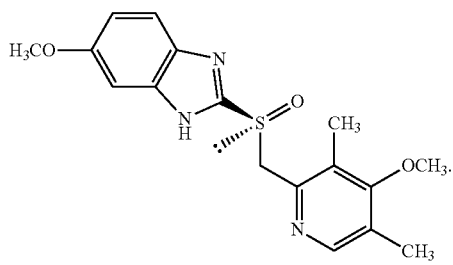

In another embodiment the compound is Flutamide

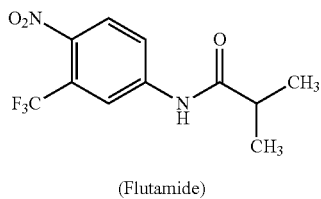 [SMILES: CC(C)C(=O)Nc1ccc([N+](=O)[O-])c(C(F)(F)F)c1]

(Flutamide)

or a derivative thereof having the structure according to formula (VIII), shown below, which is described in U.S. Pat. No. 3,332,768 to Freund et al., which is hereby incorporated by reference in its entirety:

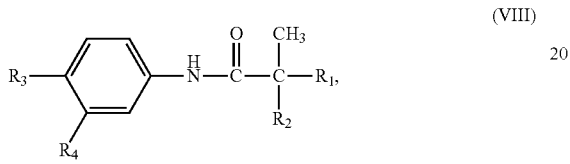

wherein $R_1$ is lower alkyl, $R_2$ is halogen, and $R_3$ and $R_4$ each are hydrogen, halogen, lower alkyl, lower alkoxy, trifluormethyl, or the nitro group.

In a further embodiment the compound has a structure according to formula (IX), shown below, or a pharmaceutically or veterinarily acceptable salt thereof, which is described in PCT Application Publ. No. WO 2014/099837 to Lahm et al., which is hereby incorporated by reference in its entirety:

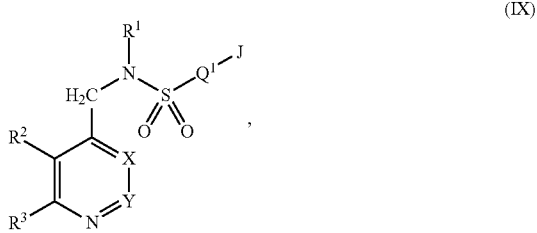

wherein $R^1$ is hydrogen, $C_1$-$C_4$ alkyl, $C_2$-$C_6$ alkylcarbonyl or $C_2$-$C_6$ alkoxycarbonyl;

$R^2$ and $R^3$ are each independently hydrogen, halogen, cyano, hydroxyl, amino, nitro, CHO, $SF_5$, $OR^6$, $NR^{7a}R^{7b}$, $C(O)R^8$, $C(O)OR^9$, $C(O)NR^{10}R^{11}$, $S(O)_pR^{12}$ or $S(O)_2NR^{10}R^{11}$; or $C_1$-$C_6$ alkyl, $C_2$-$C_6$ alkenyl, $C_2$-$C_6$ alkynyl, $C_3$-$C_7$ cycloalkyl, $C_4$-$C_8$ cycloalkylalkyl or $C_5$-$C_7$ cycloalkenyl, each optionally substituted with substituents independently selected from the group consisting of halogen, cyano, nitro, $OR^6$, $NR^{7a}R^{7b}$, $C(O)R^8$, $C(O)OR^9$, $C(O)NR^{10}R^{11}$, $S(O)_pR^{12}$ and $S(O)_2NR^{10}R^{11}$; or G; or $R^2$ and $R^3$ are taken together with the carbons to which they are attached to form a 5- to 6-membered carbocyclic or heterocyclic ring optionally substituted with up to 3 substituents independently selected from $R^{4a}$ on carbon atom ring members and $R^{4b}$ on nitrogen atom ring members;

G is a phenyl ring or an 8- to 10-membered carbocyclic bicyclic ring system, each ring or ring system optionally substituted with up to 5 substituents independently selected from $R^{5a}$; or G is a 5- to 7-membered heterocyclic ring or an 8- to 10-membered heterocyclic bicyclic ring system, each ring or ring system containing ring members selected from carbon atoms and up to 4 heteroatoms independently selected from up to 2 O, up to 2 S and up to 4 N atoms, and optionally substituted with up to 5 substituents independently selected from $R^{5a}$ on carbon atom ring members and $R^{5b}$ on nitrogen atom ring members;

X is $CR^{4c}$ or N;

Y is $CR^{4d}$ or N;

$Q^1$ is 3- to 7-membered carbocyclic ring or an 8- to 10-membered carbocyclic bicyclic ring system, each ring or ring system optionally substituted with up to 5 substituents independently selected from $R^{13a}$; or $Q^1$ is a 5- to 7-membered heterocyclic ring or an 8- to 10-membered heterocyclic bicyclic ring system, each ring or ring system containing ring members selected from carbon atoms and up to 4 heteroatoms independently selected from up to 2 O, up to 2 S and up to 4 N atoms, and optionally substituted with up to 5 substituents independently selected from $R^{13a}$ on carbon atom ring members and $R^{3b}$ on nitrogen atom ring members;

J is hydrogen; or phenyl or naphthalenyl each optionally substituted with up to 5 substituents independently selected from $R^{14a}$; or J is a 5- to 7-membered heterocyclic ring or an 8- to 10-membered heterocyclic bicyclic ring system, each ring or ring system containing ring members selected from carbon atoms and up to 4 heteroatoms independently selected from up to 2 O, up to 2 S and up to 4 N atoms, and optionally substituted with up to 5 substituents independently selected from $R^{14a}$ on carbon atom ring members and $R^{14b}$ on nitrogen atom ring members; or J is L-$Q^2$;

L is O, S, SO, $SO_2$, $NR^5$, $(CH_2)_n$, $OCH_2$, or $CH_2O$;

$Q^2$ is a 3- to 7-membered carbocyclic ring or an 8- to 10-membered carbocyclic bicyclic ring system, each ring or ring system optionally substituted with up to 5 substituents independently selected from $R^{16a}$; or $Q^2$ is a 3- to 7-membered heterocyclic ring or an 8- to 10-membered heterocyclic bicyclic ring system, each ring or ring system containing ring members selected from carbon atoms and up to 4 heteroatoms independently selected from up to 2 O, up to 2 S and up to 4 N atoms, and optionally substituted with up to 5 substituents independently selected from $R^{16a}$ on carbon atom ring members and $R^{16b}$ on nitrogen atom ring members;

each $R^{4a}$ is independently halogen, cyano, hydroxyl, amino, nitro, —CHO, —$SF_5$, $OR^6$, $NR^{7a}R^{7b}$, $C(O)R^8$, $C(O)OR^9$, $C(O)NR^{10}R^{11}$, $S(O)_pR^{12}$ or $S(O)_2NR^{10}R^{11}$; or $C_1$-$C_6$ alkyl, $C_2$-$C_6$ alkenyl, $C_2$-$C_6$ alkynyl, $C_3$-$C_7$ cycloalkyl, $C_4$-$C_8$ cycloalkylalkyl or $C_5$-$C_7$ cycloalkenyl, each optionally substituted with substituents independently selected from the group consisting of halogen, cyano, nitro, $OR^6$, $NR^{7a}R^{7b}$, $C(O)R^8$, $C(O)OR^9$, $C(O)NR^{10}R^{11}$, $S(O)_pR^{12}$ and $S(O)_2NR^{10}R^{11}$; or G;

$R^{4b}$ is cyano, —CHO, $OR^6$, $NR^{7a}R^{7b}$, $C(O)R^8$, $C(O)OR^9$, $C(O)NR^{10}R^{11}$, $S(O)_pR^{12}$ or $S(O)_2NR^{10}R^{11}$; or $C_1$-$C_6$ alkyl, $C_2$-$C_6$ alkenyl, $C_2$-$C_6$ alkynyl, $C_3$-$C_7$ cycloalkyl, $C_4$-$C_8$ cycloalkylalkyl or $C_5$-$C_7$ cycloalkenyl, each optionally substituted with substituents independently selected from the group consisting of halogen, cyano, nitro, $OR^6$, $NR^{7a}R^{7b}$, $C(O)R^8$, $C(O)OR^9$, $C(O)NR^{10}R^{11}$, $S(O)_pR^{12}$ and $S(O)_2NR^{10}R^{11}$; or G;

$R^{4c}$ and $R^{4d}$ are each independently hydrogen, halogen, cyano, hydroxyl, amino, nitro, —CHO, —$SF_5$, $OR^6$, $NR^{7a}R^{7b}$, $C(O)R^8$, $C(O)OR^9$, $C(O)NR^{10}R^{11}$, $S(O)_pR^{12}$ or $S(O)_2NR^{10}R^{11}$; or $C_1$-$C_6$ alkyl, $C_2$-$C_6$ alkenyl, $C_2$-$C_6$ alkynyl, $C_3$-$C_7$ cycloalkyl, $C_4$-$C_8$ cycloalkylalkyl or $C_5$-$C_7$ cycloalkenyl, each optionally substituted with substituents independently selected from the group consisting of halogen, cyano, nitro, $OR^6$, $NR^{7a}R^{7b}$, $C(O)R^8$, $C(O)OR^9$, $C(O)NR^{10}R^{11}$, $S(O)_pR^{12}$ and $S(O)_2NR^{10}R^{11}$; or G;

each $R^{5a}$ is independently halogen, cyano, hydroxyl, amino, nitro, —CHO, —$SF_5$, $OR^6$, $NR^{7a}R^{7b}$, $C(O)R^8$, $C(O)OR^9$, $C(O)NR^{10}R^{11}$, $S(O)_pR^{12}$ or $S(O)_2NR^{10}R^{11}$; or $C_1$-$C_6$ alkyl, $C_2$-$C_6$ alkenyl, $C_2$-$C_6$ alkynyl, $C_3$-$C_7$ cycloalkyl, $C_4$-$C_8$ cycloalkylalkyl or $C_5$-$C_7$ cycloalkenyl, each optionally substituted with substituents independently selected from the group consisting of halogen, cyano, nitro, $OR^6$, $NR^{7a}R^{7b}$, $C(O)R^8$, $C(O)OR^9$, $C(O)NR^{10}R^{11}$, $S(O)_pR^{12}$ and $S(O)_2NR^{10}R^{11}$;

$R^{5b}$ is cyano, —CHO, $OR^6$, $NR^{7a}R^{7b}$, $C(O)R^8$, $C(O)OR^9$, $C(O)NR^{10}R^{11}$, $S(O)_pR^{12}$ or $S(O)_2NR^{10}R^{11}$; or $C_1$-$C_6$ alkyl, $C_2$-$C_6$ alkenyl, $C_2$-$C_6$ alkynyl, $C_3$-$C_7$ cycloalkyl, $C_4$-$C_8$ cycloalkylalkyl or $C_5$-$C_7$ cycloalkenyl, each optionally substituted with substituents independently selected from the group consisting of halogen, cyano, nitro, $OR^6$, $NR^{7a}R^{7b}$, $C(O)R^8$, $C(O)OR^9$, $C(O)NR^{10}R^{11}$, $S(O)_pR^{12}$ and $S(O)_2NR^{10}R_{11}$; each $R^6$ is independently hydrogen, $C_2$-$C_6$ alkylcarbonyl, $C_2$-$C_6$ alkoxycarbonyl, $C_2$-$C_6$ alkylaminocarbonyl, $C_3$-$C_6$ dialkylaminocarbonyl, $C_1$-$C_6$ alkylsulfenyl, $C_1$-$C_6$ alkylsulfinyl, $C_1$-$C_6$ alkylsulfonyl, $C_2$-$C_6$ alkylaminosulfonyl or $C_3$-$C_6$ dialkylaminosulfonyl; or $C_1$-$C_6$ alkyl, $C_2$-$C_6$ alkenyl, $C_2$-$C_6$ alkynyl or benzyl, each optionally substituted with substituents independently selected from the group consisting of halogen, cyano, nitro, $C_1$-$C_6$ alkoxy, $C_1$-$C_6$ alkylamino, $C_2$-$C_8$ dialkylamino, $C_2$-$C_6$ alkylcarbonyl, $C_2$-$C_6$ alkoxycarbonyl, $C_2$-$C_6$ alkylaminocarbonyl, $C_3$-$C_6$ dialkylaminocarbonyl, $C_1$-$C_6$ alkylsulfenyl, $C_1$-$C_6$ alkylsulfinyl, $C_1$-$C_6$ alkylsulfonyl, $C_2$-$C_6$ alkylaminosulfonyl and $C_3$-$C_6$ dialkylaminosulfonyl; or $C_3$-$C_7$ cycloalkyl, $C_4$-$C_8$ cycloalkylalkyl or $C_5$-$C_7$ cycloalkenyl, each optionally substituted with substituents independently selected from the group consisting of halogen, cyano, nitro, $C_1$-$C_4$ alkyl, $C_1$-$C_4$ haloalkyl, $C_1$-$C_4$ alkoxy, $C_1$-$C_4$ alkylsulfenyl, $C_1$-$C_4$ alkylsulfinyl and $C_1$-$C_4$ alkylsulfonyl;

each $R^{7a}$ is independently hydrogen, $C_2$-$C_6$ alkylcarbonyl, $C_2$-$C_6$ alkoxycarbonyl, $C_2$-$C_6$ alkylaminocarbonyl, $C_3$-$C_6$ dialkylaminocarbonyl, $C_1$-$C_6$ alkylsulfenyl, $C_1$-$C_6$ alkylsulfinyl or $C_1$-$C_6$ alkylsulfonyl, $C_2$-$C_6$ alkylaminosulfonyl or $C_3$-$C_6$ dialkylaminosulfonyl; or $C_1$-$C_6$ alkyl, $C_2$-$C_6$ alkenyl, $C_2$-$C_6$ alkynyl or benzyl, each optionally substituted with substituents independently selected from the group consisting of halogen, cyano, nitro, $C_1$-$C_6$ alkoxy, $C_1$-$C_6$ alkylamino, $C_2$-$C_8$ dialkylamino, $C_2$-$C_6$ alkylcarbonyl, $C_2$-$C_6$ alkoxycarbonyl, $C_2$-$C_6$ alkylaminocarbonyl, $C_3$-$C_6$ dialkylaminocarbonyl, $C_1$-$C_6$ alkylsulfenyl, $C_1$-$C_6$ alkylsulfinyl, $C_1$-$C_6$ alkylsulfonyl, $C_2$-$C_6$ alkylaminosulfonyl and $C_3$-$C_6$ dialkylaminosulfonyl; or $C_3$-$C_7$ cycloalkyl, $C_4$-$C_8$ cycloalkylalkyl or $C_5$-$C_7$ cycloalkenyl, each optionally substituted with substituents independently selected from the group consisting of halogen, cyano, nitro, $C_1$-$C_4$ alkyl, $C_1$-$C_4$ haloalkyl, $C_1$-$C_4$ alkoxy, $C_1$-$C_4$ alkylsulfenyl, $C_1$-$C_4$ alkylsulfinyl and $C_1$-$C_4$ alkylsulfonyl;

each $R^{7b}$ is independently hydrogen; or $C_1$-$C_6$ alkyl, $C_2$-$C_6$ alkenyl, $C_2$-$C_6$ alkynyl or benzyl, each optionally substituted with substituents independently selected from the group consisting of halogen, cyano, nitro, $C_1$-$C_6$ alkoxy, $C_1$-$C_6$ alkylamino, $C_2$-$C_8$ dialkylamino, $C_2$-$C_6$ alkylcarbonyl, $C_2$-$C_6$ alkoxycarbonyl, $C_2$-$C_6$ alkylaminocarbonyl, $C_3$-$C_6$ dialkylaminocarbonyl, $C_1$-$C_6$ alkylsulfenyl, $C_1$-$C_6$ alkylsulfinyl, $C_1$-$C_6$ alkylsulfonyl, $C_2$-$C_6$ alkylaminosulfonyl and $C_3$-$C_6$ dialkylaminosulfonyl;

$R^8$, $R^9$, $R^{10}$ and $R^{12}$ are each independently hydrogen; or $C_1$-$C_6$ alkyl, $C_2$-$C_6$ alkenyl, $C_2$-$C_6$ alkynyl, phenyl, benzyl, $C_3$-$C_7$ cycloalkyl, $C_4$-$C_8$ cycloalkylalkyl or $C_5$-$C_7$ cycloalkenyl, each optionally substituted with substituents independently selected from the group consisting of halogen, cyano, nitro, $C_1$-$C_4$ alkyl, $C_1$-$C_4$ haloalkyl, $C_1$-$C_4$ alkoxy, $C_1$-$C_4$ haloalkoxy, $C_2$-$C_6$ alkoxycarbonyl, $C_2$-$C_6$ alkylaminocarbonyl, $C_2$-$C_8$ dialkylaminocarbonyl, $C_1$-$C_4$ alkylsulfenyl, $C_1$-$C_4$ alkylsulfinyl, $C_1$-$C_4$ alkylsulfonyl, $C_1$-$C_4$ haloalkylsulfenyl, $C_1$-$C_4$ haloalkylsulfinyl and $C_1$-$C_4$ haloalkylsulfonyl;

each $R^{11}$ is independently hydrogen; or $C_1$-$C_6$ alkyl, $C_2$-$C_6$ alkenyl, $C_2$-$C_6$ alkynyl or benzyl, each optionally substituted with substituents independently selected from the group consisting of halogen, cyano, nitro, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylsulfenyl, $C_1$-$C_4$ alkylsulfinyl, $C_1$-$C_4$ alkylsulfonyl, $C_1$-$C_4$ haloalkylsulfenyl, $C_1$-$C_4$ haloalkylsulfinyl and $C_1$-$C_4$ haloalkylsulfonyl;

each $R^{13a}$ is independently halogen, cyano, hydroxyl, amino, nitro, —CHO, —$SF_5$, $OR^6$, $NR^{7a}R^{7b}$, $C(O)R^8$, $C(O)OR^9$, $C(O)NR^{10}R^{11}$, $S(O)_pR^2$ or $S(O)_2NR^{10}R^{11}$; or $C_1$-$C_6$ alkyl, $C_2$-$C_6$ alkenyl, $C_2$-$C_6$ alkynyl, $C_3$-$C_7$ cycloalkyl, $C_4$-$C_8$ cycloalkylalkyl or $C_5$-$C_7$ cycloalkenyl, each optionally substituted with substituents independently selected from the group consisting of halogen, cyano, nitro, $OR^6$, $NR^{7a}R^{7b}$, $C(O)R^8$, $C(O)OR^9$, $C(O)NR^{10}R^{11}$, $S(O)_pR^{12}$ and $S(O)_2NR^{10}R^{11}$;

$R^{13b}$ is cyano, —CHO, $OR^6$, $NR^{7a}R^{7b}$, $C(O)R^8$, $C(O)OR^9$, $C(O)NR^{10}R^{11}$, $S(O)_pR^{12}$ or $S(O)_2NR^{10}R^{11}$; or $C_1$-$C_6$ alkyl, $C_2$-$C_6$ alkenyl, $C_2$-$C_6$ alkynyl, $C_3$-$C_7$ cycloalkyl, $C_4$-$C_8$ cycloalkylalkyl or $C_5$-$C_7$ cycloalkenyl, each optionally substituted with substituents independently selected from the group consisting of halogen, cyano, nitro, $OR^6$, $NR^{7a}R^{7b}C(O)R^8$, $C(O)OR^9$, $C(O)NR^{10}R^{11}$, $S(O)_pR^{12}$ and $S(O)_2NR^{10}R^{11}$;

each $R^{14a}$ is independently halogen, cyano, hydroxyl, amino, nitro, —CHO, —$SF_5$, $OR^6$, $NR^{7a}R^{7b}$, $C(O)R^8$, $C(O)OR^9$, $C(O)NR^{10}R^{11}$, $S(O)_pR^{12}$ or $S(O)_2NR^{10}R^{11}$; or $C_1$-$C_6$ alkyl, $C_2$-$C_6$ alkenyl, $C_2$-$C_6$ alkynyl, $C_3$-$C_7$ cycloalkyl, $C_4$-$C_8$ cycloalkylalkyl or $C_5$-$C_7$ cycloalkenyl, each optionally substituted with substituents independently selected from the group consisting of halogen, cyano, nitro, $OR^6$, $NR^{7a}R^{7b}$, $C(O)R^8$, $C(O)OR^9$, $C(O)NR^{10}R^{11}$, $S(O)_pR^{12}$ and $S(O)_2NR^{10}R^{11}$;

$R^{14b}$ is cyano, —CHO, $OR^6$, $NR^{7a}R^{7b}$, $C(O)R^8$, $C(O)OR^9$, $C(O)NR^{10}R^{11}$, $S(O)_pR^{12}$ or $S(O)_2NR^{10}R^{11}$; or $C_1$-$C_6$ alkyl, $C_2$-$C_6$ alkenyl, $C_2$-$C_6$ alkynyl, $C_3$-$C_7$ cycloalkyl, $C_4$-$C_8$ cycloalkylalkyl or $C_5$-$C_7$ cycloalkenyl, each optionally substituted with substituents independently selected from the group consisting of halogen, cyano, nitro, $OR^6$, $NR^{7a}R^{7b}C(O)R^8$, $C(O)OR^9$, $C(O)NR^{10}R^{11}$, $S(O)_pR^{12}$ and $S(O)_2NR^{10}R^{11}$;

$R^{15}$ is hydrogen, cyano, —CHO, $OR^6$, $NR^{7a}R^{7b}$, $C(O)R^8$, $C(O)OR^9$, $C(O)NR^{10}R^{11}$, $S(O)_pR^{12}$ or $S(O)_2NR^{10}R^{11}$; or $C_1$-$C_6$ alkyl, $C_2$-$C_6$ alkenyl, $C_2$-$C_6$ alkynyl, $C_3$-$C_7$ cycloalkyl, $C_4$-$C_8$ cycloalkylalkyl or $C_5$-$C_7$ cycloalkenyl, each optionally substituted with substituents independently selected from the group consisting of halogen, cyano, nitro, OR$^6$, NR$^{7a}$R$^{7b}$C(O)R$^8$, C(O)OR$^9$, C(O)NR$^{10}$R$^{11}$, S(O)$_p$R$^{12}$ and S(O)$_2$NR$^{10}$R$^{11}$;

each R$^{16a}$ is independently halogen, cyano, hydroxyl, amino, nitro, —CHO, —SF$_5$, OR$^6$, NR$^{7a}$R$^{7b}$C(O)R$^8$, C(O)OR$^9$, C(O)NR$^{10}$R$^{11}$, S(O)$_p$R$^{12}$ or S(O)$_2$NR$^{10}$R$^{11}$; or C$_1$-C$_6$ alkyl, C$_2$-C$_6$ alkenyl, C$_2$-C$_6$ alkynyl, C$_3$-C$_7$ cycloalkyl, C$_4$-C$_8$ cycloalkylalkyl or C$_5$-C$_7$ cycloalkenyl, each optionally substituted with substituents independently selected from the group consisting of halogen, cyano, nitro, OR$^6$, NR$^{7a}$R$^{7b}$, C(O)R$^8$, C(O)OR$^9$, C(O)NR$^{10}$R$^{11}$, S(O)$_p$R$^{12}$ and S(O)$_2$NR$^{10}$R$^{11}$; or G;

R$^{16b}$ is cyano, —CHO, OR$^6$, NR$^{7a}$R$^{7b}$, C(O)R$^8$, C(O)OR$^9$, C(O)NR$^{10}$R$^{11}$, S(O)$_p$R$^{12}$ or S(O)$_2$NR$^{10}$R$^{11}$; or C$_1$-C$_6$ alkyl, C$_2$-C$_6$ alkenyl, C$_2$-C$_6$ alkynyl, C$_3$-C$_7$ cycloalkyl, C$_4$-C$_8$ cycloalkylalkyl or C$_5$-C$_7$ cycloalkenyl, each optionally substituted with substituents independently selected from the group consisting of halogen, cyano, nitro, OR$^6$, NR$^{7a}$R$^{7b}$C(O)R$^8$, C(O)OR$^9$, C(O)NR$^{10}$R$^{11}$, S(O)$_p$R$^{12}$ and S(O)$_2$NR$^{11}$; or G;

n is 1 or 2; and p is 0, 1 or 2;

provided that (a) when J is phenyl and Q$^1$ is phenyl, then each R$^{13a}$ is hydrogen; and (b) when L is S, SO, SO$_2$, NR$^{15}$, (CH$_2$)$_n$, OCH$_2$, or CH$_2$O, then Q$^2$ is other than phenyl.

Exemplary compounds according to formula (IX) include, without limitation, those selected from the group of:

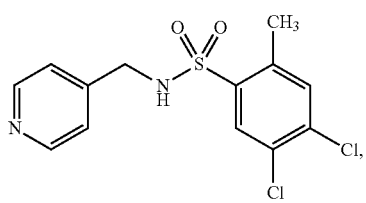

(infra Table 1, C2)

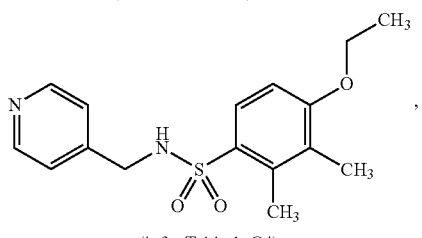

(infra Table 1, C4)

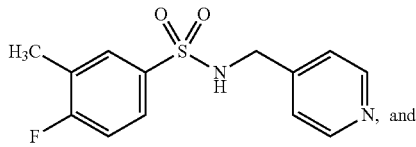

(infra Table 1, A3)

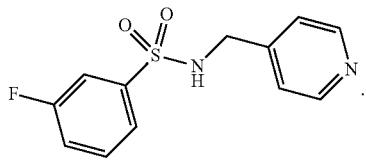

(infra Table 1, B1)

In a further embodiment the compound has the structure

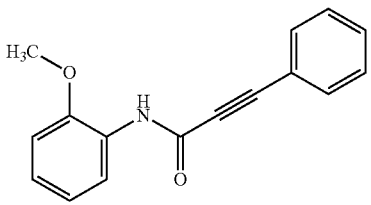

(infra Table 1, C3)

or a derivative thereof having the formula (X), shown below, which is described in U.S. Pat. No. 3,212,900 to Oguchi et al., which is hereby incorporated by reference in its entirety:

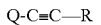  (X), wherein R is hydrogen atom or carboxyl, alkoxycarbonyl, phenyl or substituted phenyl radical, and Q is alkoxycarbonyl, carbamoyl,

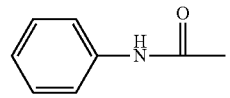

phenyl, substituted phenyl or naphthyl radical, or in case R represents hydrogen atom, Q may be a group of the formula

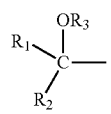

(in which R$_1$ represents hydrogen atom, lower alkyl, phenyl, substituted phenyl or aralkyl radical; R$_2$ represents lower alkyl, phenyl, substituted phenyl, naphthyl or aralkyl radical, or it may, together with the R$_1$, form a cycloalkyl radical; and R$_3$ is hydrogen or acyl radical). Using the procedures described in U.S. Pat. No. 3,212,900 to Oguchi et al., persons of skill in the art will be able to prepare compounds where the group

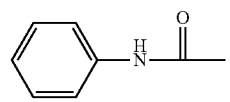

comprises one or more alkyl or alkoxy substituents (i.e., by using the appropriate starting materials).

In another embodiment the compound has the structure

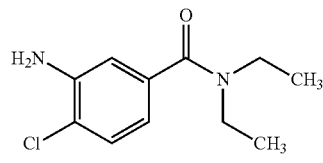

(infra Table 1)

or derivatives thereof having the formula (XI), shown below, which is described in JP 57021320 to Honda Narimitsu et al., which is hereby incorporated by reference in its entirety:

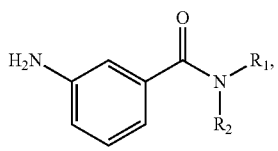

(XI)

wherein $R_1$ and $R_2$ are H, alkyl, (substituted) aralkyl, or (substituted) phenyl. These compounds can be easily prepared by reducing the corresponding m-nitrobenzoic acid amide by conventional methods (JP 57021320 to Honda Narimitsu et al., which is hereby incorporated by reference in its entirety). Using the procedures described in JP 57021320 to Honda Narimitsu et al., persons of skill in the art will be able to prepare compounds bearing an additional halogen substituent on a phenyl ring (i.e., by using the appropriate starting materials).

In one embodiment the compound is a sulfide having the following formula:

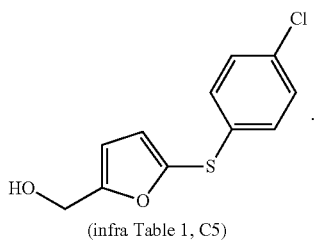 [SMILES: OCc1ccc(Sc2ccc(Cl)cc2)o1]

(infra Table 1, C5)

Alternatively aromatic or heteroaromatic sulfides having the formula R—S—R (XII), wherein R is substituted aryl or substituted heteroaryl can be prepared as described in GB Patent No. 1460559 to Voronkov et al., which is hereby incorporated by reference in its entirety.

In another embodiment the compound has a structure according to formula (XIII), shown below, which is described in U.S. Pat. No. 6,596,726 to Bridges et al., which is hereby incorporated by reference in its entirety:

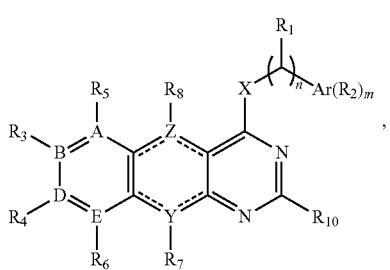

(XIII)

wherein: 1) Y and Z are both C (carbon), both N or one N and the other C, in which case the ring structure is a linearly fused 6,6 (5 or 6) tricycle, or 2) one of Y and Z is C═C, C═N whereupon the other one of Y or Z is simply a bond between the two aromatic rings, then the ring structure is a nonlinear 6,6 (5 or 6) tricycle, or 3) one of Y and Z is N, O or S, whereupon the other one of Y or Z is simply a bond between the two aromatic rings, then the ring structure is a fused 6,5 (5 or 6) tricycle;

A, B, D and E can all be carbon, or up to two of them can be nitrogen, whereupon the remaining atoms must be carbon, or any two contiguous positions in A-E can be a single heteroatom, N, O or S, forming a five membered fused ring, in which case one of the two remaining atoms must be carbon, and the other can be either carbon or nitrogen, except that the case where A and B taken together, and D and E taken separately are all three nitrogen atoms;

X is O, S, NH or $NR^9$, such that $R^9$ is lower alkyl (1-4 carbon atoms), OH, $NH_2$, lower alkoxy (1-4 carbon atoms) or lower monoalkylamino (1-4 carbon atoms);

$R^1$ is H or lower alkyl;

n is 0, 1 or 2;

if n is 2, $R^1$ can be independently H or lower alkyl on either linking carbon atom, and both R and S stereocentres on either linker are included;

$R^2$ is lower alkyl (1-4 carbon atoms), cycloalkyl (3-8 carbon atoms), lower alkoxy (1-4 carbon atoms), cycloalkoxy (3-8 carbon atoms), nitro, halo, lower perfluoroalkyl (1-4 carbon atoms), hydroxy, lower acyloxy (1-4 carbon atoms; —O—C(O)—R), amino, lower mono or dialkylamino (1-4 carbon atoms), lower mono or dicycloalkylamino (3-8 carbon atoms), hydroxymethyl, lower acyl (1-4 carbon atoms; —C(O) R), cyano, lower thioalkyl (1-4 carbon atoms), lower sulfinylalkyl (1-4 carbon atoms), lower sulfonylalkyl (1-4 carbon atoms), thiocycloalkyl (3-8 carbon atoms), sulfinylcycloalkyl (3-8 carbon atoms), sulfonylcycloalkyl (3-8 carbon atoms), mercapto, lower alkoxycarbonyl (1-4 carbon atoms), cycloalkoxycarbonyl (3-8 carbon atoms), lower alkenyl (2-4 carbon atoms), cycloalkenyl (4-8 carbon atoms), lower alkynyl (2-4 carbon atoms), or two $R^2$ taken together can form a carbocyclic ring of 5-7 members; and m is 0-3, wherein Ar is phenyl, thienyl, furanyl, pyrrolyl, pyridyl, pyrimidyl, imidazoyl, pyrazinyl, oxazolyl, thiazolyl, naphthyl, benzothienyl, benzofuranyl, indolyl, quinolinyl, isoquinolinyl and quinazolinyl;

$R^3$, $R^4$, $R^5$ and $R^6$ are independently, not present, H, lower alkyl (1-4 carbon atoms), cycloalkyl (3-8 carbon atoms), lower alkoxy (1-4 carbon atoms), cycloalkoxy (3-8 carbon atoms), hydroxy, lower acyloxy (1-4 carbon atoms), amino, lower mono or dialkylamino (1-4 carbon atoms), lower mono or dicycloalkylamino (3-8 carbon atoms), lower alkyl (1-4 carbon atoms) or cycloalkyl (3-8 carbon atoms), carbonate (—OC(O)OR) where R is alkyl of from 1-4 carbon atoms or cycloalkyl of from 3-8 carbon atoms;

or ureido or thioureido or N or O linked urethane any one of which is optionally substituted by mono or di-lower alkyl (1-4 carbon atoms) or cycloalkyl (3-8 carbon atoms);

lower thioalkyl (1-4 carbon atoms), thiocycloalkyl (3-8 carbon atoms), mercapto, lower alkenyl (2-4 carbon atoms), hydrazino, N- and/or N'-mono- or di lower alkylhydrazino (1-4 carbon atoms), lower acylamino (1-4 carbon atoms), hydroxylamino, N- and/or C-mono- or di lower alkylhydroxylamino (1-4 carbon atoms), or taken together can be methylene-, ethylene- or propylenedioxy, or taken together form a fused pyrrolidine, tetrahydrofuranyl, pipenidinyl, piperazinyl, morpholino or thiomorpholino ring;

$R^7$ and $R^8$ can be independently as appropriate, lone pairs of electrons, H, or lower alkyl;

any lower alkyl group substituent on any of the substituents in $R^3$-$R^8$ which contain such a moiety can be optionally substituted with one or more of hydroxy, amino, lower monoalkylamino, lower dialkylamino, N-pyrrolidyl, N-piperidinyl, N-pyridinium, N-morpholino, N-thiomorpholino or N-piperazino groups;

if one or two of A through E are N, then if any of $R^3$-$R^6$ is on a neighboring C atom to one of the N atoms, that substituent cannot be either OH or SH; and $R^{10}$ is H or lower alkyl (1-4 carbon atoms), amino or lower mono- or dialkylamino (1-4 carbon atoms);

if any of the substitutents $R^1$, $R^2$, $R^3$ or $R^4$ contain chiral centers, or in the case of $R^1$ create chiral centers on the linking atoms, then all stereoisomers thereof both separately and as racemic and/or diastereoisomeric mixtures are included;

or a pharmaceutical salt or hydrate thereof.

For the compounds of formula (XIII), the following provisos are provided:

the ring containing A-E is aromatic;

if A and B taken together and E are nitrogen, and if neither Y nor Z is a heteroatom, and if X=NH, and n=1, and $R^1$=H and Ar=Ph, then one of the imidazole nitrogen atoms must have a substituent from the $R^3$-$R^6$ group other than lone pair or hydrogen;

if A-E are carbon, and Y is a bond, and Z is sulfur, and X=NH, and n=0, then Ar cannot be unsubstituted phenyl, unsubstituted or substituted pyridyl or unsubstituted or substituted pyrimidyl.

For the compounds of formula (XIII), the following additional provisos may apply:

if A-E are carbon, Y and Z cannot be both carbon- or one ethylidene and the other a bond, unless at least one of $R^3$-$R^6$ is not hydrogen;

if A-E are carbon one of Y and Z cannot be nitrogen, substituted with hydrogen, and the other a bond.

An exemplary compound of formula (XIII) has the following structure:

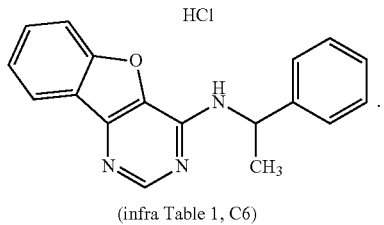 [SMILES: Cl ; CC(Nc1ncnc2c1oc1ccccc12)c1ccccc1]

(infra Table 1, C6)

In yet another embodiment, the compound or active agent is a cinnamoyl compound having a structure of formula (XIV), shown below, which is described in U.S. Patent Application Publication No. US 2009/0143368 to Shiraki et al., which is hereby incorporated by reference in its entirety:

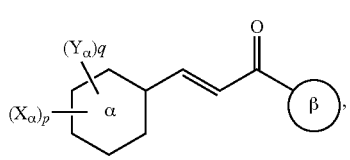

wherein,

I. α represents a benzene ring or a pyridine ring; in $(Y_\alpha)_q$, $Y_\alpha$ is a substituent on a carbon atom and represents a group included in the following $X_0$ group or the $Y_0$ group, q represents 0, 1, 2, 3, 4 or 5, and when q is not less than 2, $Y_\alpha$s are the same or different, and when q is not less than 2, adjacent two same or different $Y_\alpha$s may together form a group included in the $Z_0$ group to be fused to the a ring; and in $(X_\alpha)_p$, $X_\alpha$ is a substituent on a carbon atom and represents a group which does not belong to the following $X_0$ group, $Y_0$ group and $Z_0$ group, p represents 0, 1, 2, 3, 4 or 5, and when p is not less than 2, $X_\alpha$s are the same or different and the sum of p and q is not more than 5;

(1) the $X_0$ group: a $M_\alpha$- group, wherein $M_\alpha$ represents a $R_b$— group (wherein $R_b$ represents a C1-C10 alkyl group optionally substituted with a halogen atom), a halogen atom, a nitro group, a cyano group, a hydroxyl group, a $R_c$—$B_a$—$R_d$— group (wherein $R_c$ represents a C1-C10 alkyl group optionally substituted with a halogen atom, $B_a$ represents an oxy group, a thio group, a sulfinyl group or a sulfonyl group, and $R_d$ represents a single bond or a C1-C10 alkylene group), an HOR$_d$— group (wherein $R_d$ is as defined above), a $R_e$—CO—$R_d$—group (wherein $R_e$ represents a hydrogen atom, or a C1-C10 alkyl group optionally substituted with a halogen atom, and $R_d$ is as defined above), a $R_e$—CO—O—$R_d$— group (wherein $R_e$ and $R_d$ are as defined above), a $R_e$O—CO—$R_d$— group (wherein $R_e$ and $R_d$ are as defined above), an HO—CO—CH=CH— group, a $R_eR_e$'N—$R_d$— group (wherein $R_e$ and $R_e$' are the same or different, $R_e$ is as defined above, $R_e$' has the same meaning as $R_e$ has, and $R_d$ is as defined above), a $R_e$—CO—NR$_e$'—$R_d$— group (wherein $R_e$, $R_e$' and $R_d$ are as defined above), a $R_b$O—CO—N($R_e$)—$R_d$— group (wherein $R_b$, $R_e$ and $R_d$ are as defined above), a $R_eR_e$'N—CO—$R_d$— group (wherein $R_e$, $R_e$' and $R_d$ are as defined above), a $R_eR_e$'N—CO—NR$_e$"—$R_d$— group (wherein $R_e$, $R_e$' and $R_e$" are the same or different, $R_e$, $R_e$' are as defined above, $R_e$" has the same meaning as $R_e$ has, and $R_d$ is as defined above), a $R_eR_e$'N—C(=NR$_e$")—NR$_e$'"-$R_d$— group (wherein $R_e$, $R_e$', $R_e$" and $R_e$'" are the same or different, $R_e$, $R_e$', and $R_e$" are as defined above, $R_e$'" has the same meaning as $R_e$ has, and $R_d$ is as defined above), a $R_b$—SO$_2$—NR$_e$—$R_d$— group (wherein $R_b$, $R_e$ and $R_d$ are as defined above), a $R_eR_e$'N—SO$_2$—$R_d$— group (wherein $R_e$, $R_e$" and $R_d$ are as defined above), a C2-C10 alkenyl group or a $C_2$-$C_{10}$ alkynyl group;

(2) the $Y_0$ group: a $M_{b0}$-$R_d$— group, wherein $M_{b0}$ represents a $M_{c0}$- group

[wherein $M_{c0}$ represents a $M_{d0}$-$R_d$'— group [wherein $M_{do}$ represents a 6 to 10-membered aryl group optionally substituted with a $M_a$- group (wherein $M_a$ is as defined above), a 5 to 10-membered heteroaryl group optionally substituted with a $M_a$- group (wherein $M_a$ is as defined above), a 3 to 10-membered cyclic hydrocarbon or heterocyclic group optionally substituted with a $M_a$- group (wherein $M_a$ is as defined above) and optionally containing an unsaturated bond, a ($b_0$)-group represented by

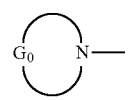

(wherein $G_0$ forms an optionally substituted, saturated or unsaturated, nonaromatic 5 to 14-membered hydrocarbon ring or heterocyclic ring), a ($c_0$)-group represented by

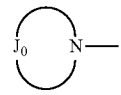

(wherein, $J_0$ forms a 5 to 7-membered aromatic ring optionally containing a nitrogen atom), a ($d_0$)-group represented by

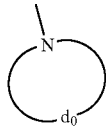
($d_0$)

[wherein $d_0$ forms a 5 to 12-membered hydrocarbon ring which is substituted with a carbonyl group or a thiocarbonyl group and further which may be optionally substituted with an oxy group, a thio group, a —$NR_1$— group {wherein $R_1$ represents a hydrogen atom, or a C1-C10 alkyl group, or a C2-C10 alkyl group substituted with a halogen atom or a $R_2$—B— group (wherein $R_2$ represents a C1-C10 alkyl group, a C3-C10 alkenyl group or a C3-C10 alkynyl group, and $B_1$ represents an oxy group, a thio group, a sulfinyl group or a sulfonyl group), a C3-C10 alkenyl group, or a C3-C10 alkynyl group), a sulfinyl group, or a sulfonyl group], or a ($e_0$)-group represented by

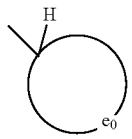
($e_0$)

{wherein $e_0$ forms a 5 to 12-membered hydrocarbon ring optionally substituted with a carbonyl group, a thiocarbonyl group, an oxy group, a thio group, a —$NR_1$— group (wherein $R_1$ is as defined above), a sulfinyl group or a sulfonyl group); and $R_d'$ is the same as or different from $R_d$ and has the same meaning as $R_d$ has], a $M_{c0}$-$B_a$ group (wherein $M_{c0}$ and $B_a$ are as defined above), a $M_{c0}$-CO— group (wherein $M_{c0}$ is as defined above), a $M_{c0}$-CO—O— group (wherein $M_{e0}$ is as defined above), a $M_{c0}$O—CO— group (wherein $M_{c0}$ is as defined above), a $M_{c0}R_eN$— group (wherein $M_{c0}$ and $R_e$ are as defined above), a $M_{c0}$-CO—$NR_e$— group (wherein $M_{c0}$ and $R_e$ are as defined above), a $M_{c0}$O—CO—$NR_e$ group (wherein $M_{c0}$ and $R_e$ are as defined above), a $M_{c0}R_eN$—CO— group (wherein $M_{c0}$ and $R_e$ are as defined above), a $M_{c0}R_eN$—CO—$NR_e'$— group (wherein $M_{c0}$, $R_e$ and $R_e'$ are as defined above), a $M_{c0}R_eN$—C(=$NR_e'$)—$NR_e''$— group (wherein $M_{c0}$, $R_e$, $R_e'$ and $R_e''$ are as defined above), a $M_{c0}$-$SO_2$—$NR_e$— group (wherein $M_{c0}$ and $R_e$ are as defined above) or a $M_{c0}R_eN$—$SO_2$— group (wherein $M_{c0}$ and $R_e$ are as defined above), and $R_d$ is as defined above;

(3) the $Z_0$ group: a 5- to 12-membered hydrocarbon ring or heterocyclic ring which may be substituted with a halogen atom, a C1-C10 alkoxy group, C3-C10 alkenyloxy group, a C3-C10 alkynyloxy group, a carbonyl group, a thiocarbonyl group, an oxy group, a thio group, a sulfinyl group or a sulfonyl group, and which is aromatic or non-aromatic and monocyclic or fused ring and is fused to the a ring; and II. β represents
a group represented by formula (I-1):

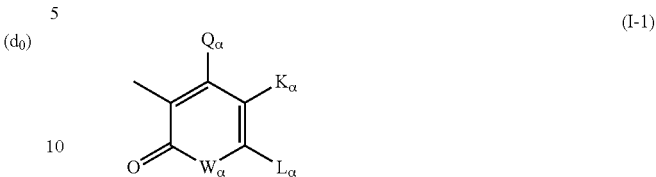

wherein,
(1) $Q_\alpha$ represents an optionally substituted hydroxyl group, or an optionally substituted amino group,
(2) $W_\alpha$ represents an oxygen atom or a —$NT_\alpha$- group (wherein $T_\alpha$ represents a hydrogen atom, or a substituent on the nitrogen atom),
(3) $K_\alpha$ and $L_\alpha$ form a —$V_a$=$V_a'V_a''$=$V_a'''$— group (wherein $V_a$, $V_a'$, $V_a''$ and $V_a'''$ are the same or different, and represent an optionally substituted methine group or a —N= group, and at least one of $V_a$, $V_a'$, $V_a''$ and $V_a'''$ represents a —N= group);

a group represented by formula (I-2):

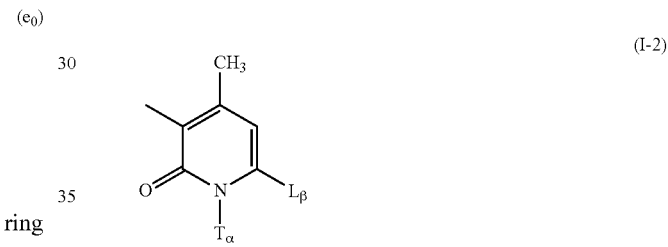

wherein $T_\alpha$ is as defined above, and $L_\beta$ represents a hydroxyl group or a methyl group; a group represented by formula (I-3):

wherein $T_\alpha$ is as defined above, and $L_\gamma$ represents a C1-C10 alkyl group; a group represented by formula (I-4):

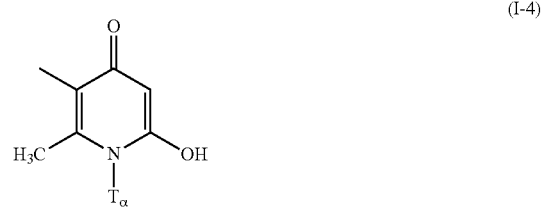

wherein $T_\alpha$ is as defined above; a group represented by formula (I-5):

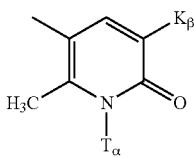

(I-5)

wherein $T_\alpha$ is as defined above, and $K_\beta$ represents a cyano group or a UOCO— group (wherein U represents a hydrogen atom or a C1-C10 alkyl group);

a group represented by formula (I-6):

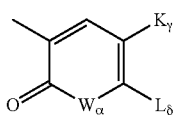

(I-6)

wherein $W_\alpha$ is as defined above, and $K_\gamma$ and $L_\delta$ form an optionally substituted C3-C10 alkylene group or an optionally substituted C4-C10 alkenylene group;

a group represented by formula (I-7):

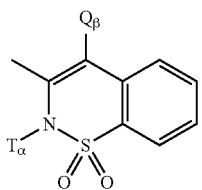

(I-7)

wherein $T_\alpha$ is as defined above, and $Q_\beta$ represents an optionally substituted hydroxyl group; or a group represented by formula (I-8):

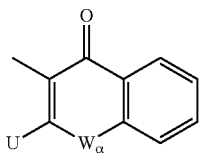

(I-8)

wherein U and $W_\alpha$ are as defined above.

An exemplary compound according to formula (XIV) has the following structure:

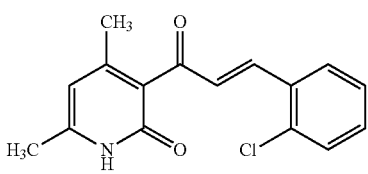

(infra Table 1, A1)

In another embodiment the compound is a 4,5,6,7-tetra-hydrobenzo[b]thiophene compounds having the general structure according to formula (XV), shown below, which is described in U.S. Patent Application Publication No. US2004/0171603 to Pato et al., which is hereby incorporated by reference in its entirety:

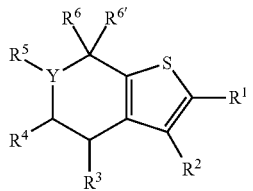

(XV)

wherein

Y represents C or S;

R represents $R^2$, —NH—CO—$R^{16}$, —NH$_2$, —N=CH—$R^5$, —N=CH—$R^{16}$, —NH—CH$_2$—$R^{14}$, —NH—CH$_2$—$R^{16}$, —NH—SO$_2$—$R^{14}$, —NH—CO—NH—$R^{14}$, —NH—CS—NH—CH(CCl$_3$)—NH—CO—$R^{16}$, —NH—CH(CCl$_3$)—NH—CO—$R^{12}$, —NH—CS—NH—$R^{12}$, N=CH—$R^{12}$,

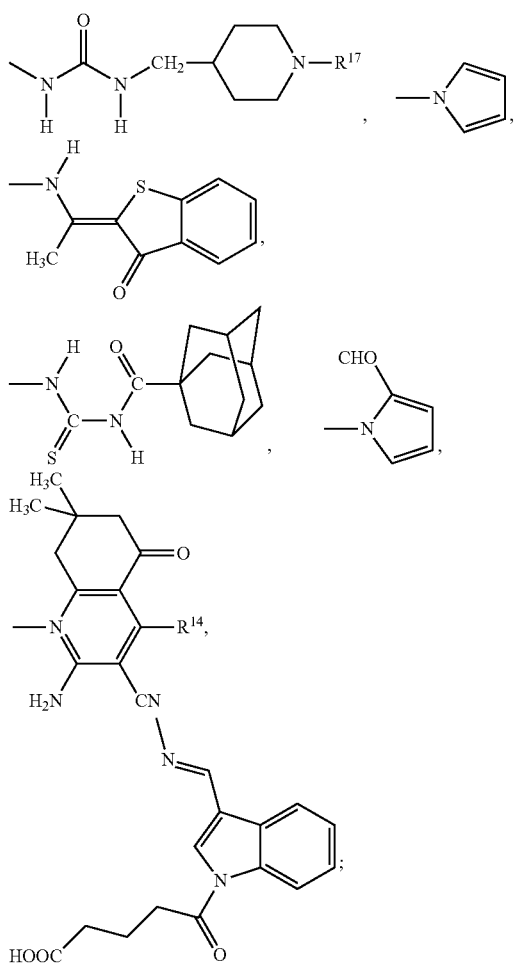

$R^2$ represents —COOR$^{12}$, —CONR$^{12}$R$^{12'}$, —CONR$^{12}$R$^{14}$; —C≡N, —COCOOR$^{12}$, —COCH$_2$Cl, —CO-CONHNH$_2$;

$R^3$, $R^4$, R represent independently of each other —$R^{11}$, $R^{12}$, $R^{12'}$, —OR$^{12}$, —SR$^{12}$, —NO$_2$, —CO—R$^{12}$, —NO, —N$_3$, —CN, —OCN, —NCO, —SCN, —NCS, —COOR$^{12}$, COCN, —CONR$^{12}$R$^{12'}$, —NR$^{12}$R$^{12'}$, —SOR$^{12}$, —SO$_2$R$^{12}$, —SO$_3$R$^{12}$, —CH$_2$OR$^{12}$;

in one case R$^6$ represents —R$^{11}$, —R$^{12}$, R$^{12'}$, —OR$^{12}$, —SR$^{12}$, —NO$_2$, —CO—R$^{12}$, —NO, N$_3$, —CN, —OCN, —NCO, —SCN, —NCS, —COOR$^{12}$, —COCN, —CONR$^{12}$R$^{12'}$, NR$^{12}$R$^{12'}$, —SOR$^2$, —SO$_2$R$^{12}$, —SO$_3$R$^{12}$, and R$^{6'}$ is hydrogen;

in the other case R$^6$ and R$^{6'}$ together represent a carbonyl oxygen or a oximo residue =N—OH or =N—O(O)C—R$^{12}$;

R$^7$, R$^8$, R$^9$, R$^{10}$ represent independently of each other —R$^{11}$, —R$^{12}$, —OR$^{12}$, SR$^{12}$, —NO$_2$, CO—R$^{12}$, —COOR$^{12}$, —OOCR$^{16}$;

R$^{11}$ represents —F, —Cl, —Br, —I;

R$^{12}$, R$^{12'}$ represent independently of each other —H, —CH$_3$, —C(R$^{11}$)$_3$, —C$_2$H$_5$, —C$_3$H$_7$, CH(CH$_3$)$_2$, —CH$_2$—CH=CH$_2$, —CCH$_3$=CH$_2$, —CH=C(CH$_3$)$_2$, —CH=CH—CH$_3$, CH=CHC$_2$H$_5$, —CH(CH$_3$)C$_2$H$_5$, —(CH$_2$)$_n$—C≡C—R$^5$, —C$_4$H$_9$, —C(CH$_3$)$_3$, -Ph, —CH$_2$—R$^{15}$, —C$_2$H$_4$OH with n being an integer from 0-2;

R$^{13}$ represents —CF$_2$CHF$_2$, —C$_5$H$_{11}$, —C$_6$H$_{11}$, —C$_6$H$_{13}$, —C$_7$H$_{15}$, —C$_8$H$_{17}$, —C$_9$H$_{19}$, —C$_{10}$H$_{21}$, —C$_{11}$H$_{23}$, —C$_{12}$H$_{25}$, —C$_{13}$H$_{27}$, —CH$_2$SPh, —CH$_2$R$^{11}$, —C$_2$H$_4$R$^{11}$, —C$_3$H$_6$R$^{11}$, —C$_4$H$_5$R$^{11}$, —C$_2$H$_4$Ph, —CH=CH—COOR$^{12}$, —CH$_2$COOR$^{12}$, —C$_2$H$_4$COOR$^{12}$, —C$_3$H$_6$COOR$^{12}$, CH(Ph)-SPh, —C$_3$H$_5$, —CH$_2$CH(Ph)$_2$, —C$_4$H$_7$, —C$_5$H$_9$, —C(CH$_3$)$_2$CH$_2$R$^{11}$, —CH$_2$CH(CH$_3$)$_2$, —CH(R$^{11}$)Ph, —CH$_2$CH(CH$_3$)CH$_2$C(CH$_3$)$_3$, —CH(C$_2$H$_5$)—C$_4$H$_9$, CH(R$^{11}$)$_2$, —CH(Ph)-C$_2$H$_5$, —CH$_2$C(CH$_3$)$_3$, R$^{14}$ represents

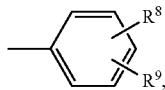

R$^{15}$ represents

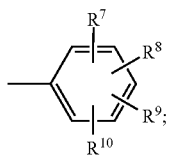

R$^{16}$ is R$^{12}$,

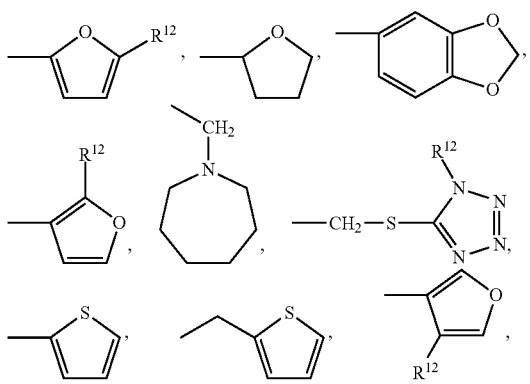

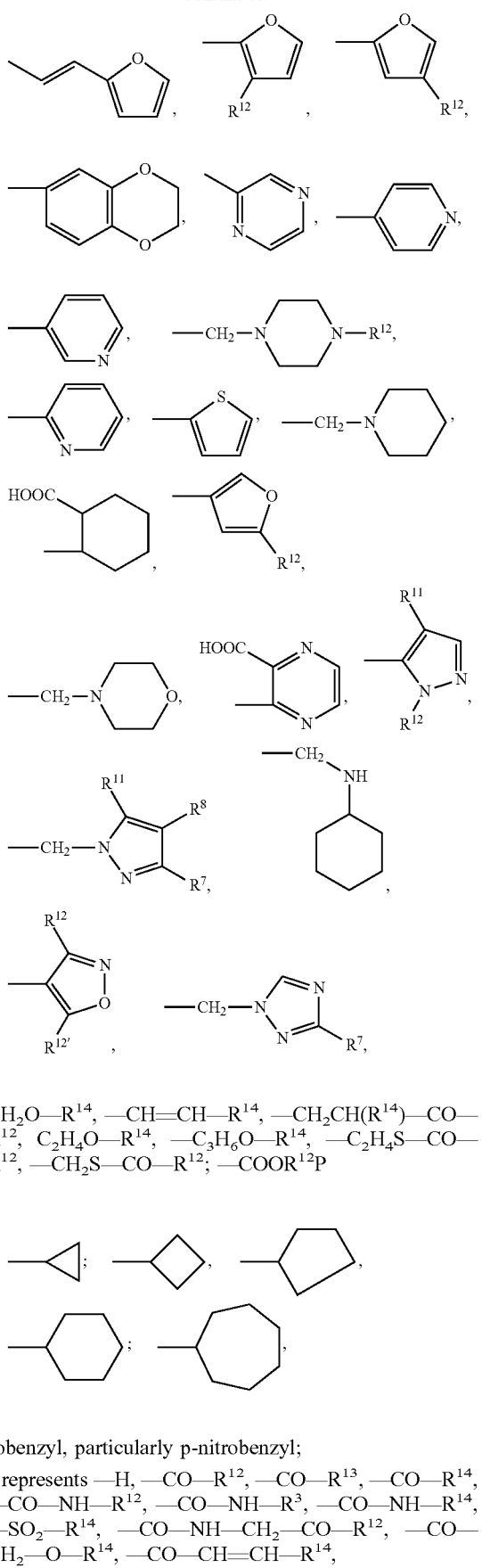

nitrobenzyl, particularly p-nitrobenzyl;

R$^{17}$ represents —H, —CO—R$^{12}$, —CO—R$^{13}$, —CO—R$^{14}$, —CO—NH—R$^{12}$, —CO—NH—R$^3$, —CO—NH—R$^{14}$, —SO$_2$—R$^{14}$, —CO—NH—CH$_2$—CO—R$^{12}$, —CO—CH$_2$—O—R$^{14}$, —CO—CH=CH—R$^{14}$,

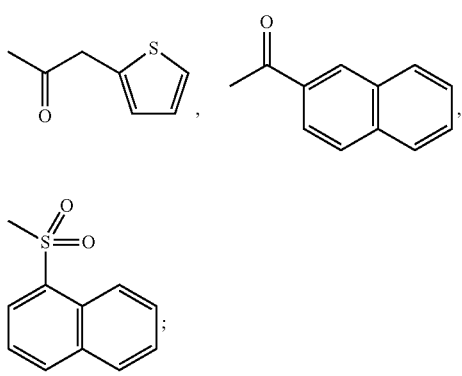

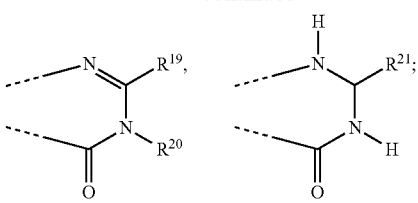

R represents $R^{12}$,

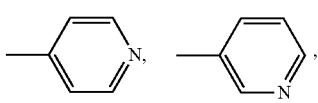

or $R^1$ and $R^2$ together represent a heterocyclic ring system having the following formula

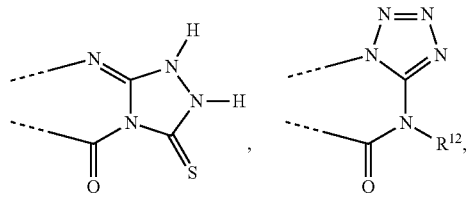

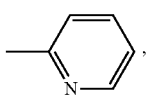

$R^{19}$ represents $R^3$, $R^{14}$, —$SCH_2$—$R^3$, —$SCH_2$—CO—$R^{14}$, —$SCH_2$—CO—NH—$R^{14}$, —$SCH_2$—CO—NH—$CH_2$—$R^{12}$, —NH—CO—$CH_2$—$OR^{14}$, —CO—NH—N=$CHR^{12}(R^{14})$,

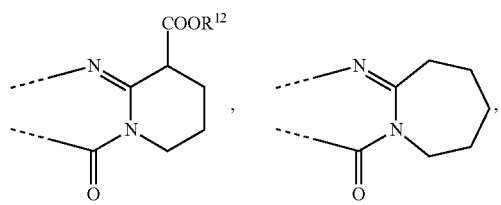

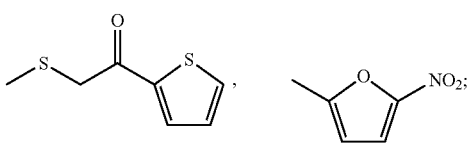

$R^{20}$ represents $R^{12}$, —NH—CO—$R^{12}$, —N=CH—$R^{15}$; $R^{21}$ represents $R^{15}$,

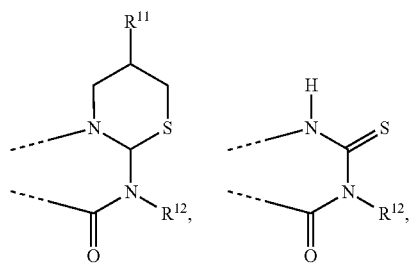

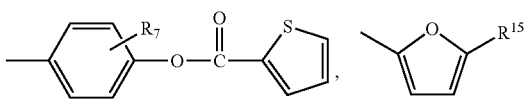

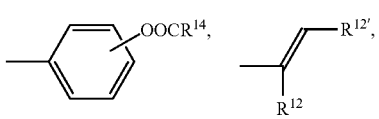

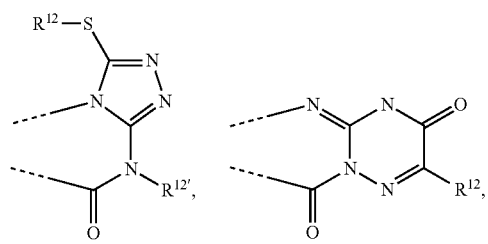

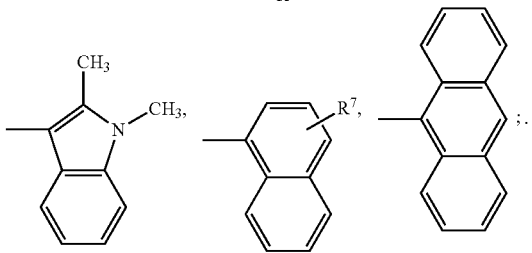

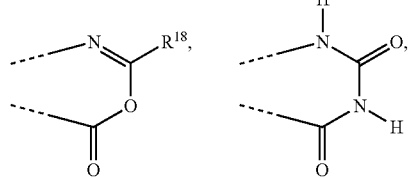

An exemplary compound of formula (XV) includes, without limitation, the following structure:

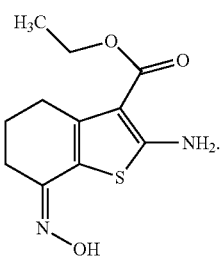

(infra Table 1, A2)

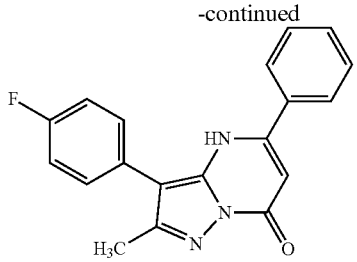

(infra Table 1, A4)

In another embodiment the compound or active agent is a pyrazolo-[1,5a]-pyrimidone compound having the structure according to formula (XVI), shown below, which is described in U.S. Pat. No. 8,796,285 to Zhang et al., which is hereby incorporated by reference in its entirety:

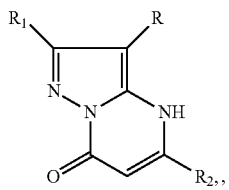

(XVI)

wherein
R is alkyl, aryl, substituted aryl, heterocyclic compound, substituted heterocyclic compound or —COOR$_5$;
R$_1$ is hydrogen, halogen, alkyl, alkyl halide, aryl or substituted aryl;
R$_2$ is halogen, alkyl, substituted alkyl, aryl, substituted aryl, heterocyclic compound, substituted heterocyclic compound, or

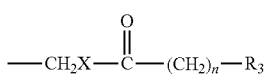

or —CH$_2$R$^4$;
X is O or NH, n is a natural number selected from 0 to 6,
R$_3$ is hydrogen, halogen, aryl or substituted aryl;
R$_4$ is fatty acid or cyclic imine; and
R$_5$ is an alkyl with 1-4 carbon.

Exemplary compounds of formula (XVI) include, without limitation, those selected from the group of:

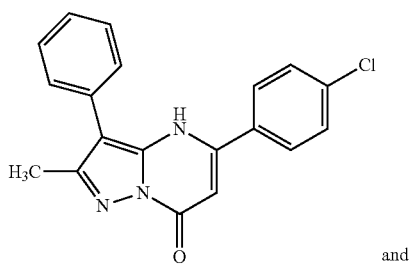

and (infra Table 1, B6)

In another embodiment the compound or active agent has a structure shown below

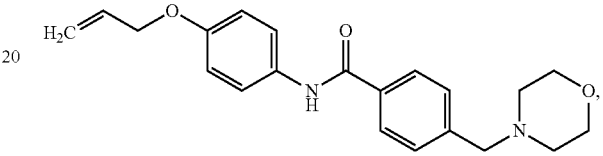

(infra Table 1, A5)

or a derivative thereof represented by formula (XVII), shown below,

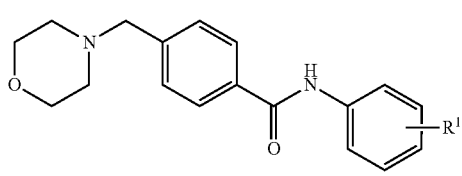

(XVII)

wherein R$^1$ can be H, o-I, m-I, p-I, p-CF3, orp-OMe. These structures of formula (XVII) are described by Nagao et al., "Synthesis and Structure-Activity Relationships of Novel, Potent, Orally Active Hypoxia-Inducible Factor-1 Inhibitors," *Bioorg. Med. Chem.*, 22:5513-5529 (2014), which is hereby incorporated by reference in its entirety. Other O—C$_1$ to C$_6$ hydrocarbon substituents, like those of compound A5, can be similarly synthesized in the manner described in Nagao.

In another embodiment the compound is a 1,4-substituted benzene compound or a pharmaceutically acceptable salt thereof having the following structure of formula XVIII, shown below, which is described in WO 2005103030 to Jiang et al., which is hereby incorporated by reference in its entirety:

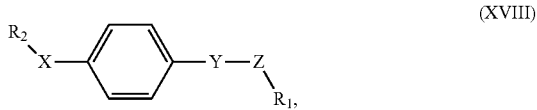

(XVIII)

wherein X, Z are each independently selected from O, S or NH;
Y is selected from CO or SO$_2$;
R$_1$ is selected from hydrogen; C$_1$-C$_6$ alkyl with a straight-chain or branched, alkenyl or alkynyl group; C$_3$-C$_7$ cycloalkyl, cycloalkenyl or cycloalkynyl; aromatic group Ar; contains 1-3 substituents selected from oxygen, 5-7 membered heteroaryl or substituted heteroatom sulfur or nitrogen heteroaryl, wherein heteroaryl with phenyl or 5-7 membered aromatic heterocyclyl group form a fused ring aromatic group, a substituted heteroaryl group substituents independently selected from the group consisting of one or 2-5: halogen; $C_1$-$C_6$ alkyl with straight or branched, alkenyl or alkynyl; cyano; nitro; amino; hydroxy; hydroxy groups; trifluoromethyl; trifluoromethoxy; carboxy; $C_1$-$C_4$ alkoxy; mercapto; $C_1$-$C_4$ acyl; aryl Ar;

$R_2$ is selected from the following structural groups (II, III, IV or V):

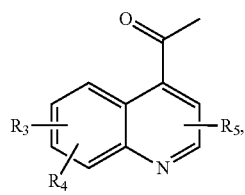

II

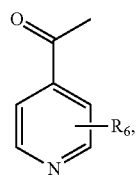

III

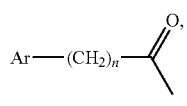

IV

Ar—(CH$_2$)$_n$—

V where, n is 0, 1, 2 or 3;

$R_3$, $R_4$ are each independently selected from hydrogen; $C_1$-$C_6$ linear or branched alkyl, alkenyl or alkynyl group; a nitro group; a halogen; cyano; trifluoromethyl; trifluoromethoxy;

$R_5$, $R_6$ each independently selected from hydrogen; methyl; ethyl; cyclohexyl; aromatic group Ar containing 1 to 3 heteroatoms, 5-7 membered heteroaryl, or a substituted sulfur or nitrogen heteroatoms heteroaryl group, wherein heteroaryl with phenyl or 5-7 membered heterocyclic aromatic group form a fused ring aryl, substituted heteroaryl the substituents are independently selected from the group consisting of one or 2-5: halogen; $C_1$-$C_6$ alkyl, alkenyl or alkynyl group linear or branched; cyano; nitro; amino; hydroxy group; trifluoromethyl; trifluoromethoxy; carboxy; $C_1$-$C_4$ alkoxy group; mercapto; aromatic group Ar; The aromatic group Ar denotes phenyl, naphthyl, biphenyl or a substituted phenyl group, substituted phenyl wherein the substituents are independently selected from the group 1-4: halo; $C_1$-$C_6$ straight-chain or branched-chain alkyl, alkenyl or alkynyl group; cyano; nitro; amino; hydroxy group; trifluoromethyl; trifluoromethoxy; carboxy; $C_1$-$C_4$ alkoxy; mercapto.

One exemplary compound of formula (XVIII) has the following structure:

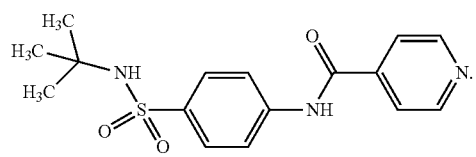

(infra Table 1, B2)

In another embodiment the compound has the structure

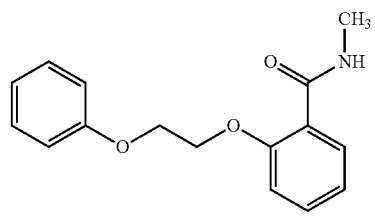

(infra Table 1, B3)

or a derivative thereof. For example a compound having the following structure as described by U.S. Pat. No. 5,041,604 to Saito et al., which is hereby incorporated by reference in its entirety:

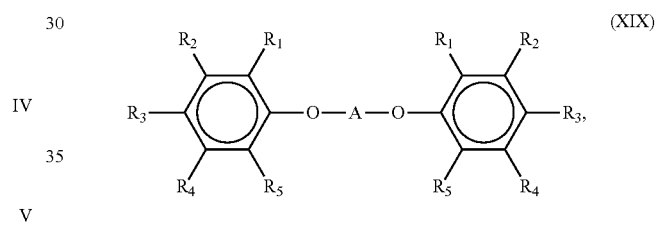

(XIX)

wherein
A is a lower alkylene group, and
$R_1$ to $R_5$ each are the same or different from one another; each represent hydrogen atom, a halogen atom, a lower alkyl group, a lower alkoxy group, a carboxylic acid salt group, an acyl group, cyano group, a cycloalkyl group, an aryl group or nitro group; and may form a ring in conjunction of two adjacent groups. N-alkylbenzamido ring members can be introduced instead of the other substituted phenyl rings.

In another embodiment the compound has the structure

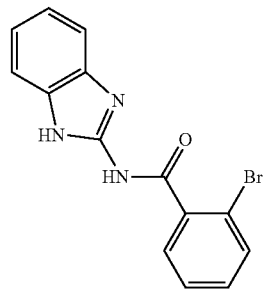

(infra Table 1, B4)

or a derivative thereof having the structure of formula (XX), shown below, which is described in U.S. Pat. No. 3,907,700 to Grier, which is hereby incorporated by reference in its entirety:

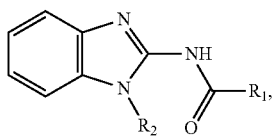

(XX)

wherein R₁ represents an aromatic radical having 1-3 nuclei, including a carbocyclic aryl radical such as phenyl, biphenyl, naphthyl, anthryl, phenanthryl, and the like, and a heterocyclic aryl radical such as furan, thiophene, pyridine, pyridazine, pyrimidine, pyrazine, quinoline, isoquinoline, acridine, phenanthridine, phenazine, phenoxazine, phenthiazine, coumarone, benzothiophene, indole, pyrazole, imidazole, thiazole, oxazole, triazole, carbazole and the like. Specifically excluded from the invention are aliphatic acid amides of 2-aminobenzimidazole (where $R_1$ is alkyl). In addition R, may be attached to the carbonyl through a vinyl group —(CH=CH₂); and R₂ represents hydrogen, alkanoyl, alkenyl, benzoyl, halobenzoyl, alkoxybenzoyl, alkoxycarbonyl, benzoyl, alkyl, phenyl, or aralkyl.

Variants of formula XX can be prepared according to Grier where $R_1$ is a substituted phenyl containing, e.g., a halogen substituent.

In another embodiment the compound of formula (XX) has the following structure, as described in U.S. Pat. No. 7,132,438 to Frenkel et al., which is hereby incorporated by reference in its entirety:

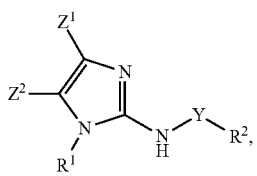

wherein $R^1$ is selected from the group consisting of H, ($C_1$-$C_8$) alkyl, hetero($C_1$-$C_8$)alkyl, fluoro($C_1$-$C_4$)alkyl, cycloalkyl($C_1$-$C_8$)alkyl, heterocyclo($C_1$-$C_8$)alkyl, aryl, aryl($C_1$-$C_8$)alkyl, cyclo($C_3$-$C_8$)alkyl-($C_1$-$C_8$)alkyl, cyclo($C_3$-$C_8$)alkylhetero ($C_1$-$C_8$)alkyl, heterocyclo($C_1$-$C_8$)alkyl, arylhetero($C_1$-$C_8$) alkyl and heteroaryl; $R^2$ is ($C_1$-$C_8$)alkyl, hetero($C_1$-$C_8$) alkyl, perfluoro ($C_1$-$C_4$)alkyl, aryl or heteroaryl;

Y is C(O), S(O)$_m$, S(O)₂NR', C(O)NR', CR³R⁴, C(NR'), C(=CR³R⁴), CR³(OR') or CR³(NR'R"), wherein the subscript m is an integer from 1 to 2;

$Z^1$ and $Z^2$ are independently H, halogen, CN, CO₂R', CONR'R''', ($C_1$-$C_4$)alkyl, ($C_1$-$C_4$)heteroalkyl, perfluoro ($C_1$-$C_4$)alkyl, aryl, heteroaryl, NR'R" or OR¹¹;

alternatively, $Z^1$ and $Z^2$ may be combined to form an additional fused 5-, 6-, 7- or 8-membered cycloalkane, heterocycloalkane, aromatic or heteroaromatic ring;

R³ and R⁴ are independently selected from the group consisting of H, CN, CO₂R', CONR'R''', ($C_1$-$C_4$)alkyl, ($C_1$-$C_4$)heteroalkyl, aryl, heteroaryl, NR'R" and OR';

R' and R¹¹ are independently H, ($C_1$-$C_4$)alkyl, hetero($C_1$-$C_4$)alkyl, aryl or aryl($C_1$-$C_4$)alkyl;

alternatively, when R' and R¹¹ are attached to nitrogen, R' and R¹¹ may be combined with the nitrogen atom to form a 5-, 6- or 7-membered ring; and alternatively, when Y is CR³R⁴, C(NR'), C(=CR³R⁴), CR³(OR') or CR³(NR'R"), R³, R⁴ or R' may be combined with R² to form a 5-, 6-, 7- or 8-membered ring containing from 0 to 3 heteroatoms selected from the group consisting of O, N, Si and S; with the proviso that $R^1$ is not 3-(dialkylamino)propyl when Y is C(O) and $Z^1$ and $Z^2$ are combined to form an additional fused benzene ring.

In another embodiment the compound has the formula

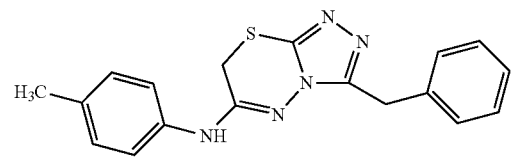

(infra Table 1, B5)

or a derivative thereof having the structure according to formula (XXI), shown below, which is described in JP Patent Publ. No. H 02145588 to Miura Akaio et al., which is hereby incorporated by reference in its entirety:

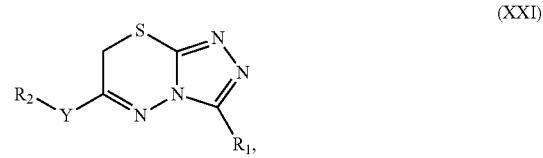

(XXI)

wherein

R₁ represents H or monovalent organic group;

Y represents —O—, —S—, —SO—, —SO₂—, —N(R₃)—;

R₂ and R₃ represent H or monovalent organic group.

Compounds of formula (XXI) can be easily prepared using the method described in by Miura Akaio et al.

In another embodiment, derivatives of compound B5 have the structure of formula (XXII), shown below, which is described in Karthikeyan et al., "Synthesis and antimicrobial studies of novel dichlorophenyl containing aminotriazolothiadiazines," Eur. J. Med. Chem. 43:309-314 (2008), which is hereby incorporated by reference in its entirety

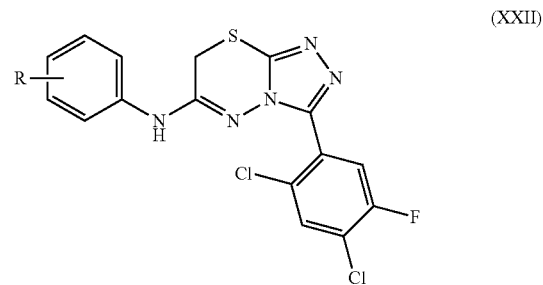

(XXII)

wherein R is selected from the group consisting of 4-CH₃; 4-Cl; 4-OCH₃; 4-OC₂H₅; 4-F, 2,3-Cl₂; 2,4-Cl₂; 2,6-Cl₂; 2,3-(CH₃)₂; 2,4-(CH₃)₂; 2,6-(CH₃)₂; 3-Cl-4-F; 2,4,6-(CH₃)₃; and 2,4,5- Cl₃; 2-CF₃.

In another embodiment the compound or active agent has the structure according to formula (XXIII), shown below, which is described in EP 0289879 to Okada et al., which is hereby incorporated by reference in its entirety):

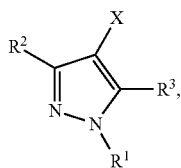

(XXIII)

wherein
$R^1$ represents hydrogen atom, $C_1$-$C_4$ alkyl group, $C_1$-$C_4$ haloalkyl group, phenyl group or benzyl group;
one of $R^2$ and $R^3$ represents —C(O)—$R^4$ or —C(S)—$R^4$;
wherein $R^4$ represents

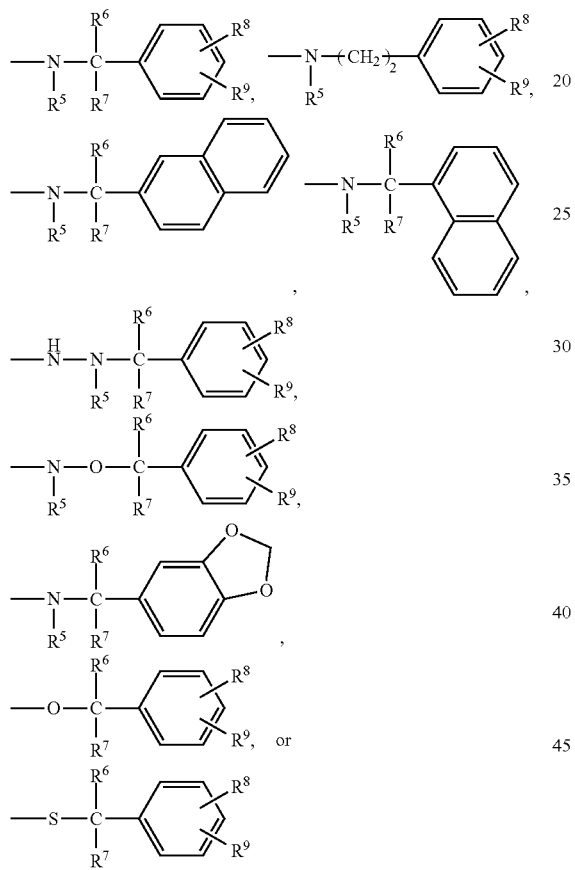

wherein $R^5$, $R^6$ and $R^7$ represent respectively hydrogen atom, $C_1$-$C_4$ alkyl group or phenyl group;
$R^8$ and $R^9$ represent respectively hydrogen atom, halogen atom, $C_1$-$C_8$ alkyl group, $C_3$-$C_5$ alkenyl group, $C_3$-$C_5$ alkynyl group, $C_3$-$C_6$ cycloalkyl group, $C_2$-$C_4$ alkoxyalkyl group, $C_1$-$C_4$ alkoxy group, $C_1$-$C_4$ haloalkoxy group, nitro group, trifluoromethyl group, phenyl group, benzyl group, phenoxy group, benzyloxy group, amino group, $C_1$-$C_4$ alkylamino group, $C_2$-$C_8$ dialkylamino group, cyano group, carboxyl group, $C_2$-$C_5$ alkoxycarbonyl group, $C_4$-$C_7$ cycloalkoxycarbonyl group, $C_3$-$C_9$ alkoxyalkoxycarbonyl group, $C_2$-$C_6$ alkylaminocarbonyl group, $C_3$-$C_{11}$ dialkylaminocarbonyl group, piperidinocarbonyl group, morpholinocarbonyl group, trimethylsilyl group, $C_1$-$C_4$ alkylthio group, $C_1$-$C_4$ alkylsulfinyl group, or $C_1$-$C_4$ alkylsulfonyl group;
providing that if all of $R^6$, $R^7$, $R^8$ and $R^9$ represent hydrogen atoms, $R^1$ represents $C_1$-$C_4$ alkyl group, $C_1$-$C_4$ haloalkyl group, phenyl group or benzyl group;
the other of $R^2$ and $R^3$ represents hydrogen atom, $C_1$-$C_4$ alkyl group, $C_1$-$C_4$ haloalkyl group, $C_3$-$C_6$ cycloalkyl group or phenyl group;
X represents hydrogen atom, halogen atom, $C_1$-$C_4$ alkyl group, nitro group, cyano group, $C_1$-$C_5$ alkylamino group, $C_2$-$C_{10}$ dialkylamino group and $C_2$-$C_7$ acylamino group.
One exemplary compound of formula (XXIII) has the structure of:

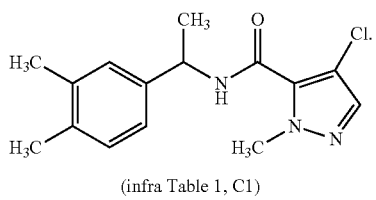

(infra Table 1, C1)

In another embodiment the compound or active agent has a structure according to formula (XXIV), shown below, which is described in U.S. Pat. No. 8,609,663 to Finberg et al., which is hereby incorporated by reference in its entirety:

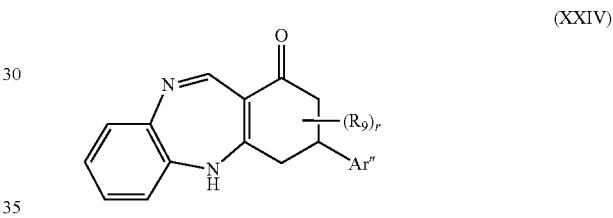

(XXIV)

or a pharmaceutically acceptable salt thereof;
wherein:
Ar" is $C_{6-10}$ aryl or $C_{1-9}$ heteroaryl, each of which is optionally substituted by 1, 2, 3, or 4 independently selected $R'$ groups;
each $R^9$ is independently selected from halogen, cyano, nitro, carboxy, hydroxyl, $C_{1-6}$ alkylcarbonyl, $C_{1-6}$ alkoxycarbonyl, $C_{1-6}$ alkyl, $C_{2-6}$ alkenyl, $C_{2-6}$ alkynyl, $C_{1-6}$ haloalkyl, $C_{1-6}$ alkoxy, and $C_{1-6}$ haloalkoxy;
each $R'$ is independently selected from halogen, cyano, nitro, carboxy, hydroxyl, $C_{1-6}$ alkylcarbonyl, $C_{1-6}$ alkoxycarbonyl, amino, $C_{1-6}$ alkylamino, di-$C_{1-6}$ alkylamino, $C_{1-6}$ alkylsulfonyl, $C_{1-6}$ alkyl, $C_{2-6}$ alkenyl, $C_{2-6}$ alkynyl, $C_{1-6}$ haloalkyl, $C_{1-6}$ alkoxy, and $C_{1-6}$ haloalkoxy; and
r is an integer selected from 0, 1, 2, 3, 4, 5, and 6.
For compounds in which a variable appears more than once, each variable can be a different moiety independently selected from the group defining the variable. For example, where a structure is described having two R groups that are simultaneously present on the same compound, the two R groups can represent different moieties independently selected from the group defined for R. In another example, when an optionally multiple substituent is designated in the form:

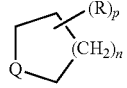

then it is understood that substituent R can occur p number of times on the ring, and R can be a different moiety at each occurrence. It is understood that each R group may replace both of the (CH$_2$)n hydrogen atoms. Further, in the above example, should the variable Q be defined to include hydrogens, such as when Q is the to be CH2, NH, etc., any floating substituent such as R in the above example, can replace a hydrogen of the Q variable as well as a hydrogen in any other non-variable component of the ring. Unless otherwise indicated, should floating substituent R appear on a fused ring system, the substituent may replace a hydrogen atom at any ring atom in the fused ring system.

One exemplary compound of formula (XXIV) has the following structure:

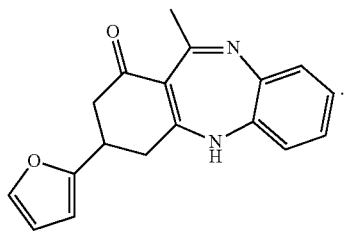

(infra Table 1)

As used above, and throughout the description herein, the following terms, unless otherwise indicated, shall be understood to have the following meanings. If not defined otherwise herein, all technical and scientific terms used herein have the same meaning as is commonly understood by one of ordinary skill in the art to which this technology belongs. In the event that there is a plurality of definitions for a term herein, those in this section prevail unless stated otherwise.

Specific definitions for the substituents mentioned in the compounds formulae (I) to (XXIV) can be the same definitions described in the references cited above for each of formulae (I) to (XXIV). However, commonly understand definitions include those presented below.

The term "alkyl" means an aliphatic hydrocarbon group which may be straight or branched. When not otherwise restricted, the term refers to an alkyl of 20 or fewer carbons. Lower alkyl refers to alkyl groups having about 1 to about 6 carbon atoms in the chain. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl, and the like.

The term "alkenyl" means an aliphatic hydrocarbon group containing a carbon-carbon double bond and which may be straight or branched having about 2 to about 6 carbon atoms in the chain. Particular alkenyl groups have 2 to about 4 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl. The term "alkenyl" may also refer to a hydrocarbon chain having 2 to 6 carbons containing at least one double bond and at least one triple bond.

The term "alkynyl" means an aliphatic hydrocarbon group containing a carbon-carbon triple bond and which may be straight or branched having about 2 to about 6 carbon atoms in the chain. Particular alkynyl groups have 2 to about 4 carbon atoms in the chain. Branched means that one or more lower alkyl groups such as methyl, ethyl, or propyl are attached to a linear alkynyl chain. Exemplary alkynyl groups include ethynyl, propynyl, n-butynyl, 2-butynyl, 3-methylbutynyl, and n-pentynyl.

The term "cycloalkyl" means a non-aromatic, saturated or unsaturated, mono- or multi-cyclic ring system of about 3 to about 7 carbon atoms, or of about 5 to about 7 carbon atoms, and which may include at least one double bond. Exemplary cycloalkyl groups include, without limitation, cyclopropyl, cyclobutyl, cyclopentyl, cyclohexyl, cycloheptyl, cyclopropenyl, cyclobutenyl, cyclopentenyl, cyclophenyl, anti-bicyclopropane, and syn-tricyclopropane.

The term "cycloalkylalkyl" means a cycloalkyl-alkylgroup in which the cycloalkyl and alkyl are as defined herein. Exemplary cycloalkylalkyl groups include cyclopropylmethyl and cyclopentylmethyl. The alkyl radical and the cycloalkyl radical may be optionally substituted as defined herein.

As used herein, "heterocyclyl" or "heterocycle" refers to a stable 3- to 18-membered ring (radical) which consists of carbon atoms and from one to five heteroatoms selected from the group consisting of nitrogen, oxygen, and sulfur. For purposes of this application, the heterocycle may be a monocyclic, or a polycyclic ring system, which may include fused, bridged, or spiro ring systems; and the nitrogen, carbon, or sulfur atoms in the heterocycle may be optionally oxidized; the nitrogen atom may be optionally quaternized; and the ring may be partially or fully saturated. Examples of such heterocycles include, without limitation, azepinyl, azocanyl, pyranyl dioxanyl, dithianyl, 1,3-dioxolanyl, tetrahydrofuryl, dihydropyrrolidinyl, decahydroisoquinolyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, 2-oxoazepinyl, oxazolidinyl, oxiranyl, piperidinyl, piperazinyl, 4-piperidonyl, pyrrolidinyl, pyrazolidinyl, thiazolidinyl, tetrahydropyranyl, thiamorpholinyl, thiamorpholinyl sulfoxide, and thiamorpholinyl sulfone. Further heterocycles and heteroaryls are described in Katritzky et al., eds., Comprehensive Heterocyclic Chemistry: The Structure, Reactions, Synthesis and Use of Heterocyclic Compounds, Vol. 1-8, Pergamon Press, N.Y. (1984), which is hereby incorporated by reference in its entirety.

The term "monocyclic" used herein indicates a molecular structure having one ring.

The term "polycyclic" or "multi-cyclic" used herein indicates a molecular structure having two or more rings, including, but not limited to, fused, bridged, or spiro rings.

The term "aryl" means an aromatic monocyclic or multi-cyclic (polycyclic) ring system of 6 to about 19 carbon atoms, or of 6 to about 10 carbon atoms, and includes arylalkyl groups. The ring system of the aryl group may be optionally substituted. Representative aryl groups include, but are not limited to, groups such as phenyl, naphthyl, azulenyl, phenanthrenyl, anthracenyl, fluorenyl, pyrenyl, triphenylenyl, chrysenyl, and naphthacenyl.

The term "heteroaryl" means an aromatic monocyclic or multi-cyclic ring system of about 5 to about 19 ring atoms, or about 5 to about 10 ring atoms, in which one or more of the atoms in the ring system is/are element(s) other than carbon, for example, nitrogen, oxygen, or sulfur. In the case of multi-cyclic ring system, only one of the rings needs to be aromatic for the ring system to be defined as "heteroaryl". Particular heteroaryls contain about 5 to 6 ring atoms. The prefix aza, oxa, thia, or thio before heteroaryl means that at least a nitrogen, oxygen, or sulfur atom, respectively, is present as a ring atom. A nitrogen, carbon, or sulfur atom in the heteroaryl ring may be optionally oxidized; the nitrogen may optionally be quaternized. Representative heteroaryls include pyridyl, 2-oxo-pyridinyl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, 2-oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, and the like.

The terms "arylalkyl" and "heteroarylalkyl" mean an alkyl substituted with one or more aryl or heteroaryl groups, wherein the alkyl, aryl, and heteroaryl groups are as herein described. One particular example is an arylmethyl or heteroarylmethyl group, in which a single carbon spacer unit is attached to an aryl or heteroaryl group, where the carbon spacer and the aryl or heteroaryl group can be optionally substituted as described herein.

As used herein, the term "acyl" means a moiety of formula R-carbonyl, where R is an alkyl, cycloalkyl, aryl, or heteroaryl as defined above. Exemplary acyl groups include formyl, acetyl, propanoyl, benzoyl, and propenoyl.

The term "carbonyl" means a carbonyl group, —C(O)—.

The term "thiocarbonyl" means a thiocarbonyl group, —C(S)—.

The term "sulfoxide" means a sulfoxide group, —S(O)—.

The term "sulfone" means a sulfone group, —S(O)$_2$—.

The term "alkoxy" means groups of from 1 to 8 carbon atoms of a straight, branched, or cyclic configuration and combinations thereof attached to the parent structure through an oxygen. Examples include methoxy, ethoxy, propoxy, isopropoxy, cyclopropyloxy, cyclohexyloxy, and the like. Lower-alkoxy refers to groups containing one to four carbons. For the purposes of the present patent application, alkoxy also includes methylenedioxy and ethylenedioxy in which each oxygen atom is bonded to the atom, chain, or ring from which the methylenedioxy or ethylenedioxy group is pendant so as to form a ring. Thus, for example, phenyl substituted by alkoxy may be, for example,

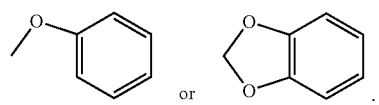

The term "halogen" means fluoro, chloro, bromo, or iodo.
The term "phenyl" means a phenyl group as shown below

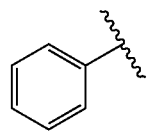

The term "benzyl" means a benzyl group as shown below

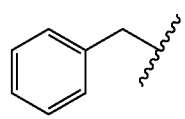

The term "naphthyl" means a naphthyl group as shown below

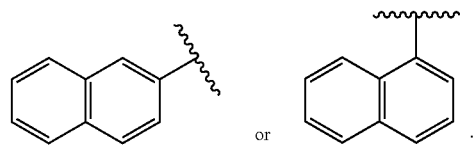 [SMILES: *c1ccc2ccccc2c1 ; *c1cccc2ccccc12]

The term "haloalkyl" means both branched and straight-chain alkyl substituted with one or more halogen, wherein the alkyl group is as herein described.

The term "alkoxyalkyl" means both branched and straight-chain alkyl substituted with one or more alkoxy groups, wherein the alkyl group is as herein described.

The term "optionally substituted" is used to indicate that a group may have a substituent at each substitutable atom of the group (including more than one substituent on a single atom), provided that the designated atom's normal valency is not exceeded and the identity of each substituent is independent of the others. Up to three H atoms in each residue are replaced with alkyl, halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy. "Unsubstituted" atoms bear all of the hydrogen atoms dictated by their valency. When a substituent is keto (i.e., =O), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The terms "compound," "product compound," "active agents" and equivalent expressions are meant to embrace the polyether antibiotics disclosed herein, compounds of formulae (I)-(XXIV) as described herein, as well as any other compounds identified herein (e.g., those compounds identified in the Examples or Table 1). Also contemplated are the prodrugs, the pharmaceutically acceptable salts, the oxides, the solvates, e.g. hydrates, and inclusion complexes of that compound, where the context so permits, as well as any stereoisomeric form, or a mixture of any such forms of that compound in any ratio. Inclusion complexes are described in Remington, *The Science and Practice of Pharmacy*, 19th Ed.

1:176-177 (1995), which is hereby incorporated by reference in its entirety. The most commonly employed inclusion complexes are those with cyclodextrins, and all cyclodextrin complexes, natural and synthetic, are specifically encompassed within the claims. In accordance with some embodiments, a compound as described herein, including in the contexts of pharmaceutical compositions, methods of treatment, and compounds per se, is provided as the salt form. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

The term "pharmaceutical composition" means a composition comprising at least one compound disclosed herein, as well as combinations thereof, and at least one component comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. As used herein, the term "pharmaceutically acceptable carrier" is used to mean any carrier, diluent, adjuvant, excipient, or vehicle, as described herein. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monosterate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgment, suitable for use in contact with the cells of humans and lower animals without undue toxicity, irritation, allergic response and the like, and are commensurate with a reasonable benefit/risk ratio.

The term "pharmaceutically acceptable dosage forms" means dosage forms of the compounds described herein, and includes, for example, tablets, dragees, powders, elixirs, syrups, liquid preparations, including suspensions, sprays, inhalants tablets, lozenges, emulsions, solutions, granules, capsules, and suppositories, as well as liquid preparations for injections, including liposome preparations. Techniques and formulations generally may be found in Remington's Pharmaceutical Sciences, Mack Publishing Co., Easton, Pa., latest edition, which is hereby incorporated by reference in its entirety.

The term "pharmaceutically acceptable salt" refers to salts prepared from pharmaceutically acceptable non-toxic acids or bases including inorganic acids and bases and organic acids and bases. Suitable pharmaceutically acceptable acid addition salts for the compounds described herein include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds described herein include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine), and procaine. Pharmaceutically acceptable salts include, but are not limited to, amine salts, such as but not limited to N, N'dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine, and tris (hydroxymethyl) aminomethane; alkali metal salts, such as but not limited to lithium, potassium, and sodium; alkali earth metal salts, such as but not limited to barium, calcium, and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, cycloalkyl and heterocyclyl esters of acidic groups, including, but not limited to, carboxylic acids, phosphoric acids, phosphinic acids, sulfonic acids, sulfinic acids, and boronic acids. Pharmaceutical acceptable enol ethers include, but are not limited to, derivatives of formula C=C (OR) where R is hydrogen, alkyl, alkenyl, alkynyl, aryl, heteroaryl, cycloalkyl, or heterocyclyl. Pharmaceutically acceptable enol esters include, but are not limited to, derivatives of formula C=C(OC(O)R) where R is hydrogen, alkyl, alkenyl, alkynyl, aryl, heteroaryl, cycloalkyl, or heterocyclyl. Pharmaceutical acceptable solvates and hydrates are complexes of a compound with one or more solvent or water molecules, or 1 to about 100, or 1 to about 10, or one to about 2, 3 or 4, solvent or water molecules.

The term "solvate" refers to a compound described herein in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

The term "therapeutically effective amount" is meant to describe an amount of compound described herein effective in producing the desired therapeutic effect. Such amounts generally vary according to a number of factors well within the purview of ordinarily skilled artisans given the description provided herein to determine and account for. These include, without limitation: the particular subject, as well as its age, weight, height, general physical condition, and medical history, the particular compound used, as well as the carrier in which it is formulated and the route of administration selected for it; and, the nature and severity of the condition being treated.

Compounds described herein may contain one or more asymmetric centers and may thus give rise to enantiomers, diastereomers, and other stereoisomeric forms. Each chiral center may be defined, in terms of absolute stereochemistry, as (R)- or (S)-. This technology is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

This technology also envisions the "quaternization" of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

In the characterization of some of the substituents, it is recited that certain substituents may combine to form rings. Unless stated otherwise, it is intended that such rings may exhibit various degrees of unsaturation (from fully saturated to fully unsaturated), may include heteroatoms and may be substituted with lower alkyl or alkoxy.

The active agents can be administered to an individual in the form of a pharmaceutically acceptable dosage unit that includes an effective amount of the active agent and a pharmaceutically acceptable carrier. Typically, the active agent will be administered to a mammal as a pharmaceutical formulation that includes the active agent and any pharmaceutically acceptable suitable adjuvants, carriers, excipients, and/or stabilizers, and can be in solid or liquid form, such as tablets, capsules, powders, solutions, suspensions, or emulsions. The compositions preferably contain from about 0.01 to about 99 weight percent, more preferably from about 2 to about 60 weight percent, of active agent together with the adjuvants, carriers, and/or excipients. The amount of active agent in such therapeutically useful compositions is such that a suitable dosage unit will be obtained.

The dosage of the active agent is preferably administered at a dose of between about 0.01 mg per kg of body weight per day (mg/kg/day) to about 100 mg/kg/day, preferably 0.01 mg per kg of body weight per day (mg/kg/day) to 10 mg/kg/day, and most preferably 0.1 to 5.0 mg/kg/day.

Administration can be accomplished either via systemic administration to the subject, administration directly to a fibrotic tissue site, or via targeted administration to affected cells. Exemplary routes of administration include, without limitation, orally, parenterally, periadventitially, subcutaneously, intravenously, intramuscularly, intraperitoneally, by inhalation, by intranasal instillation, by implantation, by intracavitary or intravesical instillation, intraocularly, intraarterially, intralesionally, transdermally, intradermally or by application to mucous membranes. Other suitable modes of delivery can also be used, and administration can be repeated periodically as needed.

As persons of skill will recognize, optimization of dosage amount and frequency can be carried out to maximize the efficacy of treatment in accordance with the present invention.

The active agent may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active agents may be incorporated with excipients and used in the form of tablets, capsules, elixirs, suspensions, syrups, and the like. Such compositions and preparations should contain at least 0.1% of the agent. The percentage of the active agent in these compositions may, of course, be varied and may conveniently be between about 2% to about 60% of the weight of the unit. The amount of the active agent in such therapeutically useful compositions is such that a suitable dosage will be obtained.

The tablets, capsules, and the like may also contain a binder such as gum tragacanth, acacia, corn starch, or gelatin; excipients such as dicalcium phosphate; a disintegrating agent such as corn starch, potato starch, or alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient(s), sucrose as a sweetening agent, methyl and propylparabens as preservatives, a dye, and flavoring such as cherry or orange flavor.

The active agent may also be administered parenterally. Solutions or suspensions of the active agent can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The active agent may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

As another alternative, the active agent may be administered to the airways in the form of a lung surfactant formulation. The lung surfactant formulation can include exogenous lung surfactant formulations (e.g., INFASURF® (Forest Laboratories), SURVANTA® (Ross Products), and CUROSURF® (DEY, California, USA) or synthetic lung surfactant formulations (e.g., Exosurf (GlaxoWellcome Inc.), ALEC, and those described in U.S. Application Publ. Nos. 20100055164 and 20150125515, both to Notter et al., each of which is hereby incorporated by reference in its entirety). These surfactant formulations are typically administered via airway instillation (i.e., after intubation) or intratracheally.

According to a further alternative, ophthalmic solutions, suspensions, ointments or inserts comprising an active agent can be administered. Eye drops can be prepared by dissolving the active ingredient in a sterile aqueous solution such as physiological saline, buffering solution, etc., or by combining powder compositions to be dissolved before use. Other vehicles can be chosen, as is known in the art, including but not limited to: balance salt solution, saline solution, water soluble polyethers such as polyethyene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. If desired, additives ordinarily used in the eye drops can be added. Such additives include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, cross-linked polyacrylate, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art).

The active agents may also be administered directly to the targeted tissue. Additionally and/or alternatively, the active agents may be administered to a non-targeted area along with one or more agents that facilitate migration of the active agent to (and/or uptake by) a targeted tissue, organ, or cell. As will be apparent to one of ordinary skill in the art, the therapeutic agent itself can be modified to facilitate its transport to (and uptake by) the desired tissue, organ, or cell.

By way of example, targeted delivery to the liver can be achieved using cationic solid lipid nanoparticles of Kong et al. ("Cationic solid lipid nanoparticles derived from apolipoprotein-free LDLs for target specific systemic treatment of liver fibrosis," *Biomaterials* 34(2):542-51 (2012), which is hereby incorporated by reference in its entirety) modified to deliver the active agents.

Exemplary delivery devices include, without limitation, nebulizers, atomizers, liposomes, transdermal patches, implants, implantable or injectable protein depot compositions, syringes, and gene therapy. Other delivery systems which are known to those of skill in the art can also be employed to achieve the desired delivery of the therapeutic agent to the desired organ, tissue, or cells in vivo to carry out this aspect of the present invention.

In one embodiment, the method of treating fibrosis includes administering to the patient an amount of a second agent that is therapeutically effective to treat the fibrosis (i.e., additional anti-fibrotic agents), wherein the second agent is different from the active agent disclosed above.

Exemplary second agents (additional anti-fibrotic agents) include, without limitation, calcium channel blockers, cytotoxic agents, cytokines, chemokines, integrins, growth factors, hormones, lysophosphatidic acid (LPA) receptor 1 antagonists, agents that modulate the TGF-$\beta$ pathway, endothelin receptor antagonists, agents that reduce connective tissue growth factor (CTGF) activity, matrix metalloproteinase (MMP) inhibitors, agents that reduce the activity of platelet-derived growth factor (PDGF), agents that interfere with integrin function, agents that interfere with the pro-fibrotic activities of cytokines, agents that reduce oxidative stress, PDE4 inhibitors, PDE5 inhibitors, mTor inhibitors, modifiers of the arachidonic acid pathway, peroxisome proliferator-activated receptor (PPAR)-$\gamma$ agonists, kinase inhibitors, inhibitors of VEGF signaling pathway, matrix metalloproteinases, tissue inhibitors of metalloproteinases (TIMPs), HGF agonists, angiotensin-converting enzyme (ACE) inhibitors, angiotensin receptor antagonists, inhibitors of advanced glycation endproducts (AGEs) or their receptors (RAGEs), Rho kinase inhibitors, PKC inhibitors, ADAM-10 inhibitor, farnesoid X receptor agonists, caspase inhibitors, anti-oxidants, inhibitors of collagen expression, LMW heparin or heparin analogs, copper chelators, TNF-$\alpha$ blocking agents, agents that inhibit fibronectin deposition and/or enhance fibronectin degradation and turnover (e.g., bacterial adhesin peptides, fibronectin-derived peptides, and antibodies against fibronectin, as described in U.S. Appl. Publ. No. 20130190224 to Sottile et al., which is hereby incorporated by reference in its entirety), HMG-CoA reductase inhibitors, Thy-1 (CD90) inhibitors, and LDH inhibitors of the type described in co-pending U.S. application Ser. No. 14/718,933 filed on May 21, 2015, which is hereby incorporated by reference in its entirety.

Exemplary calcium channel blockers include, without limitation, Verapamil.

Exemplary cytotoxic agents include, without limitation, azathioprine, methotrexate, and cyclophosphamide. In certain embodiments, these agents can be excluded.

Exemplary cytokines include, without limitation, interleukins such as IL-1, IL-4, IL-5, IL-6, IL-8, IL-10, IL-12, and IL-13; interferons such as interferon-$\gamma$; lymphokines; tumor necrosis factor-$\alpha$; endothelin-1; angiotensin II; leptins; angiogenin(s); monocyte chemoattractant protein type 1 (MCP-1); and macrophage inflammatory protein (MIP-1$\alpha$, MIP-2).

Exemplary chemokines include, without limitation, CCL2, CCL12, CXCL12, CXCR4, CCR3, CCR5, CCR7, and SLC/CCL21.

Exemplary integrins include, without limitation, $\alpha_1\beta_1$, $\alpha_2\beta_1$, $\alpha_v\beta_6$, and $\alpha_v\beta_3$.

Exemplary growth factors include, without limitation, insulin growth factors (IGF-1, IGF-2), keratinocyte growth factor (KGF), hepatocyte growth factor (HGF), fibroblast growth factors (FGF-1, 2 and 4), platelet-derived growth factors (PDGF-AB, PDGF-BB, PDGF-AA), epidermal growth factors (EGFs), transforming growth factors (TGF-$\beta$1-3), osteoid-inducing factor (OIF), bone morphogenic proteins (BMPs; BMP1, BMP2, BMP2A, BMP2B, BMP3, BMP3b, BMP4, BMP5, BMP6, BMP9-BMP-15, OP-1, OP-2, OP-3, BMP-7, HBGF-1, HBGF-2), growth differentiation factors (GDF1-3 and GDF5-12), osteogenic proteins (OP-1, OP-2, OP-3), cartilage-derived morphogenic proteins (CDMP-1, CDMP-2, CDMP-3), colony stimulating factors (CSF-1, G-CSF and GM-CSF or isoforms thereof), vascular endothelial growth factor (VEGF), connective tissue growth factor (CTGF), and neural epidermal growth factor-like 1 (NELL-1).

Exemplary hormones include, without limitation, progesterone, estrogen, testosterone, growth hormone, thyroid hormone, and parathyroid hormone.

Exemplary lysophosphatidic acid (LPA) receptor 1 antagonists include, without limitation, AM152 (Amira Pharmaceuticals), AM966, and Ki16198.

Exemplary agents that modulate TGF-β pathways include, without limitation, $\alpha_v\beta_6$ inhibitors; HGF; rBMP7 (bone morphogenic protein 7); decorin; tyrosine kinase inhibitors (Imantinib, Desatinib, Nolitinib); and agents that that reduce TGF-β activity (e.g., metelimumab (CAT-192), GC-1008 (Genzyme/Medimmune), lerdelimumab (CAT-152), LY-2157299 (Eli Lilly), and ACU-HTR-028 (Opko Health)); antibodies that target one or more TGF-β isoforms; inhibitors of TGF-β receptor kinases (e.g., TGFBR1 (ALK5) and TGFBR2); modulators of post-receptor signaling pathways; and chemokine receptor signaling.

Exemplary endothelin receptor antagonists (including inhibitors that target both endothelin receptor A and B and those that selectively target endothelin receptor A) include, without limitation, ambrisentan; avosentan; bosentan; clazosentan; darusentan; BQ-153; FR-139317, L-744453; macitentan; PD-145065; PD-156252; PD163610; PS-433540; S-0139; sitaxentan sodium; TBC-3711; and zibotentan.

Exemplary agents that reduce the activity of connective tissue growth factor (CTGF) include, without limitation, FG-3019, FibroGen, other CTGF-neutralizing antibodies.

Exemplary matrix metalloproteinase (MMP) inhibitors include, without limitation, MMPI-12, PUP-1 and tigapotide triflutate.

Exemplary agents that reduce the activity of platelet derived growth factor (PDGF) include, without limitation, Imatinib mesylate (Novartis)) and PDGF neutralizing antibodies, antibodies targeting PDGF receptor (PDGFR), inhibitors of PDGFR kinase activity, and post-receptor signaling pathways. PDGFR inhibitors include, but are not limited to, SU9518, CP-673,451 and CP-868596.

Exemplary agents that interfere with integrin function include, without limitation, STX-100, IMGN-388, and integrin targeted antibodies.

Exemplary agents that interfere with the pro-fibrotic activities of cytokines (such as interleukins, e.g., IL4 and IL-13) include, without limitation, AER-001, AMG-317, APG-201, sIL-4Rα, anrukinzumab, CAT-354, cintredekin besudotox, MK-6105, QAX-576, SB-313, SL-102, and TNX-650; as well as neutralizing antibodies to either cytokine, antibodies that target IL-4 receptor or IL-13 receptor, the soluble form of IL-4 receptor or derivatives thereof that is reported to bind and neutralize both IL-4 and IL-13, chimeric proteins including all or part of IL-13 and a toxin particularly *pseudomonas* endotoxin, signaling though the JAK-STAT kinase pathway.

Exemplary agents that interfere with epithelial mesenchymal transition include, without limitation, inhibitors of mTor (including but not limited to rapamycin, 40-O-(2-hydroxy)-ethyl-rapamycin, 32-deoxorapamycin, 40-[3-hydroxy-2-(hydroxy-methyl)-2-methylpropanoate]-rapamycin, Ridaforolimus (AP-23573 or MK-8669) and Torisel (temsirolimus).

Exemplary agents that reduce oxidative stress include, without limitation, N-acetylcysteine (a cysteine pro-drug), tetrathiomolybdate, and interferon-γ.

Exemplary agents that are inhibitors of phosphodiesterase 4 (PDE4) or phosphodiesterase 5 (PDE5) include, without limitation, Roflumilast, mirodenafil, PF-4480682, sildenafil citrate, SLx-2101, tadalafil, udenafil, UK-369003, vardenafil, and zaprinast.

Exemplary modifiers of the arachidonic acid pathway include, with limitation, cyclooxygenase (COX) and 5-lipoxygenase (LO) inhibitors such as Zileuton.

Exemplary compounds that reduce tissue remodeling during fibrosis include, without limitation, prolyl hydrolase inhibitors such as 1016548, CG-0089, FG-2216, FG-4497, FG-5615, FG-6513, fibrostatin A (Takeda), lufironil, P-1894B, and safironil.

Exemplary PPAR-gamma agonists include, without limitation, pioglitazone (Takeda), farglitizar (GSK) and rosiglitazone (GSK).

Exemplary kinase inhibitors include, without limitation, MEK inhibitors (e.g., PD325901, ARRY-142886, ARRY-438162 and PD98059); EGFR inhibitors (e.g., Iressa™ (gefitinib, AstraZeneca), Tarceva™ (erlotinib or OSI-774, OSI Pharmaceuticals Inc.), Erbitux™ (cetuximab, Imclone Pharmaceuticals, Inc.), EMD-7200 (Merck AG), ABX-EGF (Amgen Inc. and Abgenix Inc.), HR3 (Cuban Government), IgA antibodies (University of Erlangen-Nuremberg), TP-38 (IVAX), EGFR fusion protein, EGF-vaccine, anti-EGFR immunoliposomes (Hermes Biosciences Inc.) and combinations thereof, antibodies targeting EGF receptor, inhibitors of EGF receptor kinase, and modulators of post-receptor signaling pathways); ErbB2 receptor inhibitors (e.g., CP-724-714, CI-1033 (canertinib), Herceptin™ (trastuzumab), Omnitarg™ (2C4, petuzumab), TAK-165, GW-572016 (Ionafarnib), GW-282974, EKB-569, PI-166, dHER2 (HER2 Vaccine), APC8024 (HER2 Vaccine), anti-HER/2neu bispecific antibody, B7.her2IgG3, AS HER2 trifunctional bispecific antibodies, mAB AR-209 and mAB 2B-1); IGFIR antibodies (e.g., those described in PCT Application Publ. No. WO 2002/053596, which is hereby incorporated by reference in its entirety); AXL inhibitors (e.g., SGI-AXL-277 (SuperGen) as well as inhibitors disclosed in U.S. Pat. Pub. 20050186571, which is hereby incorporated by reference in its entirety); p38 inhibitors (e.g., SB202190, SB203580 and pyridinyl imidazoles); FGFR inhibitors (e.g., PD 17034, PD166866, and SU5402); TIE2 inhibitors (e.g., those described in Kissau, L. et. al., *J Med Chem.*, 46:2917-2931 (2003), which is hereby incorporated by reference in its entirety); the following kinase inhibitors: Pan ERBB receptor inhibitors (e.g., GW572016, CI-1033, EKB-569, and Omnitarg), MP371 (SuperGen) which is an inhibitor of c-Kit, Ret, PDGFR, and Lck, as well as the non-receptor tyrosine kinase c-src, MP470 (SuperGen) which is an inhibitor of c-Kit, PDGFR, and c-Met, Imatinib (Gleevec™) which is an inhibitor of c-kit, PDGFR, and ROR, as well as the non-receptor tyrosine kinase bcl/abl, Lapatinib (Tykerb™) which is an epidermal growth factor receptor (EGFR) and ERBB2 (Her2/neu) dual tyrosine kinase inhibitor, inhibitors of PDGFR and VEGFR (e.g., Nexavar™ (sorafenib, BAY43-9006), Sutent™ (sunitinib, SU11248), and ABT-869), inhibitors of VEGFR and (e.g., Zactima™ (vandetanib, ZD-6474), BMS-690514 which is a reversible oral inhibitor of epidermal growth factor receptor (EGFR/HER-1), HER-2 and -4, and vascular endothelial growth factor receptors (VEGFRs)-1 to -3, BIBF-1120 which is a receptor kinase inhibitor for VEGF, FGF and PDGF; inhibitors of the VEGF signaling pathway (e.g., PTC-299, INGN-241, oral tetrathiomolybdate, 2-methoxyestradiol, 2-methoxyestradiol nanocrystal dispersion, bevasiranib sodium, PTC-299, Veglin, VEGF neutralizing antibodies, soluble form of VEGFR1 (sFlt) and derivatives thereof which neutralize VEGF, anti-KDR antibodies, VEGFR1 (Fltl) antibodies (e.g., icrucumab (IMC-18F1)), VEGFR2 (KDR) antibodies (e.g., CDP-791 or IMC-1121B (ramucirumab) and VEGFR3 antibodies (e.g., mF4-31C1 from Imclone Systems) and CT-322 (Angiocept™; a VEGFR2 inhibitor), VEGF inhibitors (e.g., bevacizumab (Avastin™), pegaptanib, ranibizumab, NEOVASTAT™, AE-941, VEGF Trap, and PI-88), and VEGF receptor antagonists (e.g., JNJ-17029259 (4-[4-(1-Amino-1-methylethyl)phenyl]-2-[4-(2-morpholin-4-yl-ethyl)phenylamino] pyrimidine-5-carbonitrile (a VEGF-R2 inhibitor)), PTK-787/ZK222584 (Astra-Zeneca), SU5416, SU11248 (Pfizer), ZD6474 ([N-(4-bromo-2-fluorophenyl)-6-methoxy-7-[(1-methylpiperidin-4-yl)methoxy]quinazolin-4-amine]), vandetanib, cediranib, AG-013958, CP-547632, E-7080 (lenvatinib), XL-184, L-21649, ZK-304709, SU6668, sorafenib, sunitinib, pazopanib, vatalanib, AEE-788, AMG-706 (motesanib), axitinib, BIBF-1120, SU-14813, XL-647, XL-999, ABT-869, BAY-57-9352, BAY-73-4506 (regorafinib), BMS-582664, CEP-7055, CHIR-265, OSI-930, TKI-258, fenretinide, and squalamine).

Suitable matrix degrading enzymes include those described in U.S. Application Publ. Nos. 20100003237 and 20120101325, each of which is hereby incorporated by reference in its entirety. Exemplary matrix degrading enzymes include, without limitation, pancreatic elastase, elastase-2a, elastase-2b, neutrophil elastase, proteinase-3, endogenous vascular elastase, cathepsin G, mast cell chymase, mast cell tryptase, plasmin, thrombin, granzyme B, cathepsin S, cathepsin K, cathepsin L, cathepsin B, cathespin C, cathepsin H, cathespin F, cathepsin G, cathepsin O, cathepsin R, cathepsin V (cathepsin 12), cathepsin W, calpain 1, calpain 2, legumain, cathepsin Z (cathepsin X), cathepsin D, cathepsin E, chondroitinase ABC, chondroitinase AC, hyaluronidase, chymopapain, chymotrypsin, collagenase, papain, subtilisin, subtilisin A, heparanase. and matrix metalloproteinases, such as for example, MMP-1 (collagenase-1), MMP-2 (gelatinase A), MMP-3 (stromelysin-1), MMP-7 (matrilysin; PUMP1), MMP-8 (collagenase-2), MMP-9 (gelatinase B), MMP-10 (stromelysin-2), MMP-11 (stromelysin-3), MMP-12 (metalloelastase), MMP-13 (collagenase-3), MMP-14 (MT1-MMP), MMP-15 (MT2-MMP), MMP-16 (MT3-MMP), MMP-17 (MT4-MMP), MMP-18 (collagenase-4), MMP-19 (stromelysin-4), MMP-20 (enamelysin), MMP-21 (x-MMP), MMP-23A (MT5-MMP), MMP-23B, MMP-24 (MT5-MMP), MMP-25 (MT6-MMP), MMP-26 (matrilysin-2), MMP-27 (MMP-22; c-MMP), MMP-28 (epilysin), ADAMTS-1, ADAMTS-2, ADAMTS-3, ADAMTS-4 (aggrecanase-1), ADAMTS-5 (aggrecanase-2), ADAMTS-14.

Exemplary tissue inhibitors of matrix-metalloproteinases (TIMPs) include, without limitation, TIMP-1, TIMP-2, TIMP-3, and TIMP-4.

Exemplary HGF agonists include, without limitation, Refanalin (Angion Biomedica).

Exemplary ACE inhibitors include, without limitation, Alacepril, Benazepril, Captopril, Cilazapril, Ceronapril, Delapril, Enalapril, Enalaprilat, Fosinopril, Fosinoprilat, Imidapril, Lisinopril, Moexipril, Perindopril, Perindoprilat, Quinapril, Quinaprilat, Ramipril, saralasin acetate, spirapril, temocapril, trandolapril, fasidotrilat, beclometasone dipropionate, FPL-66564, Idrapril, MDL-100240, and S-5590.

Exemplary angiotensin receptor antagonists include, without limitation, Candesartan, Irbesartan, Losartan, Valsartan, Telmisartan, and Eprosartan.

Exemplary advanced glycation endproducts (AGEs) inhibitors include, without limitation, Pyridoxamine (Biostratum). Examples of AGE receptors (RAGE) inhibitors include, without limitation, TTP-488 (Transtech Pharma) and TTP-4000 (Transtech Pharma).

Exemplary Rho kinase inhibitors include, without limitation, GSK269962, GSK429286, AS1892802, SB772077B, and SR3677.

Exemplary PKC inhibitors include, without limitation, Ruboxistaurin mesilate hydrate (Lilly).

Exemplary ADAM-10 inhibitors include, without limitation, XL-784 (Exelixis).

Exemplary farnesoid X receptor agonists include, without limitation, INT-747 (Intercept Pharmaceuticals).

Exemplary caspase inhibitors include, without limitation, PF-3491390 (Pfizer, formally IDN-6556), and LB84318 (LG Life Sciences).

Exemplary anti-oxidants include, without limitation, Heptax (Hawaii Biotech), N-acetylcysteine (Pierre Fabre), tocopherol, silymarin, and Sho-saiko-To (H-09).

Exemplary inhibitors of collagen expression include, without limitation, Pirfenidone (InterMune), Halofuginone (Collgard) and F351 (Shanghai Genomics).

Exemplary low molecular weight heparin or heparin analogs include, without limitation, Sulodexide (Keryx).

Exemplary copper chelators include, without limitation, Trientine (Protemix), Coprexa (Pipex), and tetrathiomolybdate.

Exemplary TNF-α blocking agents include, without limitation, Etanercept (Enbrel™) and pentoxyfylline (Trental™).

Exemplary HMG-CoA reductase inhibitors include, without limitation, statins such atorvastatin (Lipitor), fluvastatin (Lescol), lovastatin (Mevacor, Altocor), pitavastatin (Livalo), pravastatin (Pravachol), rosuvastatin (Crestor), and simvastatin (Zocor).

Exemplary Thy-1 (CD90) inhibitors include monoclonal antibodies against Thy-1 (e.g., clone 5E10, Gundlach et al., *Bioconjug. Chem.* 22(8):1706-14 (2011), which is hereby incorporated by reference in its entirety).

Other known anti-fibrotic agents include, without limitation, 5-flurouracil (5-FU; a pyrimidine analog), mitomycin C (MMC), colchicine (antibiotic), d-penicillamine, Pediapred oral liquid, Medrol, cyclosporine (an immunosuppressant), mycophenolate mofetil (MMF; Cellcept; an immunosuppressant); prednisolone; bovine collagen type I, ribavirin (a guanosine (ribonucleic) analog), spirichostatin A (a histone deacetylase inhibitor); TGF-2 specific inhibitors (transglutaminase-2), tacrolimus (FK5-6, a calcineurin inhibitor), relaxin, taurine, niacin, treprostinil (a prostacyclin analog), Tiplaxtinin (PAI-039, a plasminogen activator-1 inhibitor); Pentraxin-1 (e.g., serum amyloid P component (SAP), c-reactive protein (CRP), and PTX-3) and Pentraxin-2 (PTX-2 or PRM-151), imidazolium and imidazolinium salts (U.S. Publication Application No. 20116178040, which is hereby incorporated by reference in its entirety) and IL-17 antagonists (U.S. Publication Application No. 20110091378, which is hereby incorporated by reference in its entirety); relaxin (a hormone; U.S. Publication Application No. 20120101325, which is hereby incorporated by reference in its entirety), ultraviolet A (UVA), and cannabinoids and agents altering the MMP-TIMP balance.

Explicitly excluded from the scope of additional anti-fibrotic agents are those agents described as being possibly co-administered with the polyether antimicrobial alexidine, as described in U.S. Publ. No. 2009/0054381 to Letts et al., which is hereby incorporated by reference in its entirety; and those agents described as being possibly co-administered with the polyether antimicrobial amsacrine, as described in U.S. Publ. No. 2007/0202051 to Schuschnig, which is hereby incorporated by reference in its entirety.

These additional anti-fibrotic agents can be administered in any previously known dosage. Compositions including these agents preferably contain from about 0.01 to about 99 weight percent, more preferably from about 2 to about 60 weight percent, of therapeutic agent together with the adjuvants, carriers, and/or excipients. The amount of active compound in such therapeutically useful compositions is such that a suitable dosage unit will be obtained. The dosage of the one of these additional anti-fibrotic agents is preferably administered at a dose of between about 0.01 mg per kg of body weight per day (mg/kg/day) to about 100 mg/kg/day, preferably 0.01 mg per kg of body weight per day (mg/kg/day) to 10 mg/kg/day, and most preferably 0.1 to 5.0 mg/kg/day.

Administration of one or more of the additional anti-fibrotic agents (or compositions containing the same) can be carried out orally, parenterally, periadventitially, subcutaneously, intravenously, intramuscularly, intraperitoneally, by inhalation, by intranasal instillation, by implantation, by intracavitary or intravesical instillation, intraocularly, intraarterially, intralesionally, transdermally, intradermally or by application to mucous membranes. Other suitable modes of delivery can also be used.

The additional anti-fibrotic agents can be co-administered with the active agents described above in a single formulation or in separate formulations.

A further aspect of the invention relates to a recombinant cell line that includes a recombinant gene that expresses a detectable expression product in a dose-dependent response to TGFβ concentration. This recombinant cell line is useful for screening agents that can induce a change in TGFβ expression levels. The recombinant cell line can be any human or animal derived cell line that can be maintained in culture.

The recombinant gene can be prepared using recombinant techniques that are well known to those of skill in the art. In one embodiment, the expression product is luciferase, preferably one that comprises a half-life that is less than 2 hours (see LeClerc, *Biotechniques* 29(3):590-8 (2000), which is hereby incorporated by reference in its entirety), and the open reading frame is operably coupled to a promoter element that is responsive to TGFβ. Although any suitable promoter element can be used, one suitable promoter element is a thymidine kinase (TK) promoter. Response to TGFβ can be engineered by introducing into the upstream promoter region one or more binding elements responsive to TGFβ (e.g., two TGFβ response elements, three TGFβ response elements, four TGFβ response elements, and so on).

An exemplary TK promoter has the nucleotide sequence shown below:

(SEQ ID NO: 1)
CGGCCCCGCCCAGCGTCTTGTCATTGGCGAATTCGAACACGCAGATGC

AGTCGGGGCGGCGCGGTCCGAGGTCCACTTCGCATATTAAGGTGACGC

GTGTGGCCTCGAACACCGAGCGACCCTGCAGCGACCCGCTTAACAGCG

TCAACAGCGTGCCGCAGATCTCGAGA.

An exemplary TGFβ response element has the nucleotide sequence shown below:

(SEQ ID NO: 2)
TACTAAGTCTAGACGGCAGTCTAGACGTACTAAGTCTAGACGGCAGTC

TAGACGTAGAGCTCGGCCCCGCCCAGCGTCTTGTC.

An exemplary luciferase open reading frame has the nucleotide sequence shown below:

(SEQ ID NO: 3)
ATGGAAGATGCCAAAAACATTAAGAAGGGCCCAGCGCCATTCTACCCA

CTCGAAGACGGGACCGCCGGCGAGCAGCTGCACAAAGCCATGAAGCGC

TACGCCCTGGTGCCCGGCACCATCGCCTTTACCGACGCACATATCGAG

GTGGACATTACCTACGCCGAGTACTTCGAGATGAGCGTTCGGCTGGCA

GAAGCTATGAAGCGCTATGGGCTGAATACAAACCATCGGATCGTGGTG

TGCAGCGAGAATAGCTTGCAGTTCTTCATGCCCGTGTTGGGTGCCCTG

TTCATCGGTGTGGCTGTGGCCCCAGCTAACGACATCTACAACGAGCGC

GAGCTGCTGAACAGCATGGGCATCAGCCAGCCCACCGTCGTATTCGTG

AGCAAGAAAGGGCTGCAAAAGATCCTCAACGTGCAAAAGAAGCTACCG

ATCATACAAAAGATCATCATCATGGATAGCAAGACCGACTACCAGGGC

TTCCAAAGCATGTACACCTTCGTGACTTCCCATTTGCCACCCGGCTTC

AACGAGTACGACTTCGTGCCCGAGAGCTTCGACCGGGACAAAACCATC

GCCCTGATCATGAACAGTAGTGGCAGTACCGGATTGCCCAAGGGCGTA

GCCCTACCGCACCGCACCGCTTGTGTCCGATTCAGTCATGCCCGCGAC

CCCATCTTCGGCAACCAGATCATCCCCGACACCGCTATCCTCAGCGTG

GTGCCATTTCACCACGGCTTCGGCATGTTCACCACGCTGGGCTACTTG

ATCTGCGGCTTTCGGGTCGTGCTCATGTACCGCTTCGAGGAGGAGCTA

TTCTTGCGCAGCTTGCAAGACTATAAGATTCAATCTGCCCTGCTGGTG

CCCACACTATTTAGCTTCTTCGCTAAGAGCACTCTCATCGACAAGTAC

GACCTAAGCAACTTGCACGAGATCGCCAGCGGCGGGGCGCCGCTCAGC

AAGGAGGTAGGTGAGGCCGTGGCCAAACGCTTCCACCTACCAGGCATC

CGCCAGGGCTACGGCCTGACAGAAACAACCAGCGCCATTCTGATCACC

CCCGAAGGGGACGACAAGCCTGGCGCAGTAGGCAAGGTGGTGCCCTTC

TTCGAGGCTAAGGTGGTGGACTTGGACACCGGTAAGACACTGGGTGTG

AACCAGCGCGGCGAGCTGTGCGTCCGTGGCCCCATGATCATGAGCGGC

TACGTTAACAACCCCGAGGCTACAAACGCTCTCATCGACAAGGACGGC

TGGCTGCACAGCGGCGACATCGCCTACTGGGACGAGGACGAGCACTTC

TTCATCGTGGACCGGCTGAAGAGCCTGATCAAATACAAGGGCTACCAG

GTAGCCCCAGCCGAACTGGAGAGCATCCTGCTGCAACACCCCAACATC

TTCGACGCCGGGGTCGCCGGCCTGCCCGACGACGATGCCGGCGAGCTG

CCCGCCGCAGTCGTCGTGCTGGAACACGGTAAAACCATGACCGAGAAG

-continued

```
GAGATCGTGGACTATGTGGCCAGCCAGGTTACAACCGCCAAGAAGCTG

CGCGGTGGTGTTGTGTTCGTGGACGAGGTGCCTAAAGGACTGACCGGC

AAGTTGGACGCCCGCAAGATCCGCGAGATTCTCATTAAGGCCAAGAAG

GGCGGCAAGATCGCCGTGAATTCTCACGGCTTCCCTCCCGAGGTGGAG

GAGCAGGCCGCCGGCACCCTGCCCATGAGCTGCGCCCAG.
```

In certain embodiments, the recombinant cell line is used in a method of identifying a compound that inhibits TGFβ-mediated cellular activity. This method includes growing a recombinant cell line in the presence of TGFβ and a compound of interest, and measuring the amount of the detectable expression product and comparing the measured amount to a control lacking the compound of interest and/or a control lacking TGFβ, wherein a significant difference in the measured amount of the detectable expression product, relative to the control, indicates that the compound of interest inhibits TGFβ-mediated cellular activity.

When luciferase or another fluorescent protein is used as the detectable expression product, measuring can be carried out using an optical detection system.

In this embodiment, the step of growing the recombinant cell line in the presence of TGFβ and the compound of interest is carried out for a period of time sufficient to allow for an assessment of whether the compound of interest inhibits TGFβ-mediated expression of the detectable expression product. In certain embodiments, this growing step is carried out for at least about 12 hours before said measuring, and in certain other embodiments this growing step is carried out for at least about 24 hours before said measuring.

EXAMPLES

The following examples are provided to illustrate embodiments of the present technology but are by no means intended to limit its scope.

Materials and Methods for Examples

Cell Culture:

Primary human fibroblasts were acquired and cultured as previously described (Lehmann et al., "Novel anti-adipogenic activity produced by human fibroblasts," *Am. J. Physiol. Cell Physiol.* 229(3):C672-C681 (2010), which is hereby incorporated by reference in its entirety). HEK293FT cells were obtained from the American Type Culture Collection (Rockville, Md.) and cultured in DMEM supplemented with 10% fetal calf serum (Hyclone) and antibiotics. DMEM, MEM and hygromycin were purchased from Gibco (Carlsbad, Calif.). Fibroblast growth medium was purchased from Promocell. Other compounds were obtained as follows: salinomycin (Cayman), narasin, monensin and clioquinol (all three from Sigma). Recombinant human TGFβ was obtained from R&D systems and was used at final concentrations of either 1, 5 or 10 ng/ml.

Development of TGFβ Responsive Cell Line:

The minimal thymidine kinase promoter was amplified by PCR with the following forward and reverse primers, of which the forward primer contained four tandem Smad binding elements (SBE):

```
Fwd (SEQ ID NO: 4, 5'→3'):
AGGTACCTACTAAGTCTAGACGGCAGTCTAGACGTACTAAGTCTAGAC

GGCAGTCTAGACGTAGAGCTCGGCCCCGCCCAGCGTCTTGTC

Rev (SEQ ID NO: 5, 5'→3'):
TAAAGCTTCTCGAGATCTGCGGCACGCT
```

Restriction sites in the primers are underlined. The resultant PCR product was TOPO cloned (Invitrogen) and the correct insert was verified by DNA sequencing. The construct was digested with SacI-HindIII and the SBEx4-TK insert was purified and ligated with the pGL4.15 vector (Promega). Clones were verified by restriction digest and then tested for TGFβ responsiveness in transient transfections of 293FT cells. Once the pSBEx4-TK-luc construct was demonstrated to be TGFβ responsive, the construct was introduced into 293FT cells for stable cell line production. Clones were selected by treatment with 200 μg/ml hygromycin. 20 clones were selected and screened for TGFβ-induced luciferase activity. One clone that was robustly responsive was subsequently used in the small molecule screen.

Plasmid DNA Transfection:

Plasmid DNA was introduced into human fibroblasts by electroporation. Plasmids were electroporated with an Amaxa nucleofector (program U-025) into $1 \times 10^6$ cells. The pcDNA3-flag MKK6(glu) plasmid was obtained from Addgene (plasmid 13518, from Roger Davis' lab). After transfection cells were cultured for 12-24 hours and culture medium was subsequently changed to treatment conditions.

Western Blotting:

Total protein was isolated from $0.5-2 \times 10^6$ cells and lysed in 60 mM Tris, pH 6.8, 2% SDS containing 1× protease inhibitor cocktail (Sigma, St. Louis, Mo.). The lysates were passed through a 26 gauge needle 5-6 times to shear genomic DNA. Protein concentrations were determined using the detergent compatible protein assay (BioRad). Total protein (1-10 ug per lane) was subjected to SDS-PAGE. Protein gels were transferred to PVDF membrane (Millipore) and probed with antibodies as specified. Western blot band intensities were quantified using ImageLab software (BioRad). Protein expression was normalized to β-tubulin levels.

Collagen Production Assay:

Cell culture supernatant was collected and transferred (5-20 ul) to PVDF membrane using a slot blot device. The membrane was blocked and probed with a goat anti-collagen antibody (1:5000), washed and incubated with a donkey anti-goat antibody conjugated to HRP. Band intensities were quantified using ImageLab software and values were normalized to vehicle treatments.

Alamar Blue Viability Assay: $5 \times 10^3$ cells were plated per well in a 96-well plate (Griener) with 200 ul of culture medium. Vehicle (DMSO), salinomycin and/or TGFβ (1 ng/ml) were added as indicated and then 20 ul of alamar blue reagent was added to all wells. Cells were incubated for 24 and 48 hours and then fluorescence of the oxidized alamar reagent was measured (ex 470 nM, em 480 nM). Background fluorescence was subtracted from all wells and the fluorescence was normalized to vehicle treated cells. The assay was performed in two different human fibroblast strains and treatments were performed in triplicate.

BrdU Incorporation Assay:

Human fibroblasts were seeded on a 96-well plate at a density of $1 \times 10^5$ cells/well. Cells were treated in triplicate. Cell proliferation was determined using the bromodeoxyuridine (BrdU) assay following manufacturer's instructions. Briefly, cells were treated with a BrdU label at a 1:2000 dilution for 24 h after the initial 72 h treatment with TGFβ+/−drugs. BrdU incorporation was measured using the BrdU Cell Proliferation Assay kit (Calbiochem, San Diego, Calif.) at 450-540 nm using a Varioskan microplate reader.

Immunocytochemistry:

Human orbital fibroblasts were seeded in a multiwell dish and grown to 85-90% confluence. Cells were then treated with TGFβ+/−salinomycin or narasin for 72 h. Following treatment cells were fixed with 4% paraformaldehyde. Cells were then permeabilized and non-specific binding sites were blocked using 10% serum in PBS for thirty minutes at room temperature. Cells were incubated overnight at 4° with a monoclonal αSMA antibody which detects αSMA in differentiated fibroblasts. Cells were washed with PBS then incubated at room temperature with a Texas Red-conjugated secondary antibody at a concentration of 1:200. DAPI, a fluorescent counterstain, was used to visualize nuclear DNA.

Statistical Analysis:

Student's T test and One-way analysis of variance (ANOVA) were used for statistical analysis and p values of $p<0.05$; $p<0.01$; $p<0.001$; were considered significant.

Example 1—Design of TGFβ-Inducible Luciferase Construct and Use Thereof

Figure 1B:
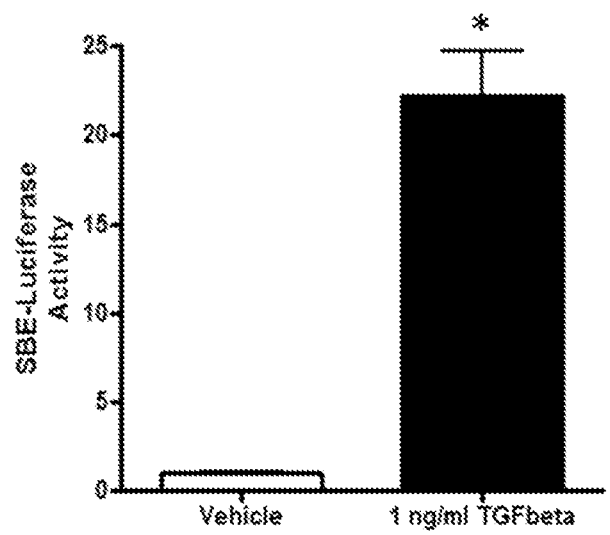

Excessive scarring results from the formation of too many myofibroblasts and the production of too much extracellular matrix material such as collagen. Since TGFβ drives the formation of myofibroblasts in part through activating the Smad pathway, a reporter construct was designed to serve as a measure of TGFβ-induced Smad activity (FIG. 1A). Four tandem Smad binding elements (SBE) were inserted upstream of the minimal thymidine kinase promoter. The SBEx4-TK promoter was inserted into the pGL4.15 vector which contains a destabilized firefly luciferase gene and the hygromycin resistance gene. The pSBEx4-TK-luc-Hygro plasmid was then introduced into HEK293FT cells by lipofection. Stable clones were generated and screened for TGFβ induced luciferase activity. One clone was selected that consistently gave a 15 to 20-fold induction of luciferase activity when cells were treated with TGFβ for 24 hours (FIG. 1B).

Figure 1C:
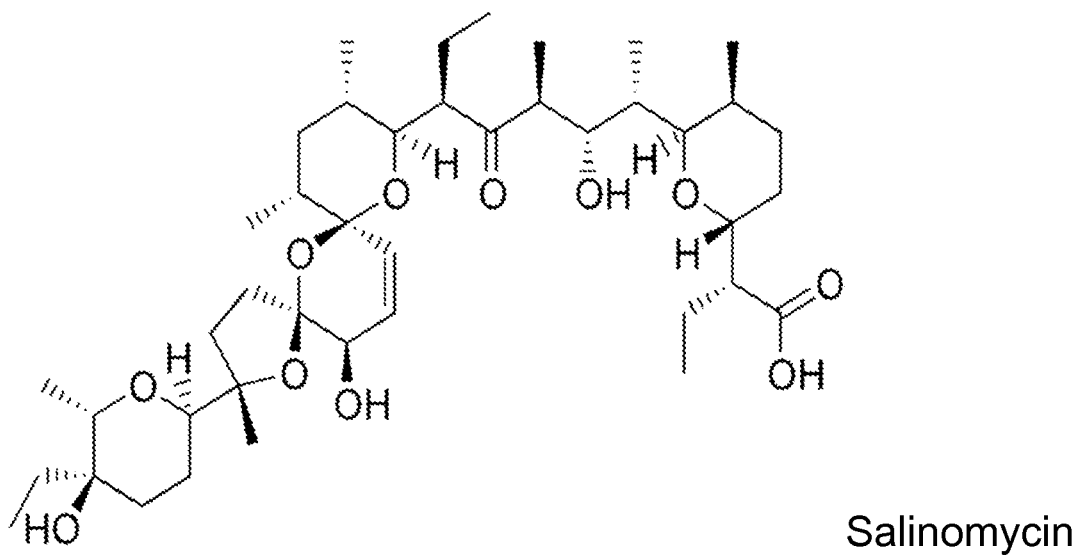
Figure 1D:
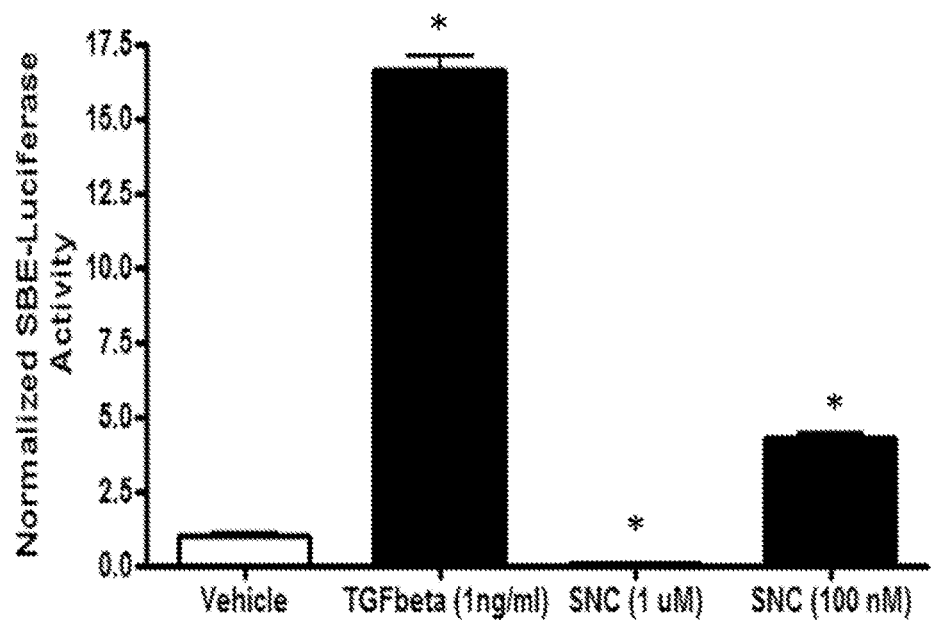

To find compounds that inhibit TGFβ activity and thus may be novel anti-scarring compounds, the Spectrum collection of 2,300 small molecules was screened with the cell line. One small molecule that was particularly potent at inhibiting luciferase activity was the polyether antibiotic agent, salinomycin (FIG. 1C). Further testing of salinomycin showed a dose responsive decrease in TGFβ-induced luciferase, where 100 nM salinomycin reduced luciferase activity by approximately 4-fold and 1 uM salinomycin reduced luciferase activity levels to below baseline levels (FIG. 1D). Salinomycin, an antibiotic produced from *Streptomyces albus* is used as coccidiostat agent in animal feed (Knirschova et al., "Multiple regulatory genes in the salinomycin biosynthetic gene cluster of *Streptomyces albus* CCM 4719," *Folia Microbiologica* 52:359-365 (2007), which is hereby incorporated by reference in its entirety). Furthermore, salinomycin has recently been shown to have activity against cancer stem cells (Naujokat et al., "Salinomycin as a drug for targeting human cancer stem cells," *J. Biomed. Biotechnol.* 2012:950658 (2012), which is hereby incorporated by reference in its entirety). Thus, further investigation was made to assess the use of salinomycin as an anti-scarring agent.

Fibroblasts are sentinel cells that respond to numerous stimuli and serve as key effector cells in many biological processes (Baglole et al., "More than structural cells, fibroblasts create and orchestrate the tumor microenvironment," *Immunol. Invest.* 35:297-325 (2006), which is hereby incorporated by reference in its entirety). One key function of fibroblasts is their differentiation into scar-forming myofibroblasts. Thyroid eye disease is a disorder in which myofibroblasts and scar tissue accumulate in the ocular orbit causing pain, proptosis and in severe cases, blindness (Lehmann et al., "Immune mechanisms in thyroid eye disease," *Thyroid: Official Journal of the American Thyroid Association* 18:959-965 (2008), which is hereby incorporated by reference in its entirety). Human orbital fibroblasts have been shown to respond dramatically to TGFβ by forming myofibroblasts that express uSMA, calponin and produce high levels of collagen (Kuriyan et al., "Orbital fibroblasts from thyroid eye disease patients differ in proliferative and adipogenic responses depending on disease subtype," *Invest. Ophthalmol. Vis. Sci.* 54:7370-7377 (2013), which is hereby incorporated by reference in its entirety). Thus, TED fibroblasts were an ideal model to test the ability of salinomycin to block TGFβ function.

Figure 2A:
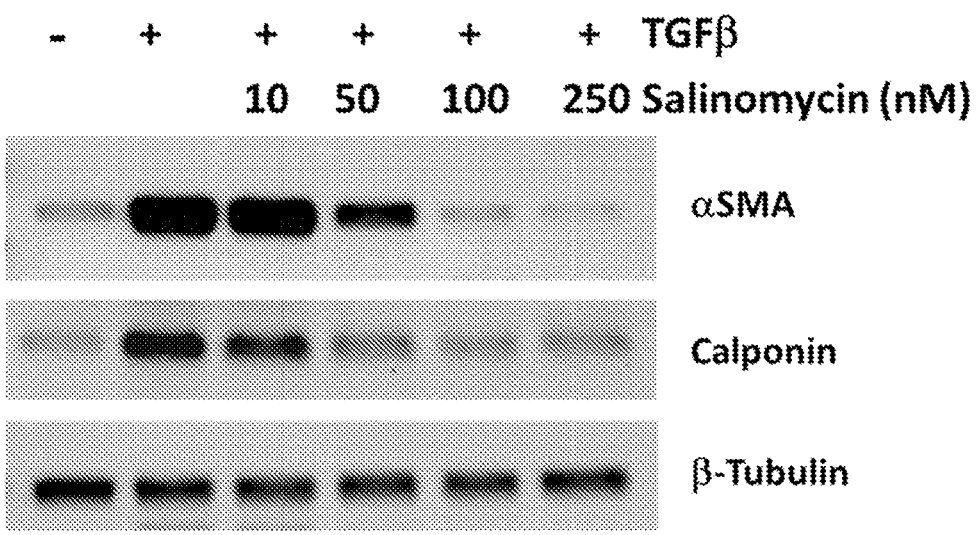
FIGS. 2A-C show that salinomycin inhibits TGFβ-induced expression of myofibroblast markers in human fibroblasts.
Figure 2B:
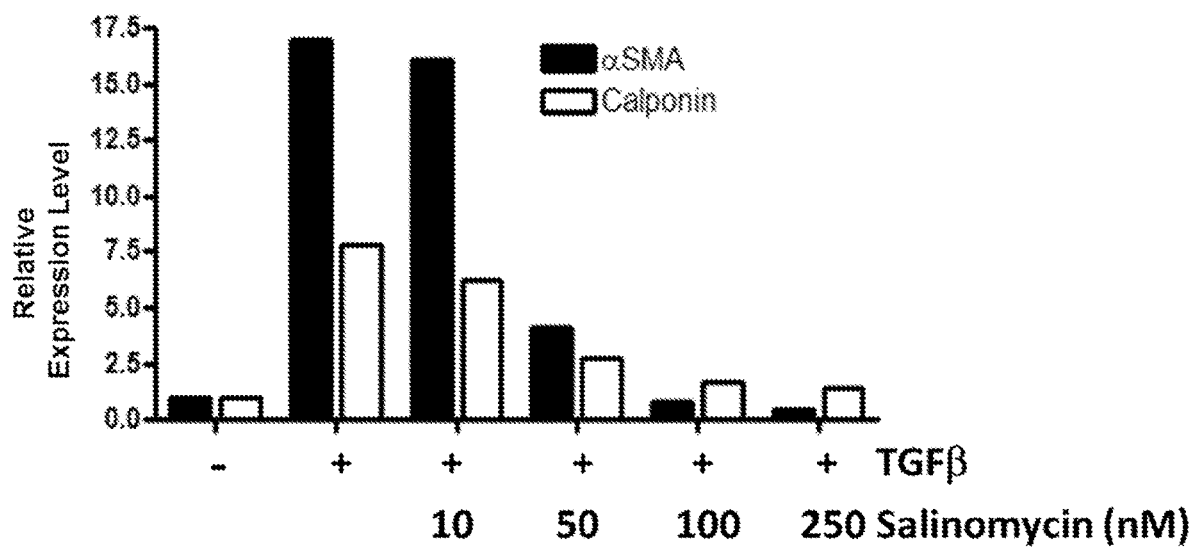
Figure 2C:
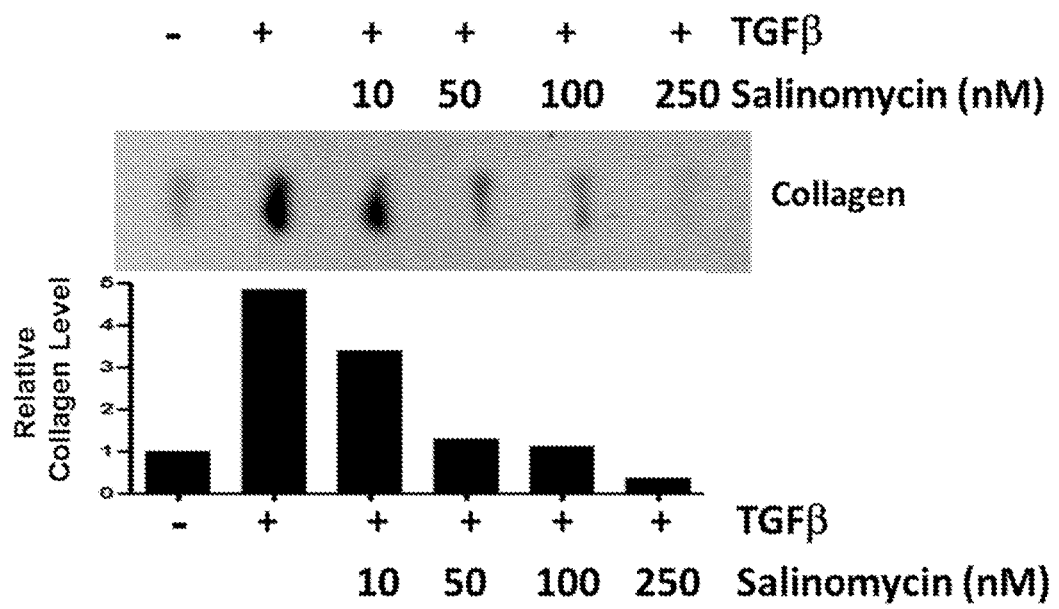

TED fibroblasts were treated with TGFβ (1 ng/ml) in the presence or absence of 10-250 nM salinomycin for 72 hours to allow formation of myofibroblasts. After 72 hours, cells were harvested and analyzed by Western blot. As expected, the fibroblasts robustly responded to TGFβ, expressing high levels of αSMA and calponin (FIG. 2A). Interestingly, salinomycin blocked the expression of αSMA and calponin in a dose dependent manner (FIGS. 2A and 2B). At 50 nM salinomycin, expression of αSMA was reduced by 4-fold over TGFβ treatment alone. Furthermore, at 250 nM salinomycin, αSMA expression was reduced by approximately 16-fold, to levels at or below untreated fibroblasts. Similar results were observed with calponin expression (FIGS. 2A and 2B). Another key role of myofibroblasts in scar formation is the production of collagen. Whether salinomycin could block myofibroblast collagen production was assessed. Cells were treated with TGFβ and salinomycin as above and after 72 hours, culture medium was collected and analyzed for collagen levels using a specific collagen I antibody and slot blot analysis. As FIG. 2C shows, TGFβ induced myofibroblasts produce high levels of collagen. However, salinomycin blocked production of collagen in a dose-dependent manner. Starting at 10 nM salinomycin, collagen production decreases and at 100 nM salinomycin, collagen production is at baseline levels. Finally, at 250 nM salinomycin, collagen production is below baseline levels of untreated fibroblasts (FIG. 2C).

Figure 3A:
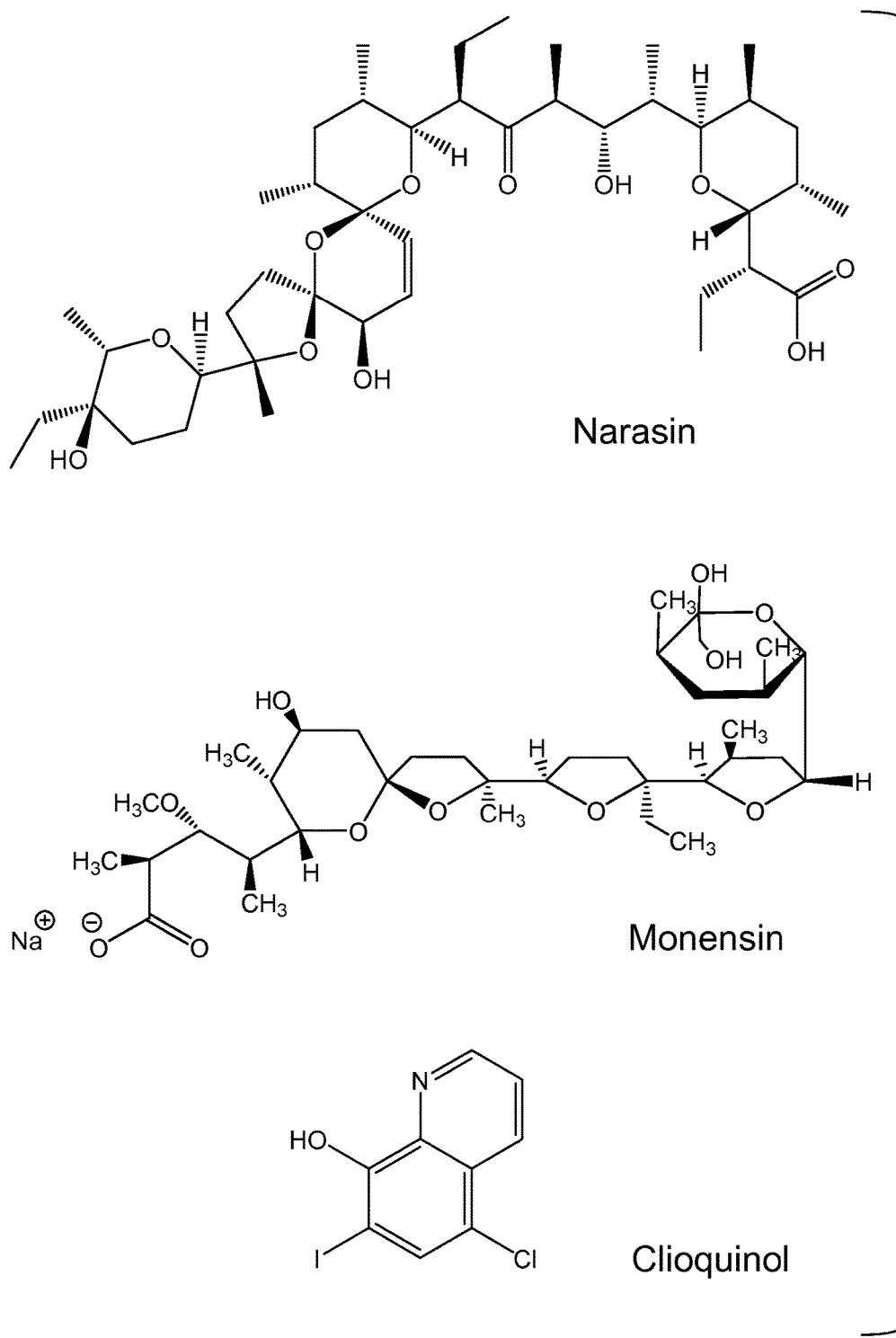
FIGS. 3A-C show that the three polyether ionophores salinomycin, narasin and monensin inhibit myofibroblast formation, but not the structurally unrelated ionophore clioquinol.

Example 2—Identification of Other Polyether Antibiotics that Block TGFβ-Induced Myofibroblast Formation Since salinomycin, a polyether antibiotic agent, could block formation of myofibroblasts, two other polyether antibiotic agents and a non-polyether ionophore, clioquinol, were tested for anti-myofibroblast activities (FIG. 3A). Narasin is a methylated derivative of salinomycin and is also a coccidiostat used in animal feed (Mortier et al., "Determination of the ionophoric coccidiostats narasin, monensin, lasalocid and salinomycin in eggs by liquid chromatography/tandem mass spectrometry," *Rapid Commun. Mass Spectrom.* 19:533-539 (2005), which is hereby incorporated by reference in its entirety). Monensin is another polyether ionophore that is used extensively in animal feed to prevent coccidiosis (Mortier et al., "Determination of the ionophoric coccidiostats narasin, monensin, lasalocid and salinomycin in eggs by liquid chromatography/tandem mass spectrometry," *Rapid Commun. Mass Spectrom.* 19:533-539 (2005), which is hereby incorporated by reference in its entirety). Finally, a fourth compound, clioquinol, was selected for analysis. Clioquinol is an anti-protozoal drug and ionophore, but it is structurally unrelated to salinomycin (Schimmer et al., "A phase I study of the metal ionophore clioquinol in patients with advanced hematologic malignancies," *Clin. Lymphoma, Myeloma Leuk.* 12:330-336 (2012), which is hereby incorporated by reference in its entirety).

Figure 3B:
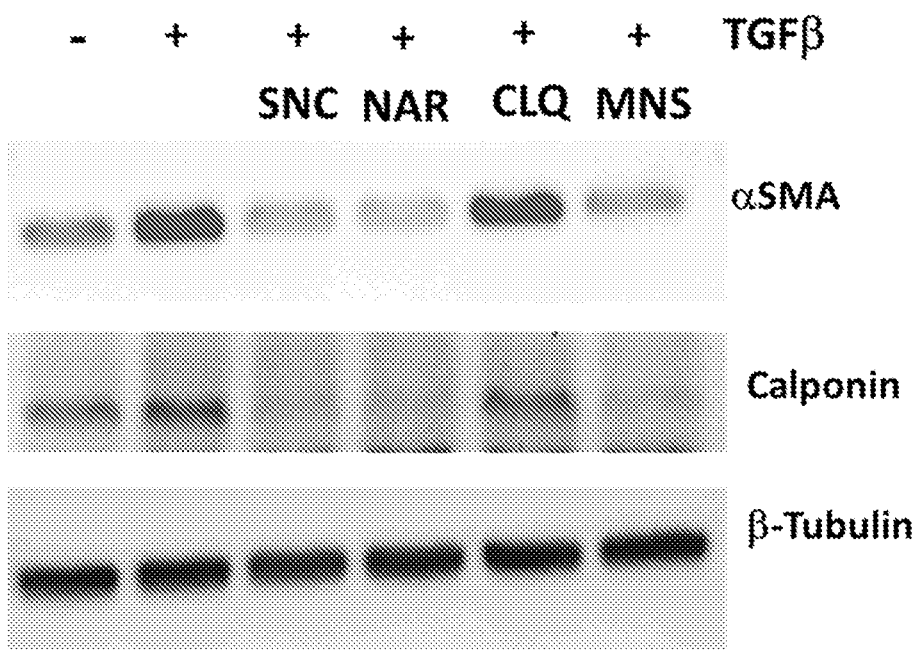
Figure 3C:
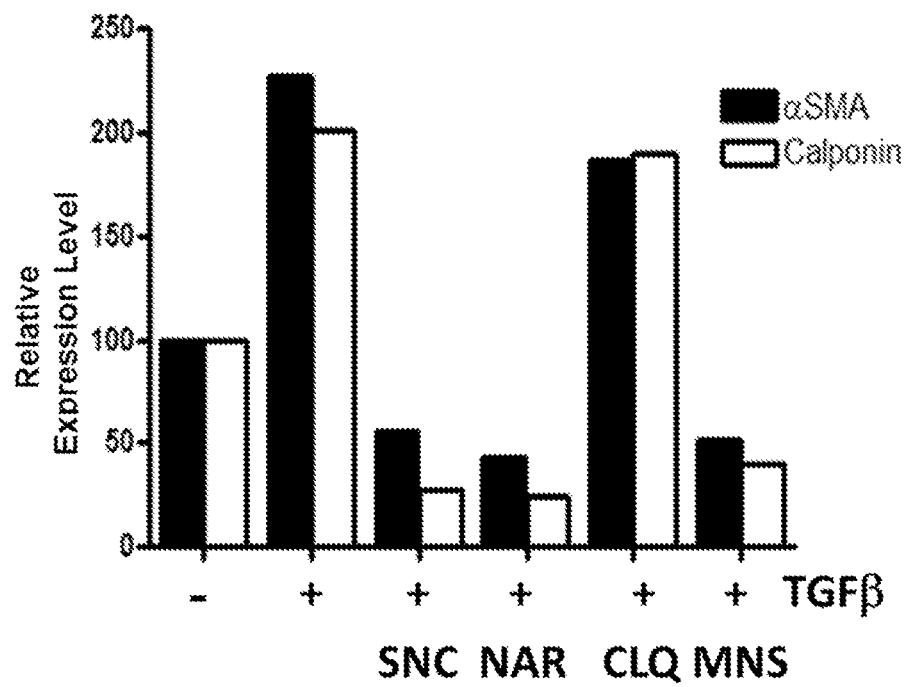

To test these four compounds, human fibroblasts were treated with TGFβ in the absence or presence of 250 nM of either salinomycin, narasin, clioquinol or monensin for 72 hours. After treatment, cell lysates were harvested and analyzed for the presence of the myofibroblast markers, αSMA and calponin (FIG. 3B). As expected, salinomycin reduced the expression of αSMA and calponin to lower than vehicle levels. Interestingly, both narasin and monensin had similar activities to salinomycin. However, the structurally unrelated compound clioquinol, did not inhibit expression of αSMA or calponin (FIGS. 3B and 3C). Thus, these data demonstrate that salinomycin and other polyether ionophores may specifically block TGFβ induced myofibroblast formation.

Figure 4A:
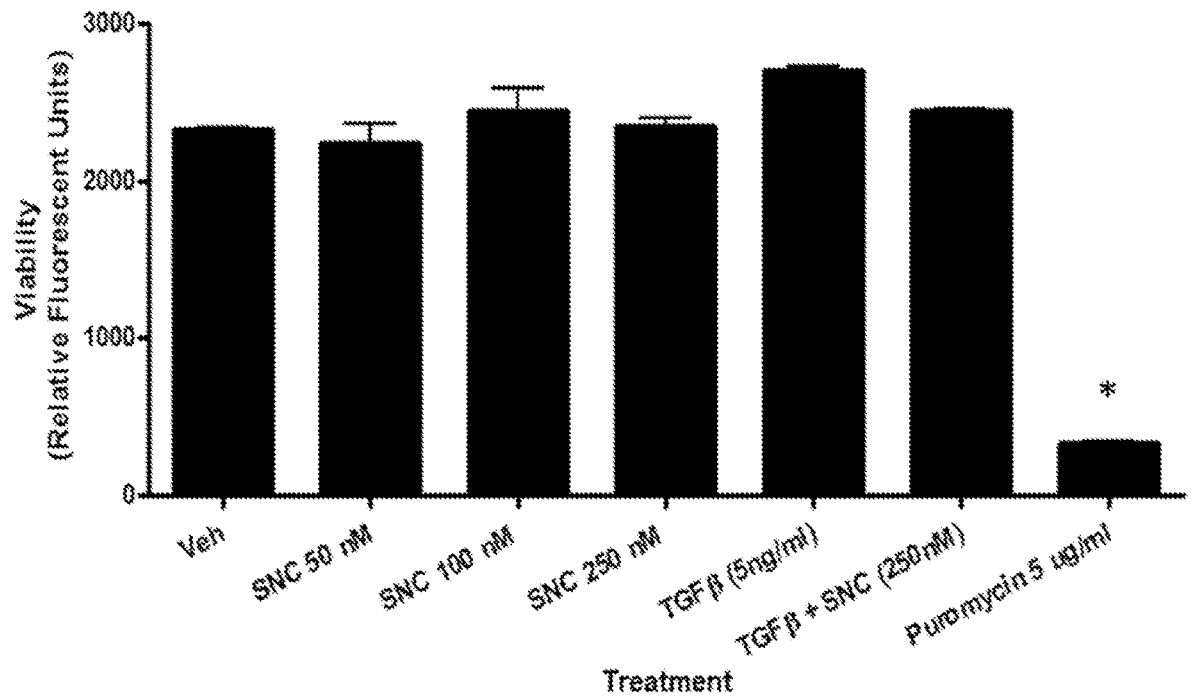
FIGS. 4A-B show that salinomycin does not affect viability or basal proliferation of human fibroblasts, however, it does block TGFβ induced proliferation.
Figure 4B:
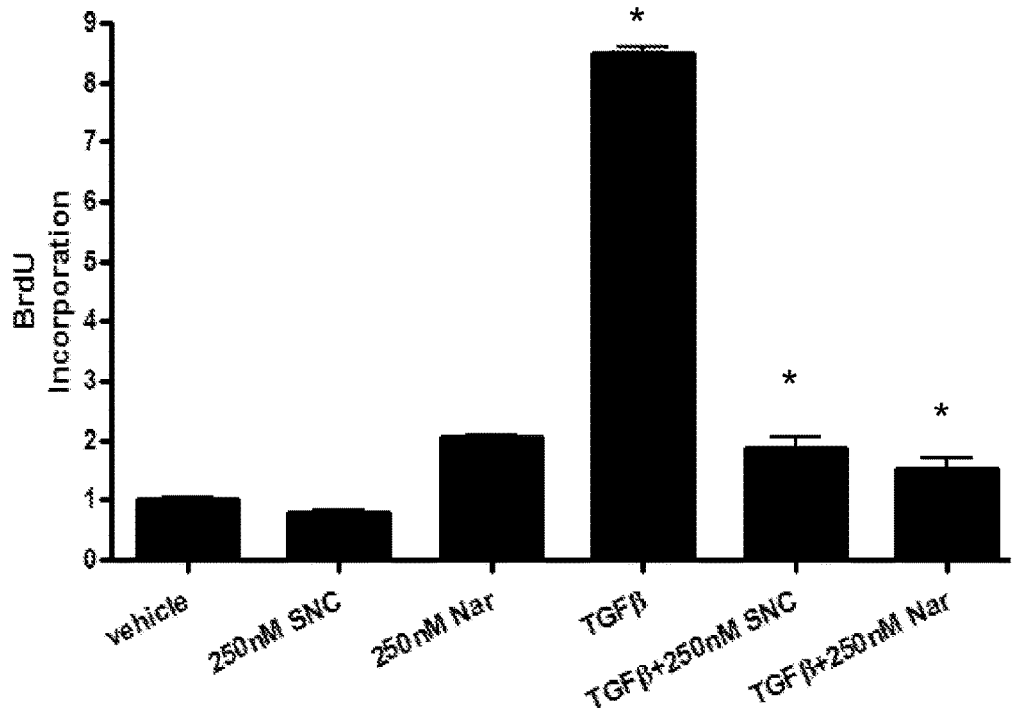

While salinomycin and other polyether ionophores blocked myofibroblast formation, it was next assessed whether these effects were a result of toxicity and/or due to a block of cell proliferation. Though the treatment doses are relatively low (efficacy in 100-250 nM range), a loss of cell viability could still be a possibility. To test this, human fibroblasts were treated with vehicle (DMSO), 50-250 nM salinomycin alone, TGFβ or TGFβ plus 250 nM salinomycin. As a positive control, fibroblasts were treated with the cytotoxic drug, puromycin. Treated cells were cultured in the presence of alamar blue reagent, which measures mitochondrial oxidation-reduction (REDOX) potential and serves as a quantitative viability sensor. After 72 hours of culture, alamar blue fluorescence was measured to assay cell viability (FIG. 4A). As expected, puromycin treatment resulted in a total loss of cell viability. However, treatment of salinomycin alone or salinomycin plus TGFβ did not result in a loss of viability. These results demonstrate that salinomycin is not affecting human fibroblast viability. It was also tested whether salinomycin affects basal fibroblast proliferation. To address this, cells were treated with vehicle or 250 nm of either salinomycin or narasin for 24 hours in the presence of bromodeoxyuridine (BrdU) to measure cell proliferation (FIG. 4A, first three bars). Neither salinomycin nor narasin blocked basal fibroblast proliferation. BrdU was also added to cells treated with TGFβ in the presence or absence of 250 nM salinomycin or narasin (FIG. 4B, last three bars). As expected, TGFβ induced human fibroblast proliferation. Remarkably, both salinomycin and narasin were able to beneficially block TGFβ induced proliferation by 4 to 5 fold, without affecting basal proliferation levels.

Figure 5A:
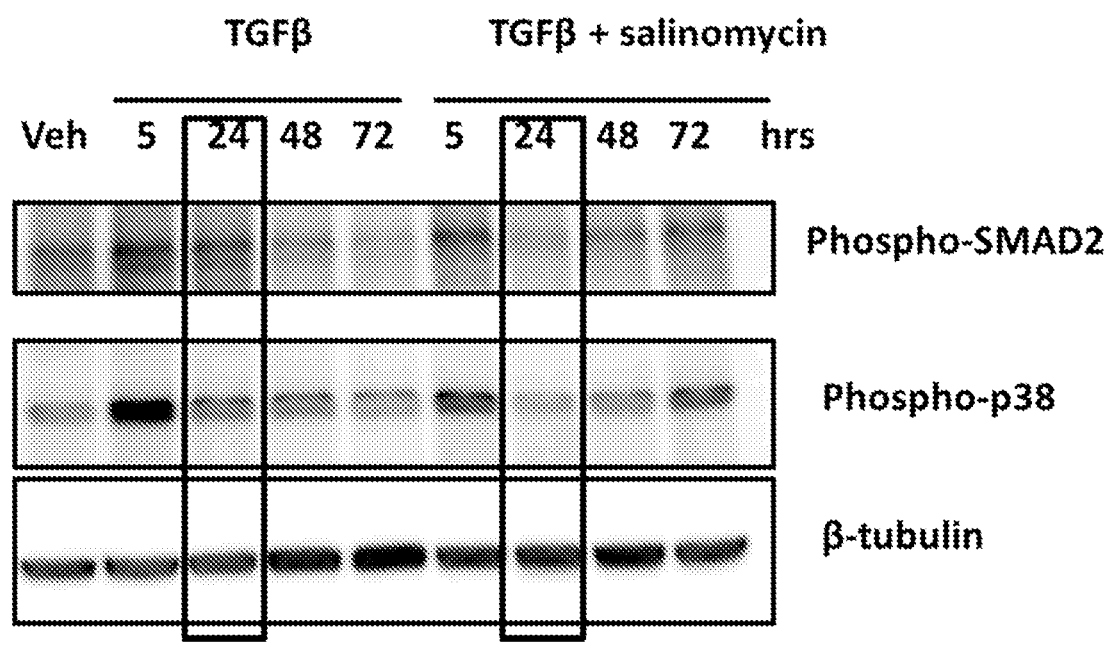
FIGS. 5A and 5B show that salinomycin inhibits TGFβ-induced p38 phosphorylation.
Figure 5B:
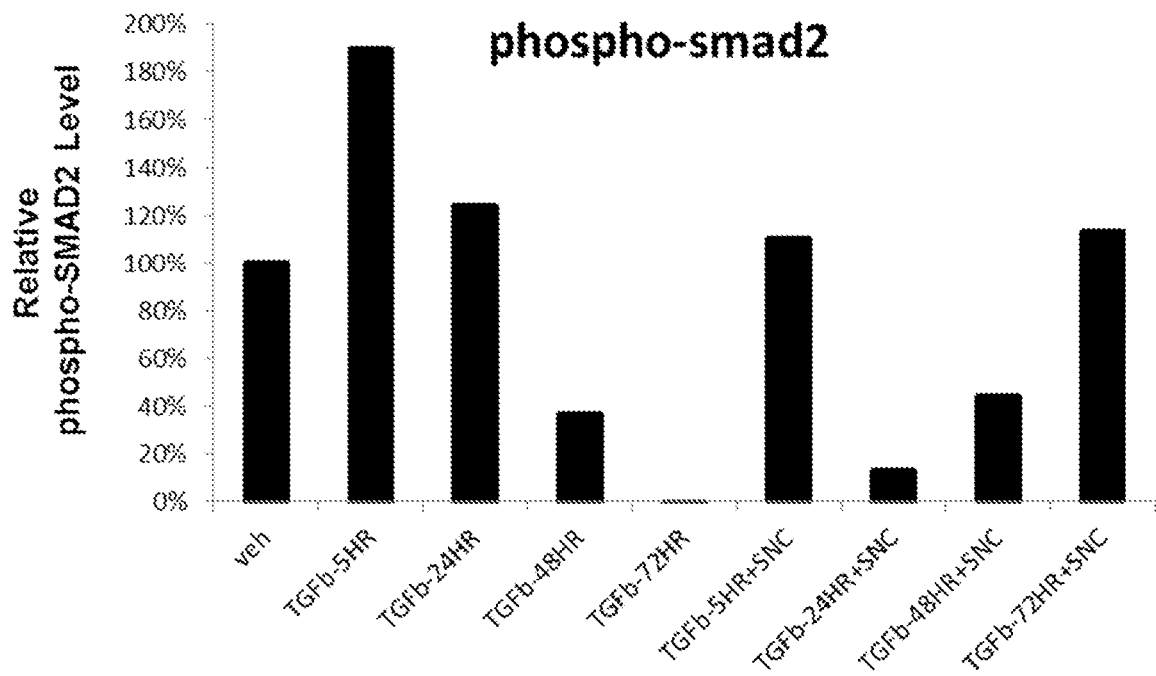

Example 3—Characterization of Mode of Action for Salinomycin Blockade of TGFβ-Induced Myofibroblast Formation To further characterize the molecular mechanisms whereby salinomycin (and other polyether antibiotics) blocks TGFβ induced myofibroblast formation, activation kinetics were analyzed for some of the key mediators of TGFβ signaling (Weiss et al., "The TGFbeta superfamily signaling pathway," *Wiley Interdiscip. Rev. Dev. Biol.* 2:47-63 (2013), which is hereby incorporated by reference in its entirety). Since salinomycin was first identified as a putative anti-scarring molecule by its ability to block TGFβ-induced Smad activity, the levels of phospho-Smad2 were analyzed by Western blot in cells treated with TGFβ or TGFβ plus salinomycin. TGFβ treatment induces phosphorylation of Smad2 in minutes in human fibroblasts, however, at early time points (30 sec-1 hour), salinomycin treatment did not affect phospho-Smad2 levels. The experiment was repeated, with samples being incubated for extended periods of time including 5, 24, 48 and 72 h hours (FIG. 5A, top panel). TGFβ treatment induced phospho-Smad2 by 200% at 5 hours and then phospho-Smad2 levels decreased at 24 (140%), 48 (40%), and 72 hours (~5% of vehicle levels) (FIG. 5B, top panel). Salinomycin treatment resulted in an 80% reduction of phospho-Smad2 levels, compared to TGFβ alone at 5 hours. Interestingly, salinomycin was most effective at blocking phospho-Smad2 levels at 24 hours, with approximately an 8-10 fold reduction compared to TGFβ treatment alone. This data indicated that salinomycin was not working directly on Smad2, but rather at another signaling step.

Therefore, activity of another signaling molecule that is involved in myofibroblast formation, namely the mitogen-activated protein kinase (MAPK), p38, was measured to assess its potential role in the observed results. P38 MAPKs are a class of protein kinases that respond to TGFβ, ultraviolet radiation and other stimuli. Phosphorylation and activation of p38 can lead to numerous downstream signaling pathways, including phosphorylation of Smad proteins. TGFβ treatment of human fibroblasts was observed to result in a dramatic induction of phospho-p38 at 5 hours (7 fold) and 24 hours (2-3 fold). Remarkably, salinomycin treatment completely blocked phospho-p38 levels at 5 hours TGFβ treatment (FIGS. 5A and 5B, lower panels). Furthermore, salinomycin treatment inhibited phospho-p38 by 80% at 24 hours TGFβ treatment. These data support the belief that salinomycin targets (along with other polyether antibiotics) the p38 signaling pathway in response to TGFβ.

Figure 6A:
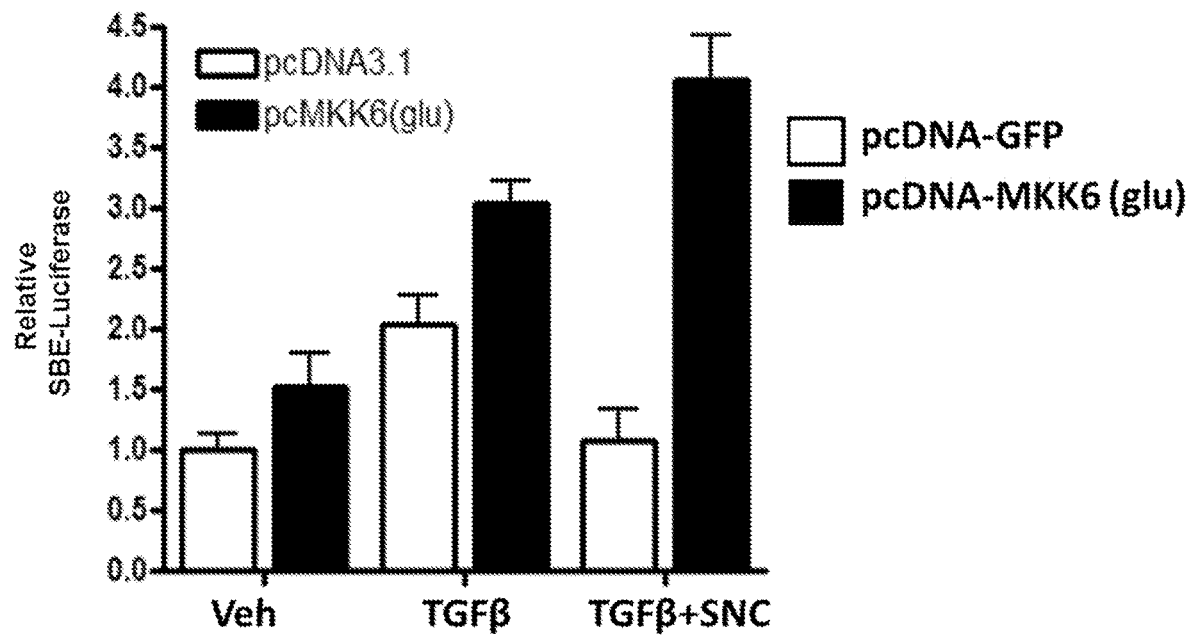
FIGS. 6A-C show that expression of constitutively active MKK6 attenuates the inhibitory effect of salinomycin on TGFβ.
Figure 6B:
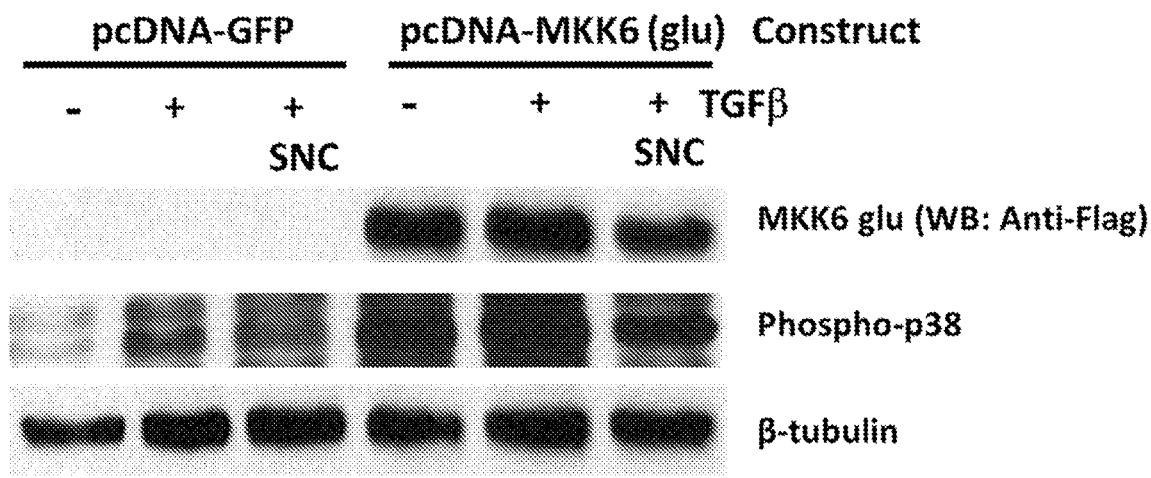
Figure 6C:
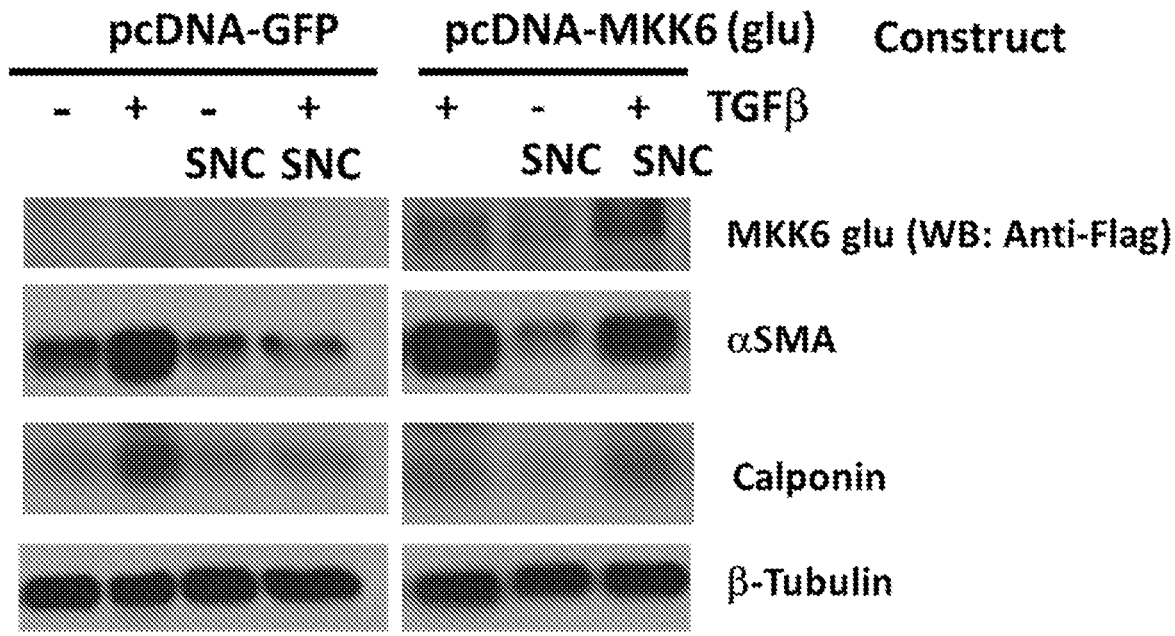
Figure 7:
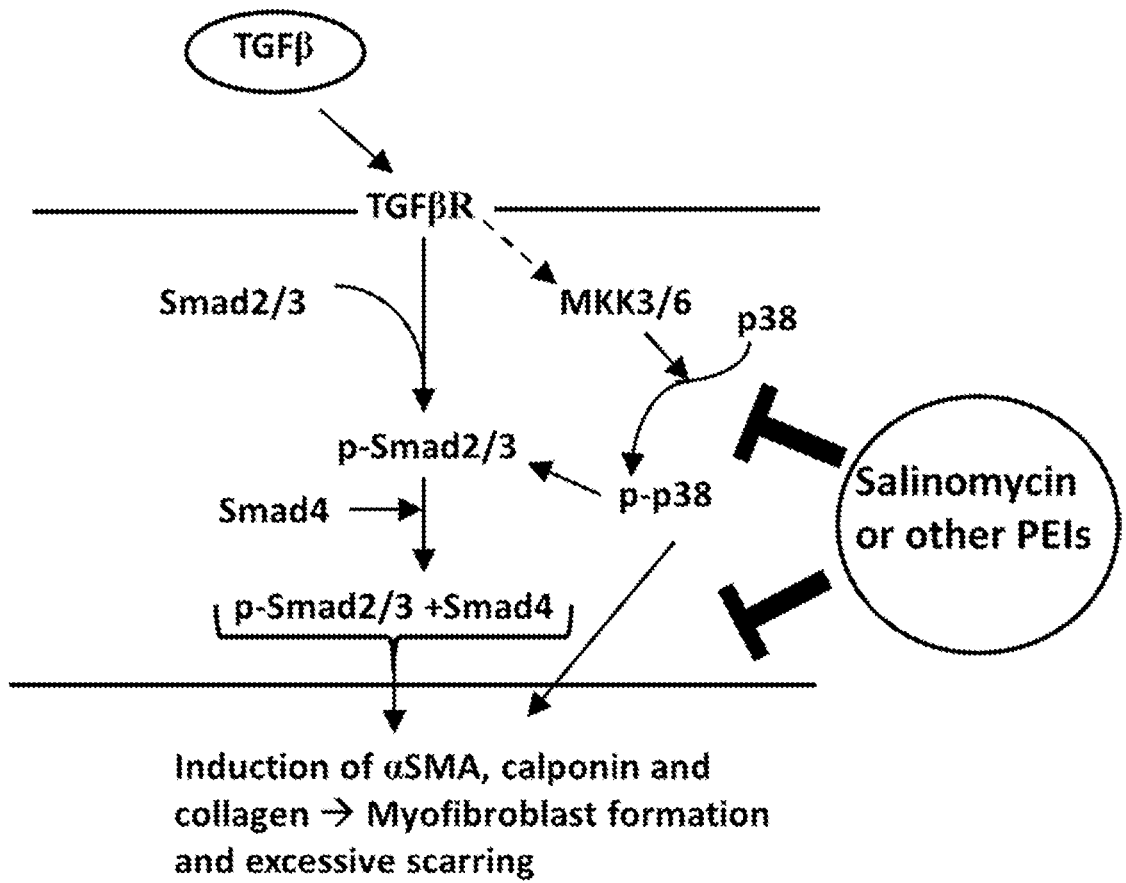
FIG. 7 is a schematic illustration showing a potential model for salinomycin (and other polyether ionophore) mode of action. Active TGFβ, present at high concentrations during wound healing, exuberant scarring or chronic inflammation, binds to the TGFβ receptor (TGFβR). Activation of the TGFβR triggers a range of cell signaling events including the phosphorylation and activation of Smad2/3 and p38MAPK (p38). Active p38 leads to a further increase of Smad2/3 activation. These signaling pathways converge to lead to transcription and expression of αSMA, calponin, collagen and other genes involved in myofibroblast formation and scarring. Salinomycin, or other polyether ionophores (PEI) can block the activation and phosphorylation of p38, thereby limiting activation of Smad2/3 and blocking myofibroblast formation.

To further test if salinomycin targets the p38 pathway to block myofibroblast formation, a plasmid encoding a mutant MKK6 (pcDNA3-flag MKK6(glu)) protein was used. MKK6 phosphorylates and thus activates p38 in response to extracellular signals such as TGFβ or other environmental stresses. The MKK6(glu) protein, which harbors glutamate mutations at amino acid residues serine 207 and threonine 211, is constitutively active and thus phosphorylates p38 irrespective of signal (Raingeaud et al., "MKK3- and MKK6-regulated gene expression is mediated by the p38 mitogen-activated protein kinase signal transduction pathway," *Mol. Cell. Biol.* 16:1247-1255 (1996), which is hereby incorporated by reference in its entirety). Thus, if salinomycin is blocking the p38 signaling pathway, MKK6(glu) should overcome the effect of salinomycin. MKK6(glu) was first tested using the SBE4-TK-luc reporter plasmid. The luciferase reporter plasmid was introduced into human fibroblasts along with the MKK6(glu) plasmid or a control plasmid (pcDNA3-GFP). Cells were then treated with vehicle, TGFβ or TGFβ plus 250 nM salinomycin. After 24 hours, luciferase activity was measured (FIG. 6A). As expected, in human fibroblasts expressing the GFP plasmid, TGFβ induced luciferase activity by 2-fold and salinomycin completely blocked TGFβ-induced luciferase activity. Interestingly, in cells expressing constitutively active MKK6(glu) plasmid, salinomycin was unable to block TGFβ-induced luciferase activity (FIG. 6A). MKK6(glu) was further tested to assess whether it could attenuate the ability of salinomycin to inhibit p38 phosphorylation. Control or MKK6(glu) plasmids were introduced into human fibroblasts by electroporation and then cells were treated with TGFβ for 24 hours. Following treatment, cells were analyzed for flag-MKK6(glu) expression and phospho-p38 by Western blot (FIG. 6B). As expected, salinomycin blocks phosphorylation of p38 at 24 hours. However, MKK6(glu) expression leads to a large induction of phospho-p38, regardless of salinomycin treatment. As a third test, control or MKK6(glu) plasmids were introduced into human fibroblasts by electroporation. After electroporation, cells were induced to form myofibroblasts by TGFβ treatment for 72 hours. Samples were analyzed for expression of flag-MKK6 (glu), αSMA, calponin and β-tubulin by Western blot (FIG. 6C). As expected TGFβ treatment induced expression of αSMA and calponin in control, GFP expressing cells and salinomycin blocked their induction (FIG. 6C, left hand panel). Interestingly, expression of MKK6(glu) attenuated the ability of salinomycin to block TGFβ induced αSMA and calponin (FIG. 6C, right hand panel). Taken together, these data provide strong evidence demonstrating that salinomycin blocks the p38 signaling pathway to prevent TGFβ induced Smad2/3-dependent signaling and formation of scar forming myofibroblasts (FIG. 7).

Discussion of Examples 1-3

Exuberant TGFβ signaling and excessive development of scar-forming myofibroblasts is at the root of disorders involving excessive scar formation. Unfortunately, therapeutic options to treat excessive scarring are limited and most are not proven to be effective (Klingberg et al., "The myofibroblast matrix: implications for tissue repair and fibrosis," *J. Pathol.* 229:298-309 (2013), which is hereby incorporated by reference in its entirety). The results presented in the preceding Examples identify salinomycin and other polyether ionophores as novel small molecules that block myofibroblast formation. Salinomycin potently blocked TGFβ induced expression of αSMA, calponin and collagen, all of which are hallmarks of myofibroblasts (FIG. 2). The ability of salinomycin to block expression of these myofibroblast markers has not been previously recognized. The knowledge gained from these studies highlights the potential of salinomycin and other polyether ionophores to serve as new anti-scarring drugs.

Figure 5B:
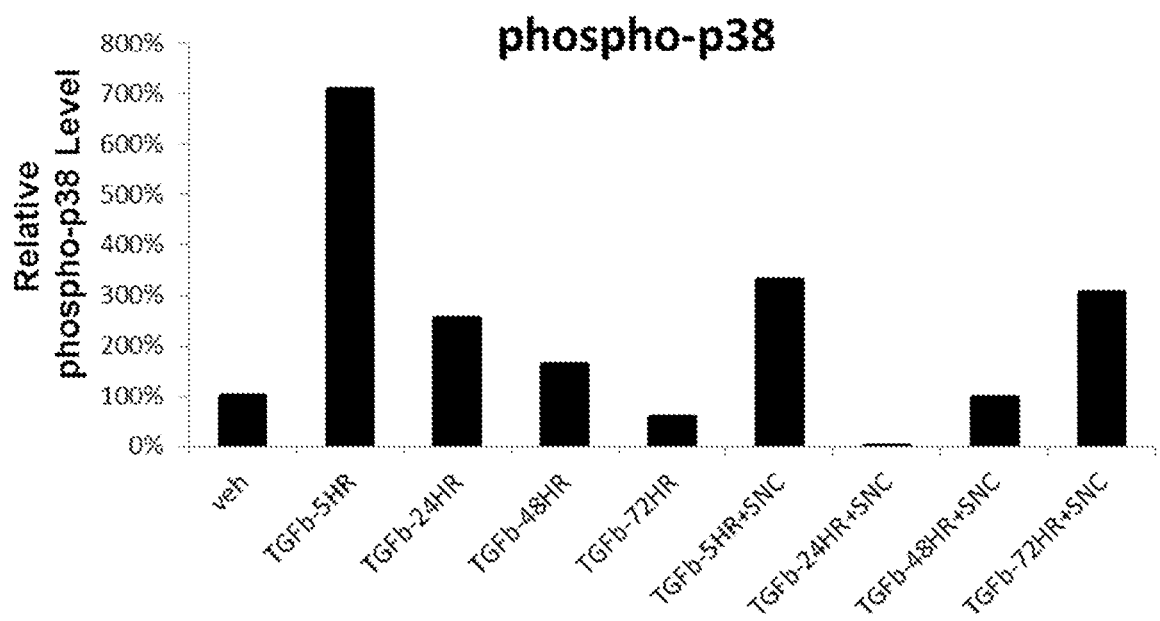

Heightened activity of TGFβ is observed in cancer, fibrosis and hypertrophic scarring and, thus, the pathway is under intense active research in order to develop new therapies (Akhurst et al., "Targeting the TGFbeta signalling pathway in disease," *Nat. Rev. Drug Discov.* 11:790-811 (2012), which is hereby incorporated by reference in its entirety). In the preceding Examples, a TGFβ-dependent, Smad reporter cell line was screened with a small molecule library consisting of bioactive drugs. Since Smad transcription factors are directly downstream of the TGFβ receptor, it was expected to identify small molecules that could act directly on the TGFβ receptor or Smad proteins, such as the small molecule inhibitor of the TGFβ receptor, SB-43152 (Laping et al., "Inhibition of transforming growth factor (TGF)-beta1-induced extracellular matrix with a novel inhibitor of the TGF-beta type I receptor kinase activity: SB-431542," *Mol. Pharmacol.* 62:58-64 (2002), which is hereby incorporated by reference in its entirety). These data support that salinomycin indirectly targets the Smad pathway by working through the p38 signaling pathway. The p38 pathway functions in myofibroblast formation in part by providing a feed forward loop to stimulate Smad2/3 phosphorylation and activation (FIG. 7) (Yang et al., "TRPV1 potentiates TGF-beta-induction of corneal myofibroblast development through an oxidative stress-mediated p38-SMAD2 signaling loop," *PloS one* 8:e77300 (2013), which is hereby incorporated by reference in its entirety). This is consistent with the data showing that salinomycin impairs phosphorylation of both p38 and Smad2 at later time points, whereas early time points were not affected (FIG. 5). The p38-MAPK pathway has been implicated in fibrosis of the kidney, lung and heart (Fan et al., "Decreased expression of p38 MAPK mediates protective effects of hydrogen sulfide on hepatic fibrosis," *Eur. Rev. Med. Pharmacol. Sci.* 17:644-652 (2013); Li et al., "Inhibition of p38 mitogen-activated protein kinase and transforming growth factor-beta1/Smad signaling pathways modulates the development of fibrosis in adriamycin-induced nephropathy," *Am. J. Pathol.* 169:1527-1540 (2006); Zhang et al., "The role of the Grb2-p38 MAPK signaling pathway in cardiac hypertrophy and fibrosis," *J. Clin. Invest.* 111:833-841 (2003); Matsuoka et al., "A p38 MAPK inhibitor, FR-167653, ameliorates murine bleomycin-induced pulmonary fibrosis," *Am. J. Physiol. Lung Cell. Mol. Physiol.* 283:L103-112 (2002), which are hereby incorporated by reference in their entirety). Recently, a p38 inhibitor, Esbriet (pirfenidone) ((Moran N., "p38 kinase inhibitor approved for idiopathic pulmonary fibrosis," *Nat. Biotechnol.* 29:301 (2011), which is hereby incorporated by reference in its entirety), was approved for treatment of idiopathic pulmonary fibrosis in Europe, indicating the efficacy of targeting the pathway in fibrosis. While pirfenidone does slow the disease progression of pulmonary fibrosis, it does not stop it, indicating the need for more efficacious drugs.

Interestingly, a recent report demonstrated that p38 was activated by salinomycin in human ovarian cancer (Zhang et al., "Antitumor properties of salinomycin on cisplatin-resistant human ovarian cancer cells in vitro and in vivo: involvement of p38 MAPK activation," *Oncol. Rep.* 29:1371-1378 (2013), which is hereby incorporated by reference in its entirety). However, the concentration of salinomycin used to treat cancer cells was much higher (2-7 uM) compared to the levels used in the preceding Examples (50-250 nM). Thus, the effects of salinomycin on activity of p38 may vary with cell type and treatment concentration. The activity of p38 is regulated by the upstream kinases, MKK3 and MKK6 (FIG. 7) (Raingeaud et al., "MKK3- and MKK6-regulated gene expression is mediated by the p38 mitogen-activated protein kinase signal transduction pathway," *Mol. Cell. Biol.* 16:1247-1255 (1996); Enslen et al., "Selective activation of p38 mitogen-activated protein (MAP) kinase isoforms by the MAP kinase kinases MKK3 and MKK6," *J. Biol. Chem.* 273:1741-1748 (1998), which are hereby incorporated by reference in their entirety). While these two kinases are very similar in sequence and structure, they can often have differential effects on activation of p38 (Tanaka et al., "Differential involvement of p38 mitogen-activated protein kinase kinases MKK3 and MKK6 in T-cell apoptosis," *EMBO Rep.* 3:785-791 (2002), which is hereby incorporated by reference in its entirety). These data in human fibroblasts show that expression and activation of a constitutively active MKK6 attenuate the effect of salinomycin on p38 and myofibroblast formation (FIG. 6). Further analysis of the role of salinomycin in altering MKK3/6 activity will clarify its mechanism of action.

Based on the similar results achieved with three structurally related polyether ionophores, it is believed that all three operate via the same mechanism of action. Salinomycin, its derivative narasin, and the related polyether ionophore, monensin all appear to have powerful anti-myofibroblast activity (FIG. 3). The ability of all three to possess this ability opens up the possibility that polyether ionophore function is required. Polyether ionophores preferentially bind monovalent cations such as sodium and potassium (Antoszczak et al., "Synthesis, cytotoxicity and antibacterial activity of new esters of polyether antibiotic-salinomycin," *Eur. J. Med. Chem.* 76:435-444 (2014), which is hereby incorporated by reference in its entirety). While this may be important in their coccidiostat properties, it is unclear if this is required to block TGFβ function. However, since only nanomolar amounts of these ionophores are required, and there are micromolar levels or more of sodium and potassium ions in culture medium, it appears to be an alternative property of this family of molecules that is unrelated to their activity as ionophores. Development of new analogs of salinomycin, or other polyether ionophores, that alter the polyether moieties will help to elucidate the nature of their anti-TGFβ properties.

Recent publications have reported on the exciting possibility that salinomycin is a powerful therapeutic in combating cancer stem cells (Naujokat et al., "Salinomycin as a drug for targeting human cancer stem cells," *J. Biomed. Biotechnol.* 2012:950658 (2012); Huczynski A., "Salinomycin: a new cancer drug candidate," *Chem. Biol. Drug Des.* 79:235-238 (2012); Wang Y., "Effects of salinomycin on cancer stem cell in human lung adenocarcinoma A549 cells," *Med. Chem.* 7:106-111 (2011); Naujokat et al., "Salinomycin in cancer: A new mission for an old agent," *Mol. Med. Rep.* 3:555-559 (2010), which are hereby incorporated by reference in their entirety). The concept that salinomycin may target highly proliferative cells as opposed to other, more slowly growing cells is also supported by the data showing salinomycin is not toxic to human fibroblasts at the levels needed to blunt myofibroblast formation. Interestingly, salinomycin does not affect basal proliferation of human fibroblasts, but does prevent TGFβ-induced proliferation (FIG. 4). In addition to driving myofibroblast formation, another consequence of high TGFβ levels in fibrosis and scarring are the unwanted proliferative effects (Akhurst et al., "Targeting the TGFbeta signalling pathway in disease," *Nat. Rev. Drug Discov.* 11:790-811 (2012), which is hereby incorporated by reference in its entirety).

Example 4—Characterization of Thy1 Expression in Breast Implant Capsules and its Potential as a Pharmacologic Target to Modulate Scar Formation in Post-Irradiated Women Capsular contracture is a poorly understood complication of radiation treatment following implant-based breast reconstruction. Thy1 (CD90), a glycophosphatadyl inositol membrane anchored glycoprotein, is fundamental to myofibroblast differentiation. Herein, the expression of Thy1 in implant capsule was characterized and tested as a potential pharmacologic target to modulate scar formation in post-irradiated women.

Figure 8:
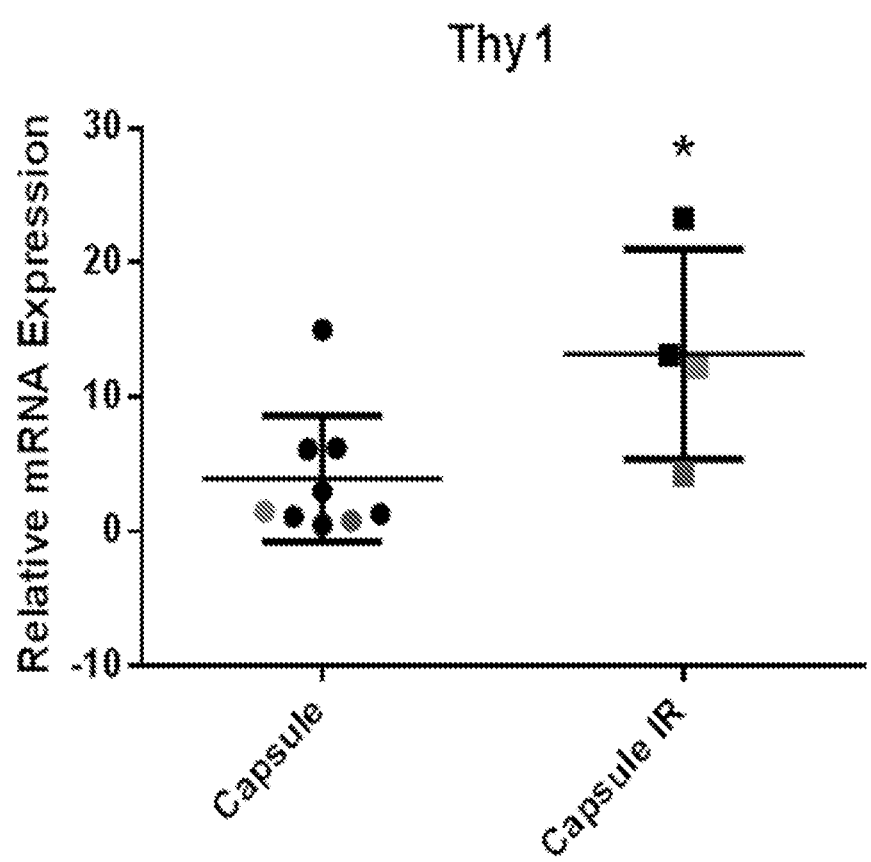
FIG. 8 is a graph showing Thy1 expression in whole tissue specimens obtained from thirteen women during implant revision surgeries. Tissue was classified as either non-irradiated (Capsule, n=9) or irradiated (Capsule IR, n=4). Following tissue homogenization, cells were lysed and mRNA was extracted for qPCR analysis of Thy1 levels. Results demonstrate that Thy1 expression is significantly greater in irradiated capsular tissue. Colored data points represent matched samples, taken from a single patient having undergone unilateral radiation. *=p<0.05.
Figure 9:
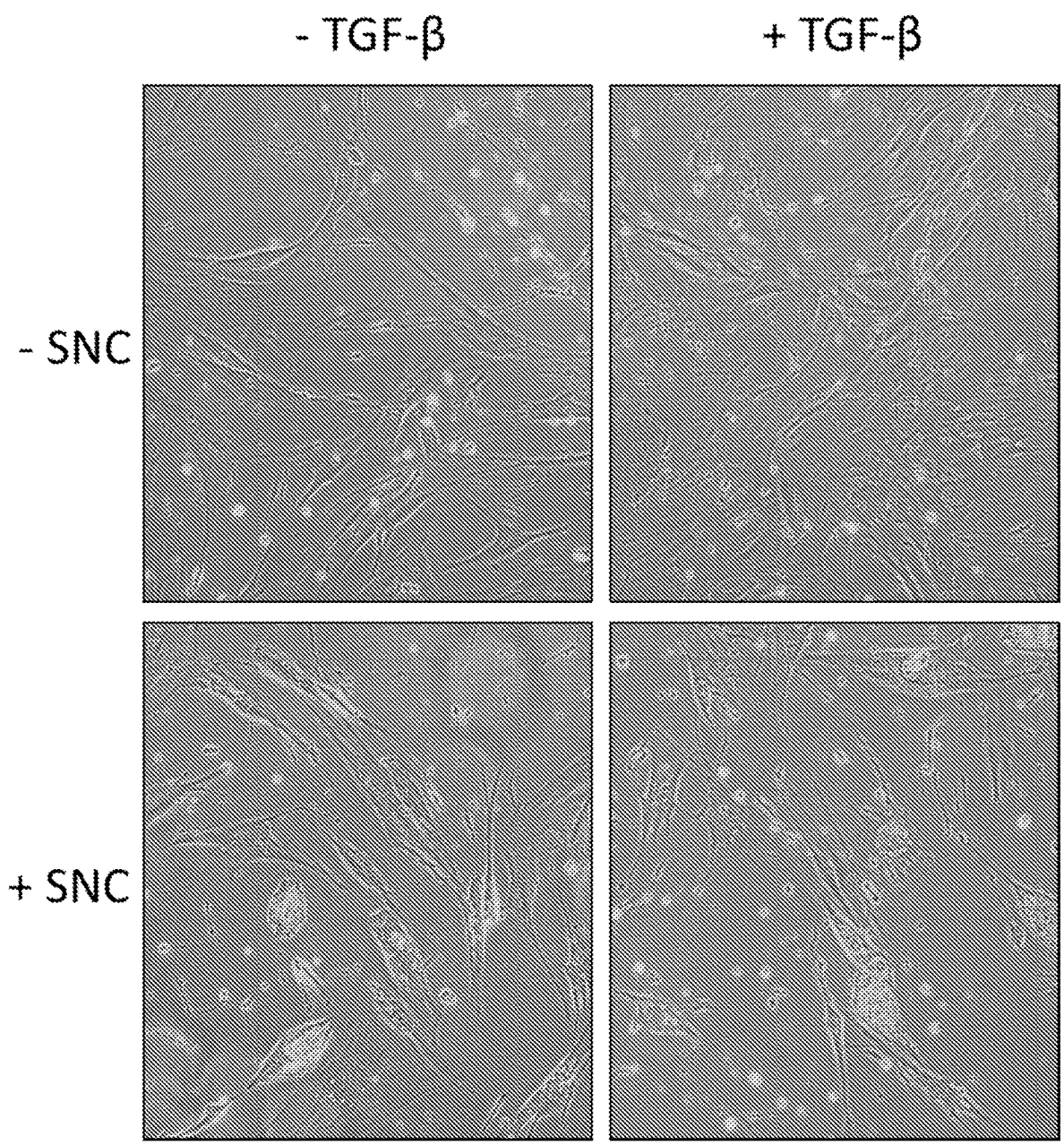
FIG. 9 is a set of images of capsular fibroblasts explanted from primary tissue samples cultured in vitro. Treatment consisted of 48 hours growth in serum-starved media (0.1% fetal bovine serum), followed by administration of vehicle, 2.5 ng/mL transforming growth factor-beta (TGF-β), 250 nM salinomycin (SNC), or TGF-β plus SNC for 72 hours. At this time point, TGF-β treated cells show increased density and a more flattened, spiculated morphology suggestive of myofibroblastic differentiation relative to the untreated cells. The concomitant addition of SNC appears to reduce the effect of TGF-β on the fibroblasts. Original magnification 200×.
Figure 10A:
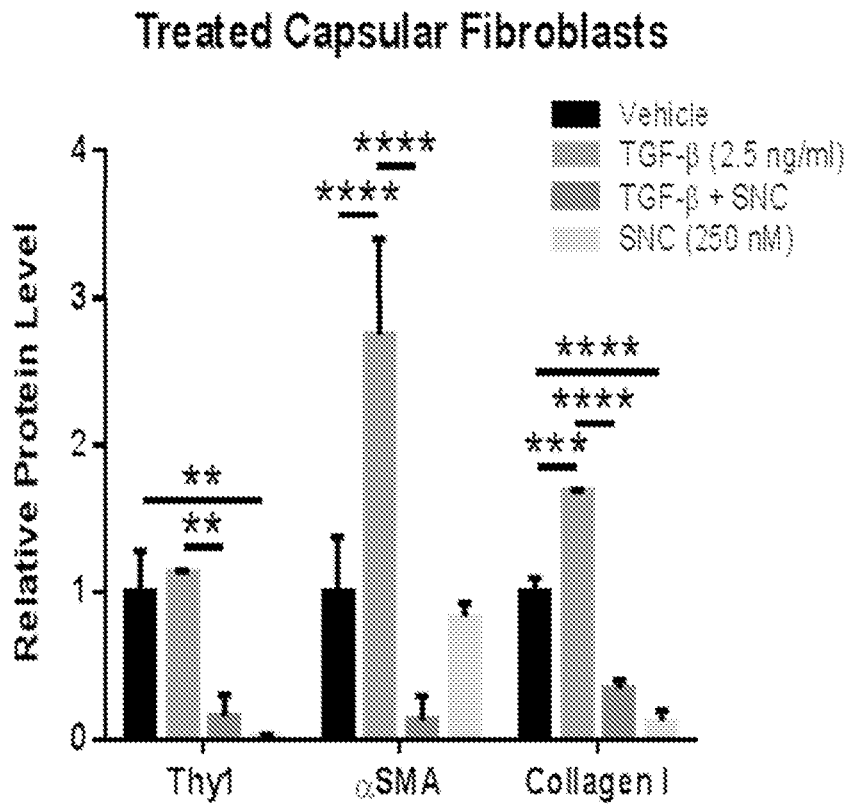
FIGS. 10A-B shows a representative fibroblast strain explanted from primary capsular tissue and treated with 2.5 ng/mL transforming growth factor-beta (TGF-β), 250 nM salinomycin (SNC), or TGF-β plus SNC for 72 hours. After treatment, cells were lysed for protein extraction and analysis via Western blot. Data are presented in graph form (FIG. 10A) and as images of Western blots (FIG. 10B). Though lacking a significant induction following treatment with TGF-β, Thy1 expression was significantly reduced with SNC. Alpha-SMA expression increased nearly 3-fold with TGF-β, but concomitant SNC treatment decreased expression to below basal levels. All protein expression is relative to β-tubulin levels. At time of cell harvest, media supernatant was also taken and equal volumes run on a slot blot to compare presence of extracellular soluble collagen. In like manner, collagen I increased with TGF- and was reduced with co-administration of SNC. =p<0.01; *=p<0.001; ****=p<0.0001.
Figure 10B:
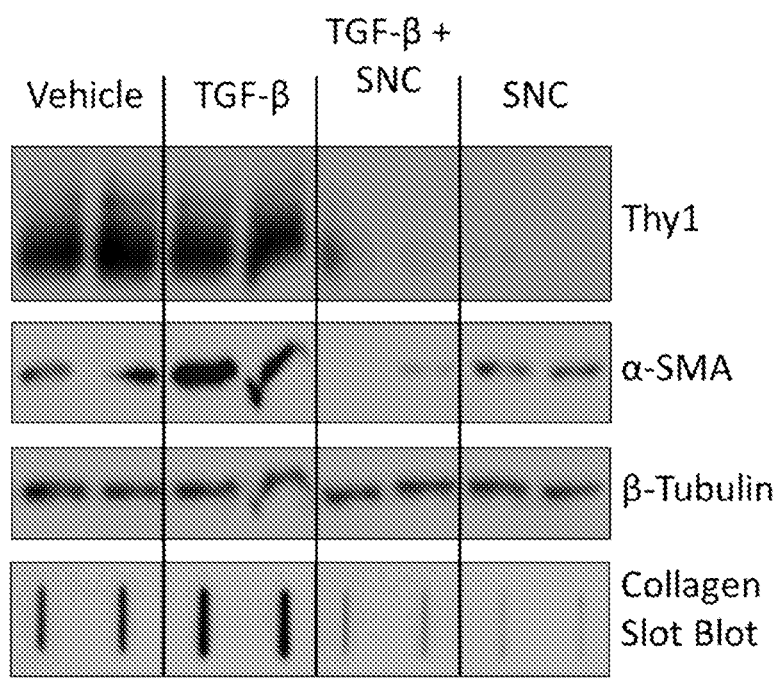
Figure 11A:
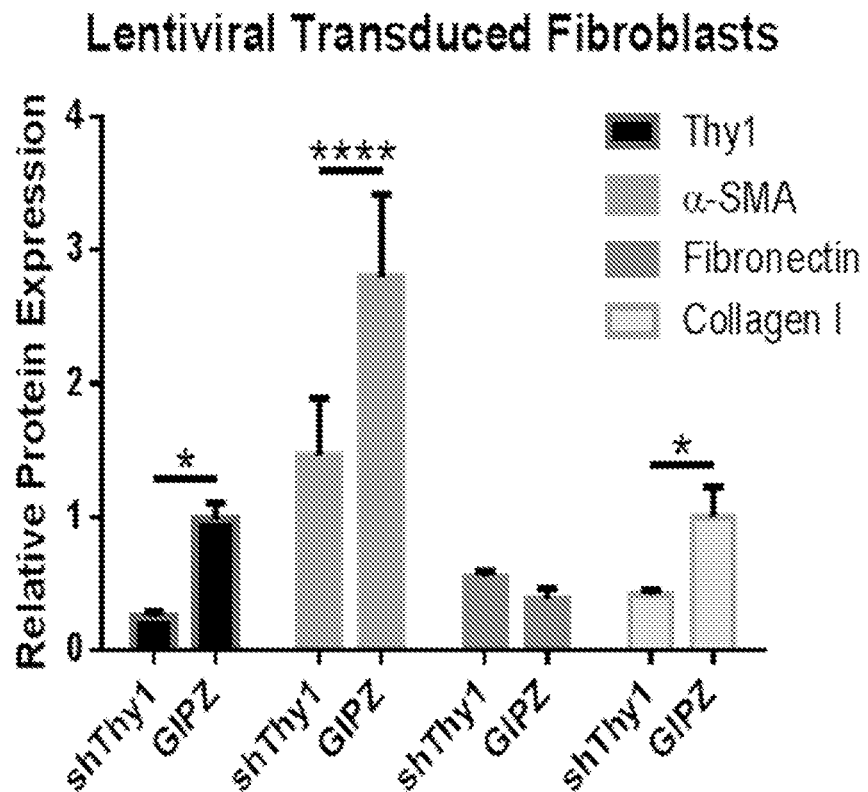
FIGS. 11A-B show, using a lentiviral vector, fibroblasts transduced with either a plasmid to reduce basal expression of Thy1 (shThy1) or a control plasmid (GIPZ). Transduced cells were selected using antibiotic resistance (Puromycin at 2 ug/mL). Cells were then grown to confluency and harvested for analysis via Western blot. Data are presented in graph form (FIG. 11A) and as images of Western blots (FIG. 11B). shThy1 cells showed a reduction of approximately 80% in basal Thy1 expression. These cells also had reduced expression of both alpha-SMA and extracellular soluble collagen type I. Interestingly, fibronectin levels, another constituent of scar tissue, appears to inversely correlate with Thy1 expression, though these results did not reach significance. All results are relative to β-tubulin and normalized to a positive control. *=p<0.05; ****=p<0.0001.
Figure 11B:
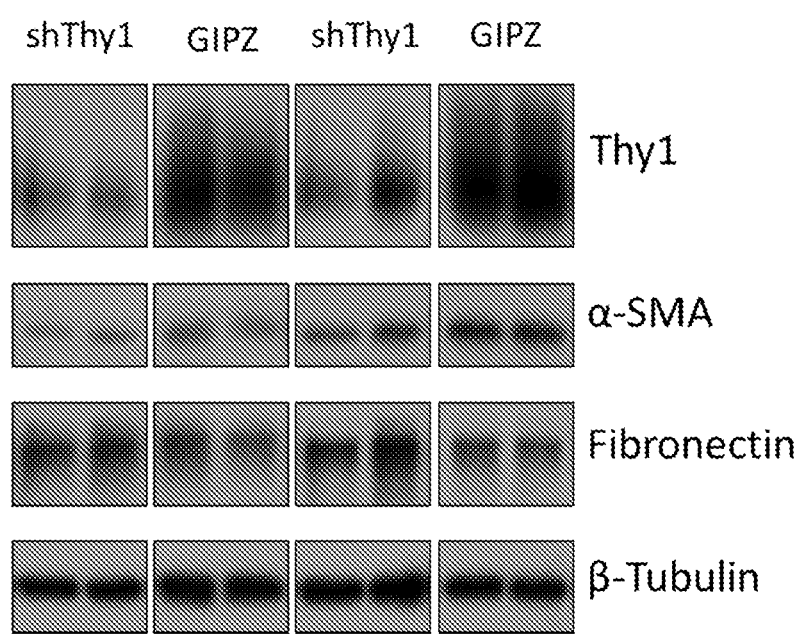

Peri-implant tissue samples from irradiated (n=4) and non-irradiated (n=9) breast capsules were analyzed for expression of Thy1 mRNA by qRT-PCR (FIG. 8). Additionally, capsular fibroblasts were grown in vitro and treated with the pro-fibrotic cytokine transforming growth factor-β (TGFβ) and the polyether ionophore salinomycin, and analyzed for expression of Thy1, αSMA, fibronectin, and collagen by Western blot (FIG. 9 and FIGS. 10A-B). To investigate the fundamental role of Thy1 in capsular fibroblast/myofibroblast formation, Thy1 expression was depleted using Thy1 siRNA (delivered by lentiviral transduction) (FIGS. 11A-B).

RT-qPCR analysis revealed that irradiated capsule contained more Thy1 mRNA than non-irradiated samples (13.2 vs. 4.0, P=0.02) (FIG. 8). Western blot analysis showed that explanted fibroblasts treated with TGFβ expressed increased αSMA and collagen I, which was nearly completely inhibited by salinomycin treatment (FIGS. 10A-B). Salinomycin dramatically reduced the expression of Thy1 in both untreated and TGFβ treated cultures. Direct knockdown of Thy1 by Thy1 siRNA reduced capsular fibroblast/myofibroblast expression of αSMA and collagen I (FIGS. 11A-B).

In conclusion, irradiated breast capsules express more Thy1 than non-irradiated breast capsule, indicating a seminal role for Thy1 in capsule scar formation. Further, explant fibroblast cultures treated with TGFβ showed increased production of collagen and αSMA, which was reduced by salinomycin treatment. Direct knockdown of Thy1 by Thy1 siRNA also reduced capsular culture expression of collagen and αSMA. These studies demonstrate that myofibroblast differentiation is important in capsular contracture and molecular targeting of Thy1 by salinomycin or other small molecules, including other polyether ionophores, should reduce capsular contracture following radiation. It is expected that salinomycin and other polyether ionophores will be effective for controlling capsular contracture and inhibiting scar formation in reconstructed breast tissue in post-irradiated women.

Example 5—Dose Responsiveness of Other Compounds from the Spectrum Collection

Figure 12:
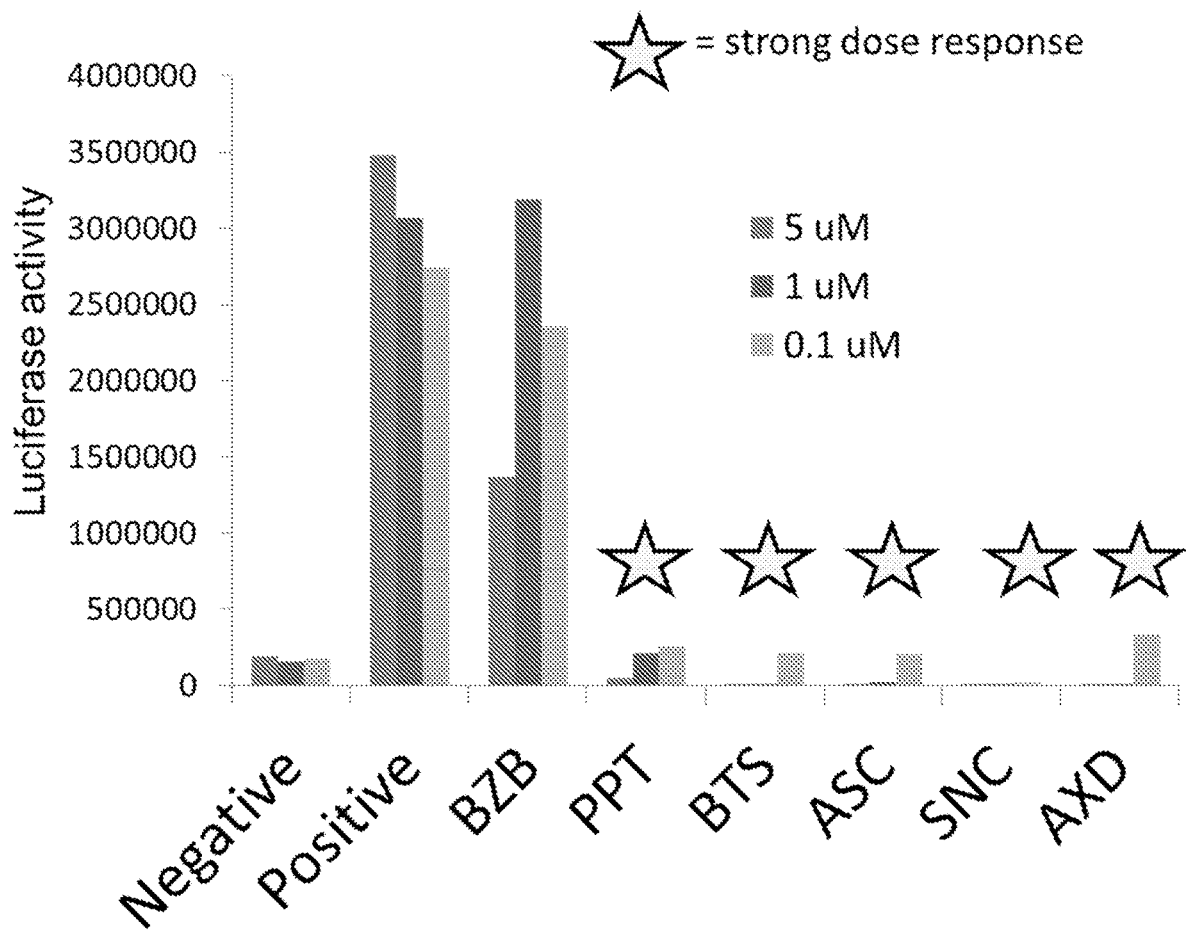
FIG. 12 is a graph showing results from a secondary luciferase screen, which was performed to determine specificity and dose responsiveness of the six best small molecule hits from initial screening of the Spectrum library for TGFβ inhibition. The compounds are benzbromarone ("BZB"), bithionate sodium ("BTS"), piplartine (piperlongumine) ("PPT"), amsacrine ("ASC"), alexidine ("AXD"), and salinomycin ("SNC"). All but BZB substantially inhibited luciferase expression at one or more of the doses tested.

The initial Spectrum Collection screen identified five other compounds, beside salinomycin, that inhibit TGFβ-induced luciferase in the luciferase screening assay described in the preceding Examples. They are: Benzbromarone ("BZB"), Bithionate sodium ("BTS"), Piplartine (piperlongumine) ("PPT"), Amsacrine ("ASC"), and Alexidine ("AXD"). A secondary luciferase screening assay was performed to determine specificity and dose responsiveness of these compounds in comparison to salinomycin ("SNC"). The secondary screen utilizes dual luciferase technology that includes the above mentioned SBE-luciferase in addition to a *Renilla* luciferase that is under control of the constitutive SV40 promoter. Therefore the SBE-luciferase activity can be normalized to the *Renilla* luciferase activity to control for toxicity and non-specific effects. The secondary screen can thus be used to remove small molecules that display overt toxicity and/or non-specific effects on the primary assay. Of these five compounds tested in the secondary screen, BTS, PPT, ASC, and AXD all exhibited strong luciferase inhibition at low micromolar levels (FIG. 12).

Figure 13:
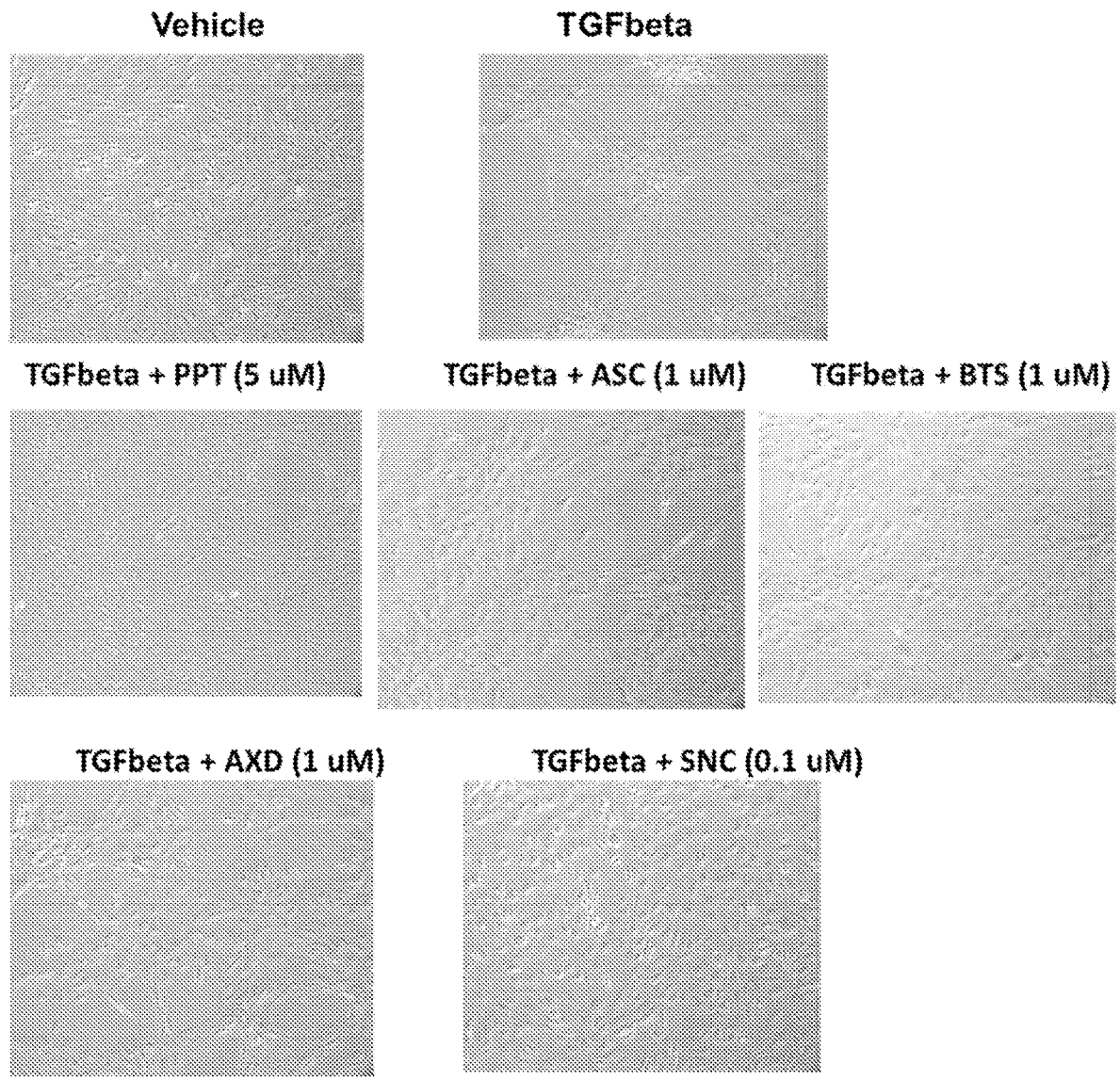
FIG. 13 is a panel of images showing that BTS, PPT, ASC, AXD, and SNC inhibit TGFβ-dependent myofibroblast (scar cells) formation in primary human fibroblasts. Myofibroblast phenotype was observed in TGFβ treated cells. All five small molecule hits inhibit myofibroblast phenotype at the lowest effective dose from FIG. 12.

The four compounds that displayed strong luciferase inhibition in the secondary screening assay were assessed for their ability to inhibit TGFβ-dependent myofibroblast formation. Using the lowest effective dose from the secondary screening assay, PPT (5 µM), ASC (1 µM), BTS (1 µM), and AXD (1 µM) were compared to 0.1 µM SNC using primary human fibroblasts (FIG. 13). The myofibroblast formation assay consists of the following protocol: fibroblasts are treated with the aforementioned small molecules and treated with TGFβ (1 ng/ml) for 72 hours. The cells were then either photographed for morphological analysis or collected, lysed and analyzed by Western blot for the myofibroblast markers alpha-smooth muscle actin (αSMA) and calponin. β-tubulin was used as a loading control. Each of PPT (5 M), ASC (1 µM), BTS (1 µM), and AXD (1 µM) inhibits myofibroblast formation.

Figure 14:
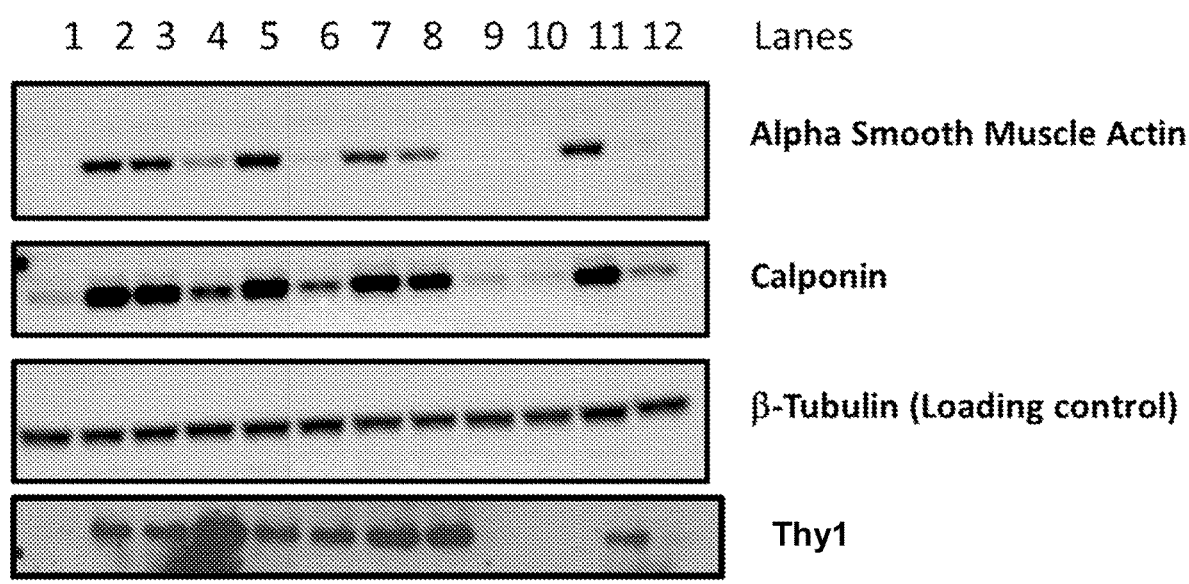
FIG. 14 shows Western blot results that demonstrate that BTS, PPT, ASC, AXD, and SNC inhibit β-dependent α-SMA and calponin expression in human fibroblasts. Lanes: 1. vehicle; 2. TGFb; 3. TGFb+PPT (1 uM); 4. TGFb+PPT (5 uM); 5. TGFb+BTS (0.1 uM); 6. TGFb+BTS (1 uM); 7. TGFb+ASC (0.1 uM); 8. TGFb+ASC (1 uM); 9. TGFb+SNC (100 nM); 10. TGFb+SNC (1 uM); 11. TGFb+AXD (0.1 uM); and 12. TGFb+AXD (1 uM).

Western blots were also performed using cell lysates from the primary human fibroblasts exposed to TGFβ to assess TGFβ-dependent αSMA and calponin expression. PPT was used at 1 and 5 µM (lanes 3 and 4), BTS was used at 0.1 and 1 µM (lanes 5 and 6), ASC was used at 0.1 and 1 µM (lanes 7 and 8), SNC was used at 100 nM and 1 µM (lanes 9 and 10), and AXD was used at 0.1 and 1 µM (lanes 11 and 12). The results, shown in FIG. 14, demonstrate that PPT, BTS, ASC, and AXD inhibited marker expression at their higher doses, whereas SNC was effective even at the lower dose. SNC also inhibits expression of Thy1 at both doses, demonstrating it works through a unique mechanism. AXD did inhibit Thy1 at its high dose.

Figure 15:
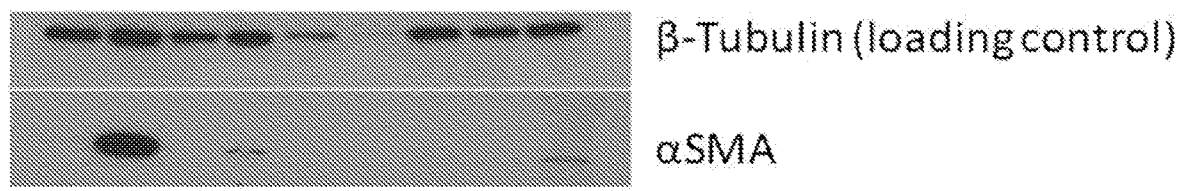
FIG. 15 shows relative αSMA expression in human orbital fibroblasts. Human orbital fibroblasts were treated with various concentrations of 10-hydroxycamptothecin (HCPT) (50 nM to 500 nM) and induced to form scar-forming myofibroblasts by treating with TGFβ. αSMA serves as a marker for myofibroblast formation while β-tubulin is a control protein. Salinomycin (SNC) and alexidine (AXD) serve as positive controls for anti-fibrotic activity. HCPT potently blocks myofibroblast formation.
Figure 15:
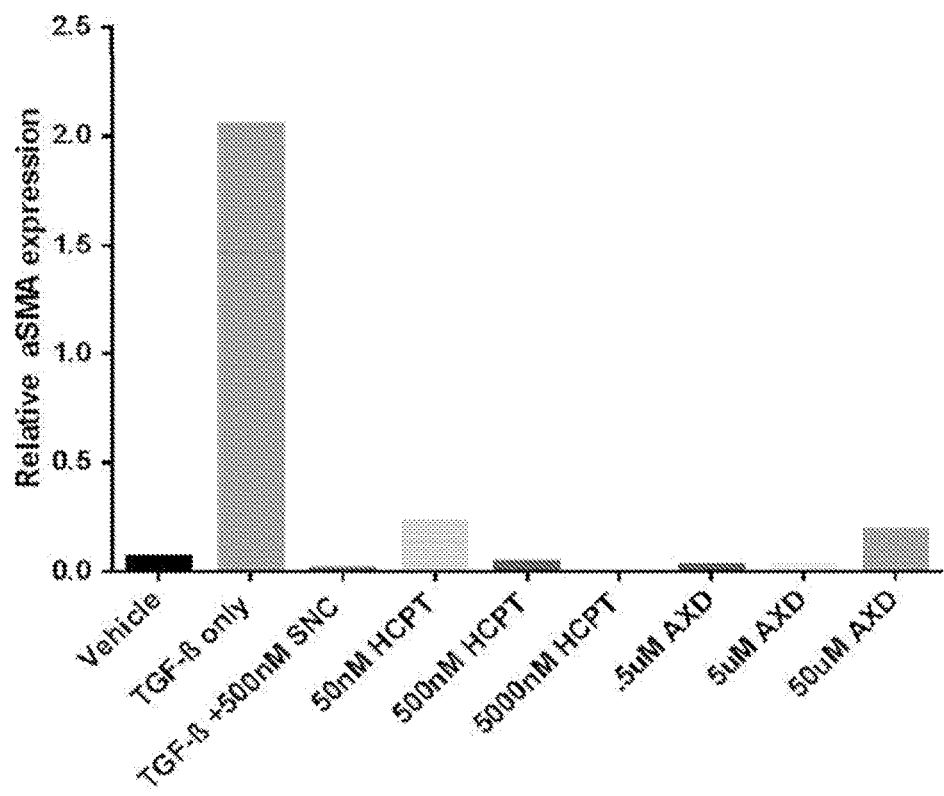
Figure 16:
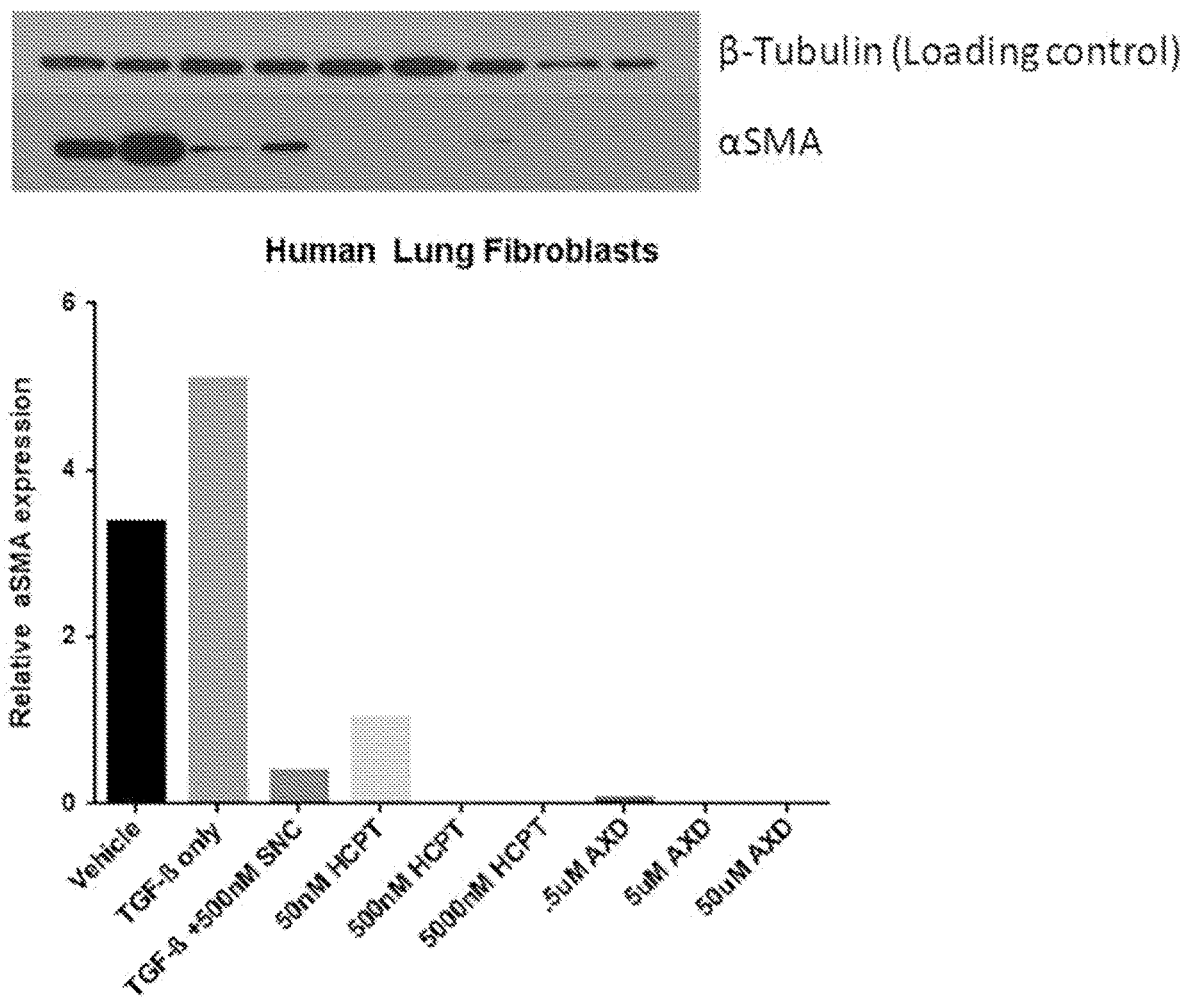
FIG. 16 shows relative αSMA expression in human lung fibroblasts. Human lung fibroblasts were treated with various concentrations of 10-hydroxycamptothecin (HCPT) (50 nM to 500 nM) and induced to form scar-forming myofibroblasts by treating with TGFβ. αSMA serves as a marker for myofibroblast formation while β-tubulin is a control protein. Salinomycin (SNC) and alexidine (AXD) serve as positive controls for anti-fibrotic activity. HCPT potently blocks myofibroblast formation.

Example 6—Assessing Efficacy of 10-Hydroxycamptothecin (HCPT) to Inhibit TGFβ-Induced Myofibroblast Formation Primary human orbital fibroblasts, primary human lung fibroblasts, and primary mouse lung fibroblasts were treated with TGFβ and HCPT (50 nM, 500 nM, and 5000 nM) or SNC (500 nM) or AXD (0.5 µM, 5 µM, and 50 µM) to assess the ability of HCPT to inhibit myofibroblast formation. Salinomycin and alexidine served as positive controls for anti-fibrotic activity. Western blots were performed using cell lysates from the fibroblasts exposed to TGFβ to assess TGFβ-dependent αSMA expression. As shown in FIGS. 15 and 16, HCPT potently blocks myofibroblast formation and exhibits a dose-dependent inhibition of αSMA in both human orbital and lung fibroblasts.

Figure 17:
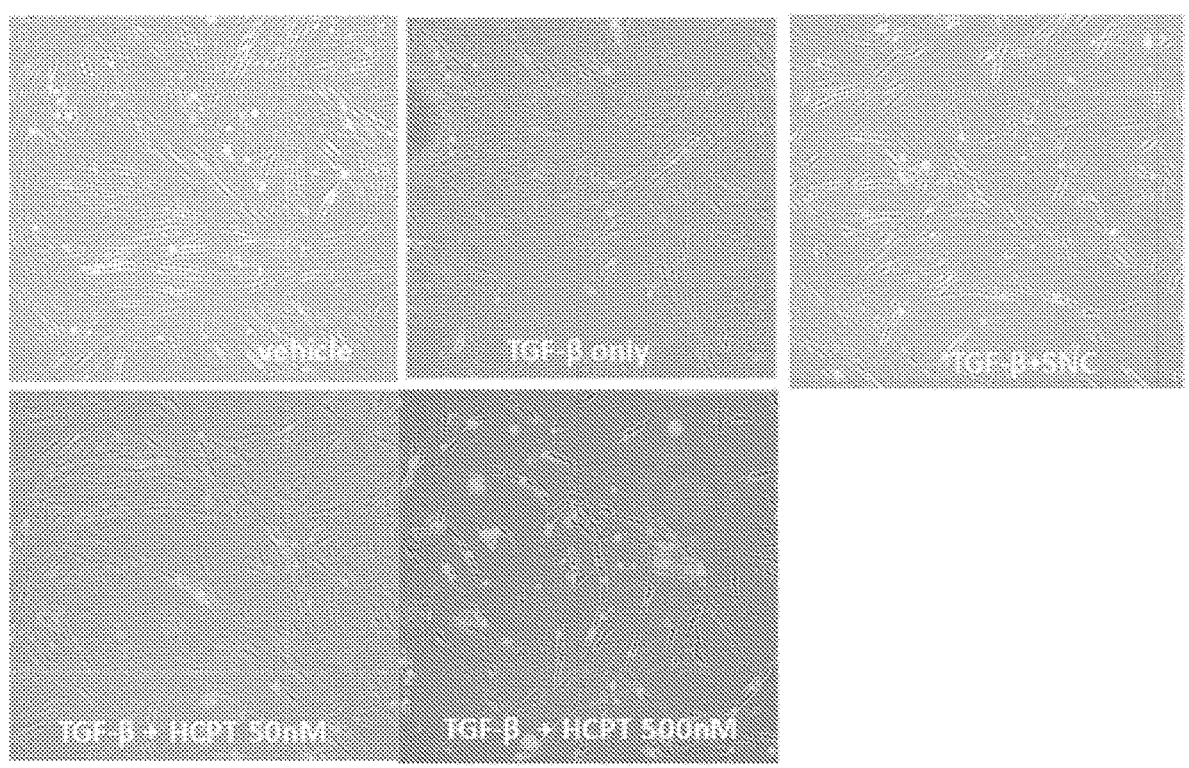
FIG. 17 is a panel of images that show the formation of myofibroblasts. Human lung fibroblasts were treated with various concentrations of 10-hydroxycamptothecin (HCPT) (50 nM or 500 nM) and induced to form scar-forming myofibroblasts by treating with TGFβ. Cells images were captured to show formation of myofibroblast in TGFβ treated samples but not in samples treated with HCPT or SNC. HCPT potently blocks myofibroblast formation without being overtly toxic, as cell pictures show viable fibroblasts in HCPT treated cultures.

Cells images related to the formation of myofibroblasts are shown in FIG. 17. Human lung fibroblasts were treated with various concentrations of 10-hydroxycamptothecin (HCPT) (50 nM or 500 nM) and induced to form scar-forming myofibroblasts by treating with TGFβ. Cells images were captured to show formation of myofibroblast in TGFβ treated samples but not in samples with HCPT or salinomycin (SNC). HCPT potently blocks myofibroblast formation with out being overtly toxic as cell pictures show viable fibroblasts in HCPT treated cultures.

Figure 18:
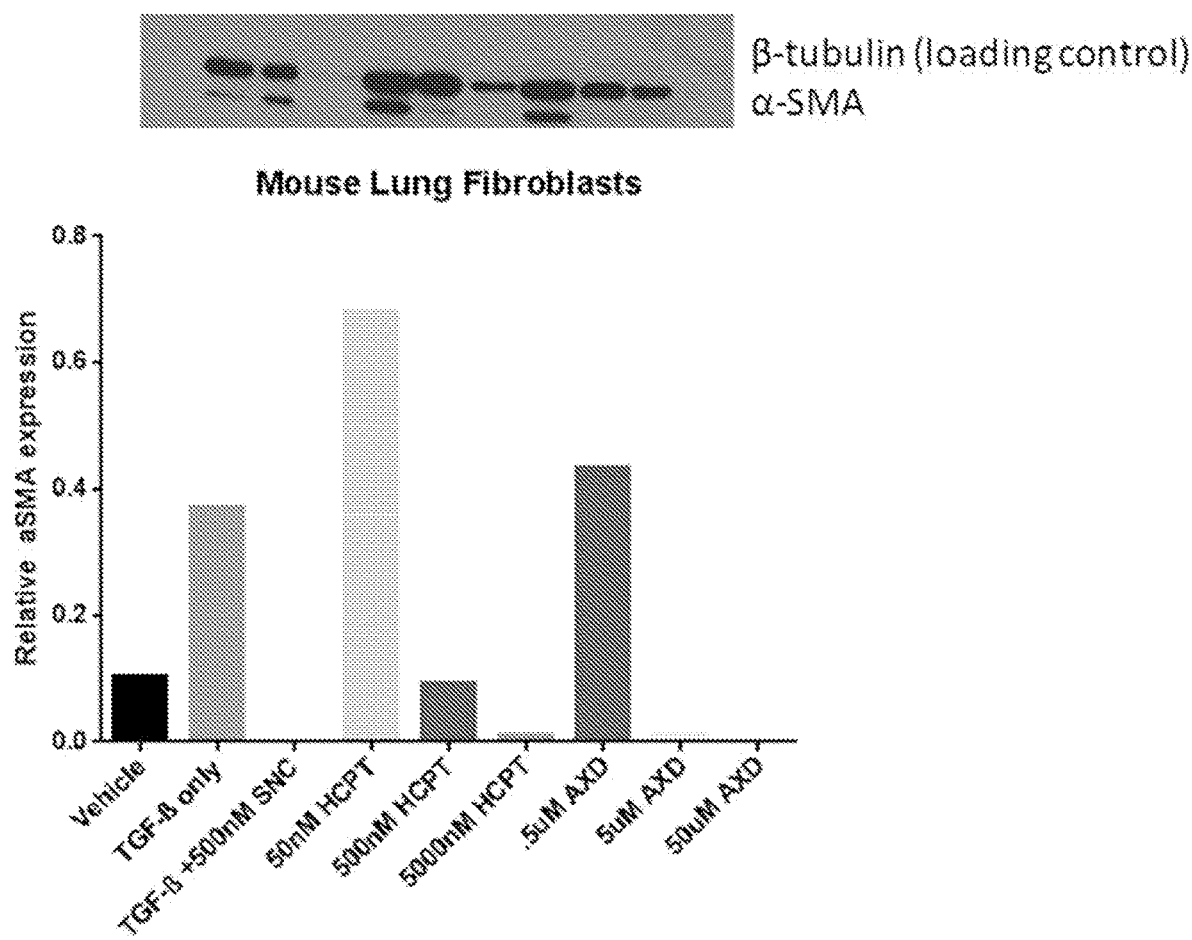
FIG. 18 shows relative αSMA expression in mouse lung fibroblasts. Mouse lung fibroblasts were treated with various concentrations of 10-hydroxycamptothecin (HCPT) (50 nM to 500 nM) and induced to form scar-forming myofibroblasts by treating with TGFβ. αSMA serves as a marker for myofibroblast formation while β-tubulin is a control protein. Salinomycin (SNC) and alexidine (AXD) serve as positive controls for anti-fibrotic activity. HCPT potently blocks myofibroblast formation.

Similar dose-dependent responses were observed in mouse lung fibroblasts, although HCPT was less effective in blocking myofibroblast formation of mouse fibroblasts (compare FIG. 18 to FIGS. 15-16).

Figure 19:
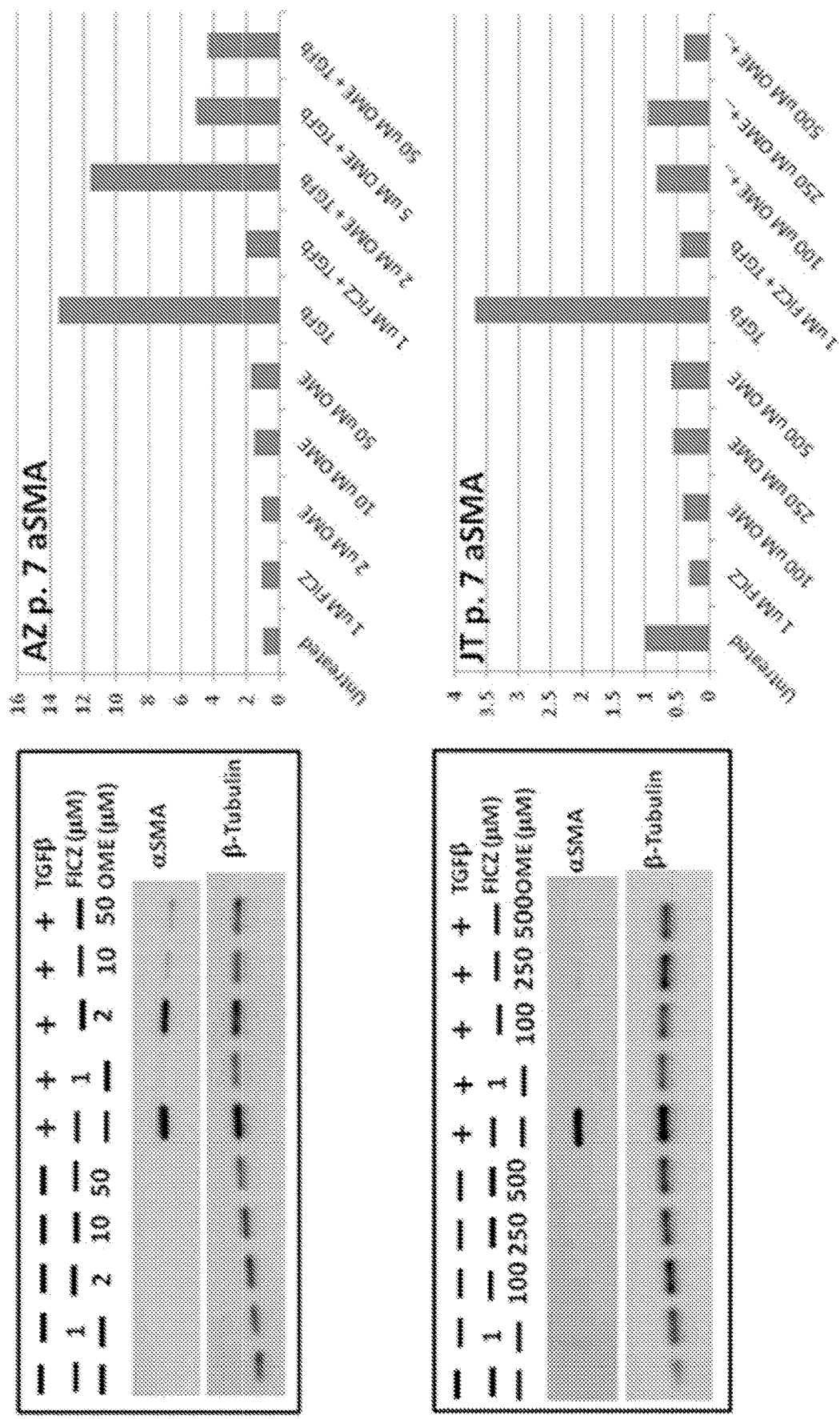
FIG. 19 is a set of Western blot results and corresponding graphs showing that omeprazole inhibits human orbital fibroblast to myofibroblast differentiation. αSMA serves as a marker for myofibroblast formation while β-tubulin is a control protein.
Figure 20:
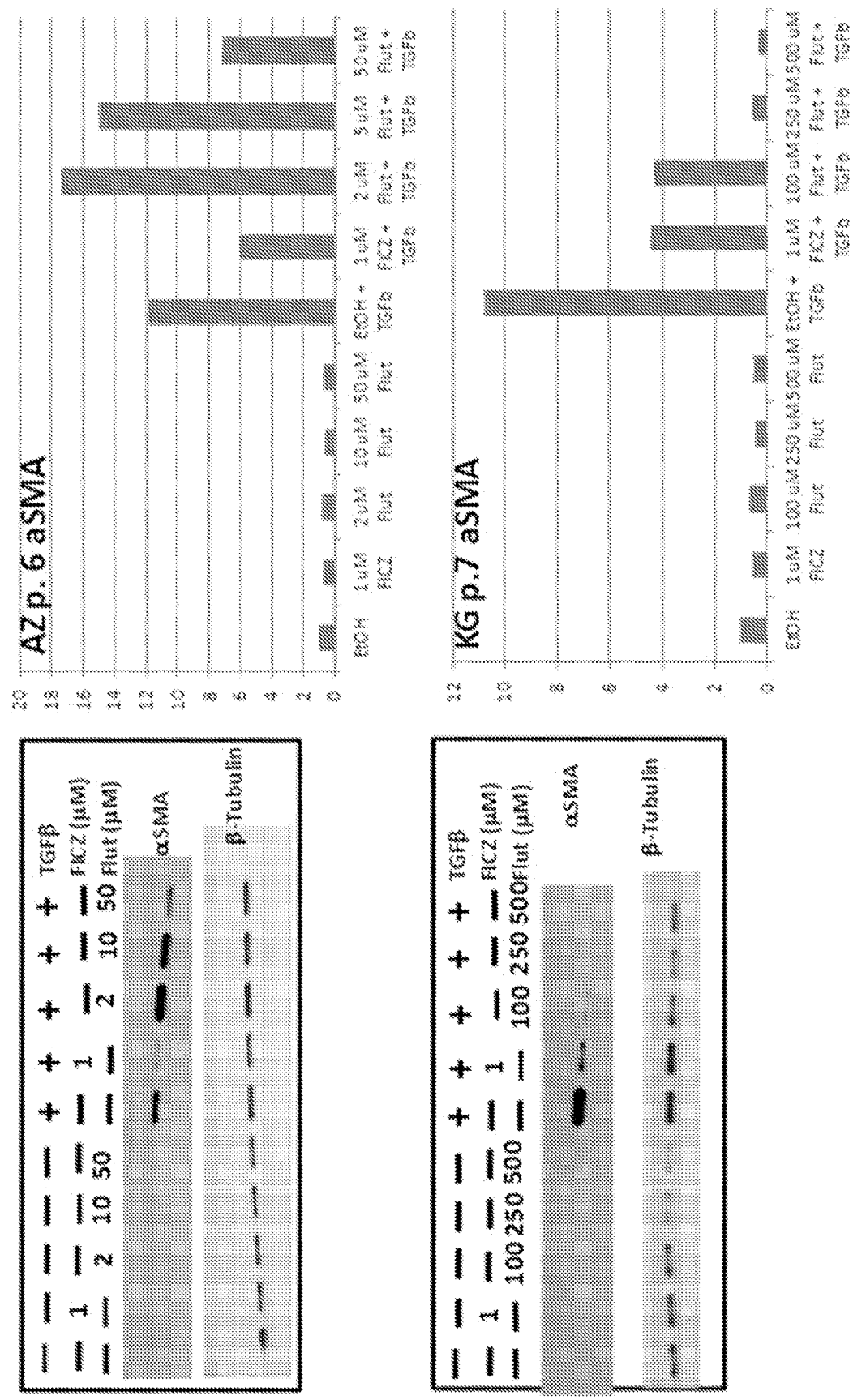
FIG. 20 is a set of Western blot results and corresponding graphs showing that flutamide inhibits human orbital fibroblast to myofibroblast differentiation. αSMA serves as a marker for myofibroblast formation while β-tubulin is a control protein.

Example 7—Assessing Efficacy of Omeprazole and Flutamide to Inhibit TGFβ-Induced Myofibroblast Formation Primary human orbital fibroblasts were treated with TGFβ and either 6-formylindolo(3,2-b)carbazole ("FICZ", 1 µM), Omeprazole ("Ome", 2 µM, 10 µM, 50 µM, 100 µM, 250 µM, 500 µM), or Flutamide ("Flut", 2 µM, 10 µM, 50 µM, 100 µM, 250 µM, 500 µM) to assess their ability to inhibit myofibroblast formation. FICZ was included as a positive control that blocks myofibroblast formation. Western blots were performed using cell lysates from the fibroblasts exposed to TGFβ to assess TGFβ-dependent αSMA expression. Densitometry analyses of the Western blots were also performed. The results demonstrate that omeprazole (FIG. 19) and flutamide (FIG. 20) inhibited TGFβ-induced myofibroblast differentiation of human orbital fibroblasts in a dose dependent manner. Omeprazole reduced αSMA expression to sub-baseline levels at 100 100 µM (FIG. 19). No overt toxicity was observed.

Example 8—Chembridge Collection Screen

Figure 21:
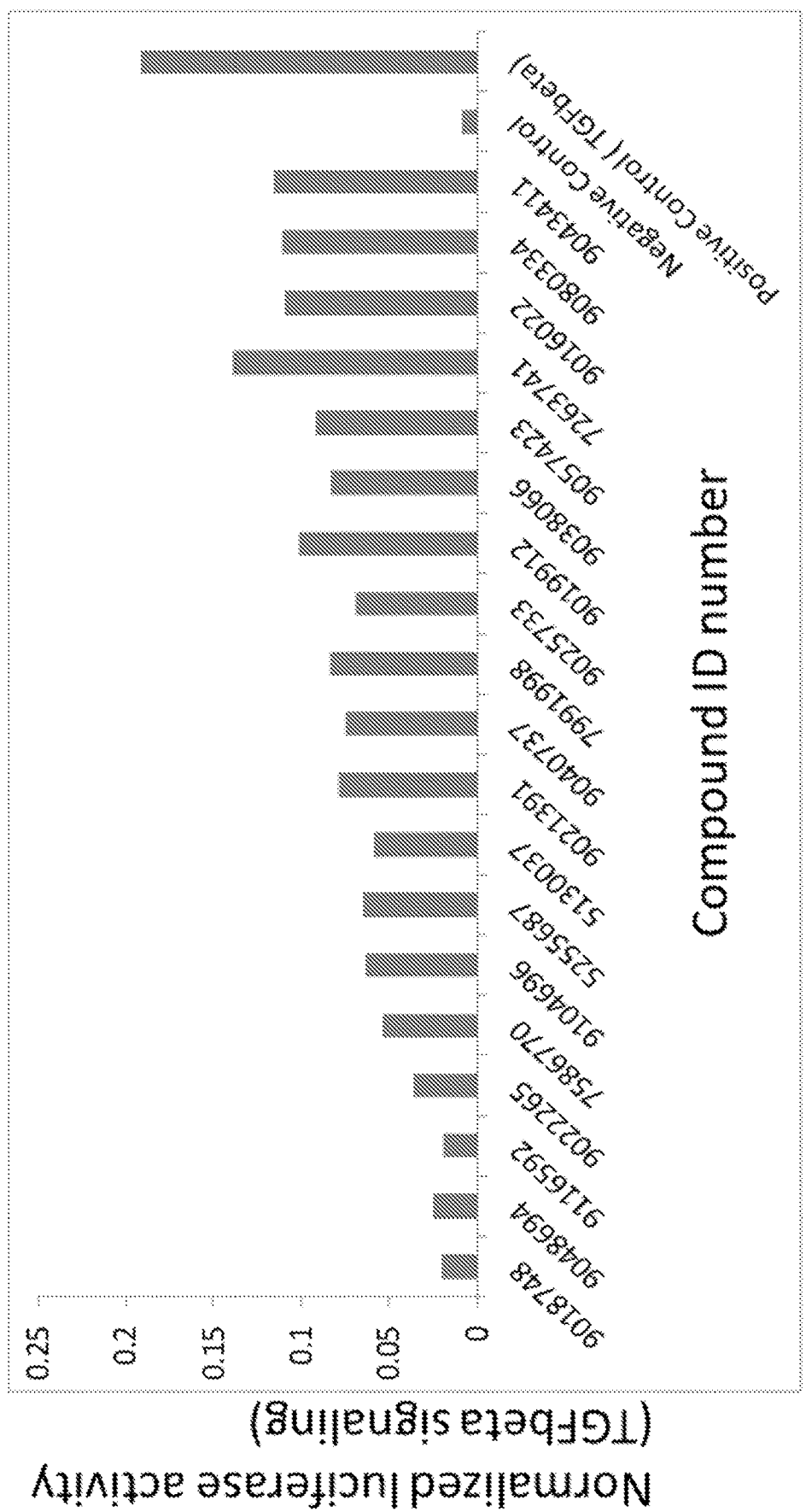
FIG. 21 is a graph showing normalized luciferase activity (TGFβ signaling) for 19 compounds that were discovered from screening the Chembridge library. Chemical ID Nos. are shown. The structures and names of these compounds are shown in Table I presented in the Examples.

Using the recombinant HEK293-Thy1 SBE-Luc cell line described in the preceding Examples, the Chembridge collection of 20,000 small molecules was screened to identify other small molecules that inhibit TGFβ activity and, thus, may be novel anti-scarring compounds The Chembridge screen revealed several potential anti-scarring compounds. 100 top candidates from the initial screen were re-screened. Results from this screen are shown in FIG. 21. Numbers indicate the Chembride molecule ID number. The second screen controls for toxicity and non-specific effects by using a constitutive luciferase to normalize results. This assay can be further used in a high throughput fashion to analyze newly derived compounds and monitor structure activity relationships (SAR) to discover new molecules that can serve as the basis for anti-scarring therapeutics.

Figure 22:
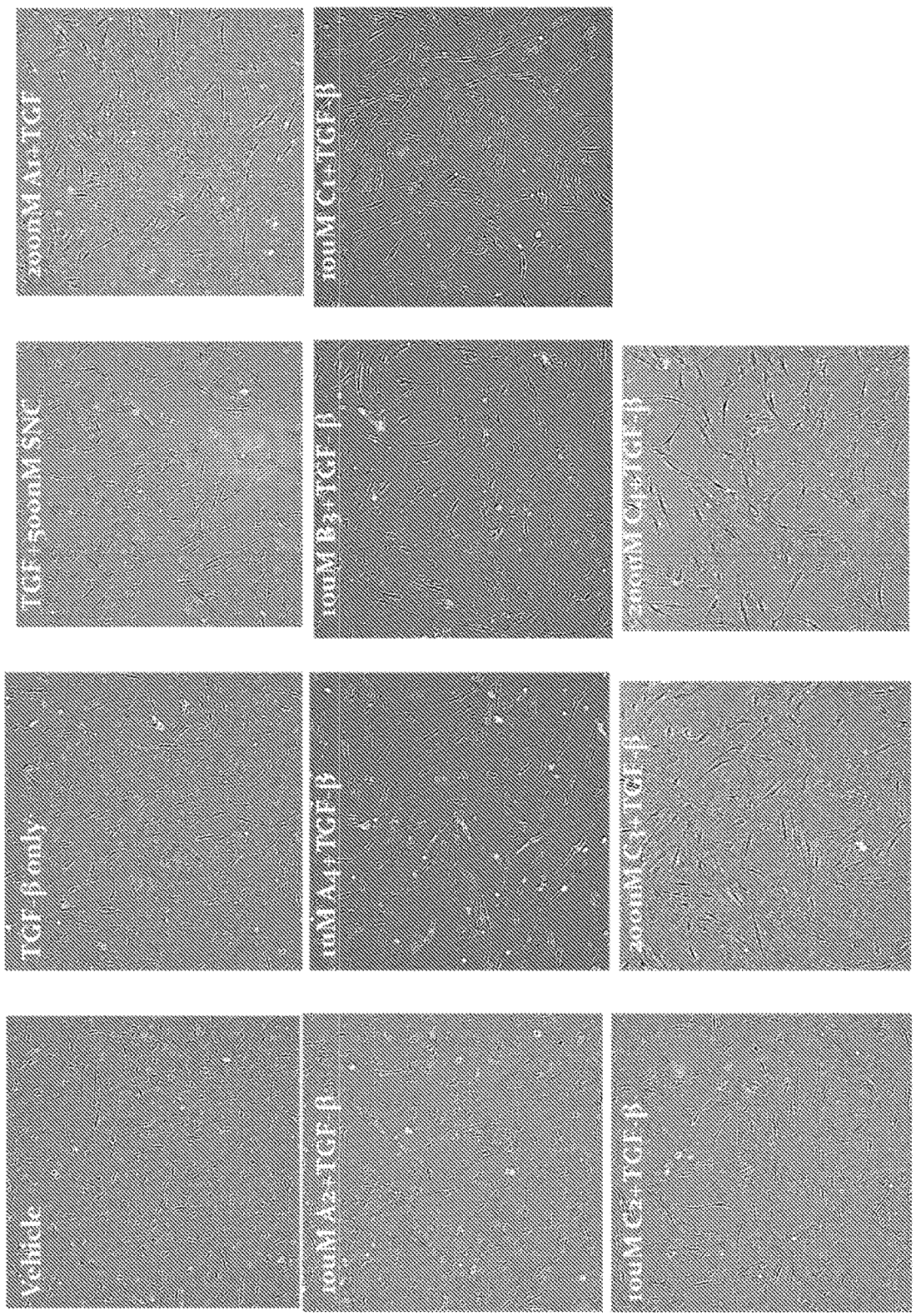
FIG. 22 is a panel of cell images showing efficacy of selected Chembridge hits in myofibroblast formation assays using human orbital fibroblasts. These cell images show the powerful effect of these small molecules in preventing TGFβ induced myofibroblast formation while not causing cell death. Key: SNC: salinomycin control; A1: 5255687; A2:5130037; A4:9040737; B3:9057423; C2:9018748; C3:9048694; C4:9022265.

The 19 compounds listed in Table 1 are excellent inhibitors of TGFβ signaling that do not display overt cytotoxic effects. The two-dimensional structures of the molecules are depicted in the left hand column. Chembridge collection IDs are listed in the second column and the additional columns denote the following (in order): the molecular name, the percent inhibition of the molecule using the screen (100% being a complete inhibition) (% Inhib.), and the internal key (key) for further identification in FIGS. 22 and 23.

TABLE 1

| Hits found in Chembridge collection (20,000 compounds) screen ||||| 
|---|---|---|---|---|
| Structure | ID | Mol Name | % Inhib. | Key |
| [structure] | 9018748 | 4,5-dichloro-2-methyl-N-(4-pyridinylmethyl)benzenesulfonamide | 95% | C2 |
| [structure] | 9048694 | N-(2-methoxyphenyl)-3-phenyl-2-propynamide | 92% | C3 |

TABLE 1-continued

| Hits found in Chembridge collection (20,000 compounds) screen | | | | |
|---|---|---|---|---|
| Structure | ID | Mol Name | % Inhib. | Key |
| | 9116592 | 3-amino-4-chloro-N,N-diethylbenzamide | 92% | n/a |
| | 9022265 | 4-ethoxy-2,3-dimethyl-N-(4-pyridinylmethyl)benzenesulfonamide | 84% | C4 |
| | 7586770 | {5-[(4-chlorophenyl)thio]-2-furyl}methanol | 80% | C5 |
| | 9104696 | N-(1-phenylethyl)[1]benzofuro[3,2-d]pyrimidin-4-amine hydrochloride | 75% | C6 |
| | 5255687 | 3-[3-(2-chlorophenyl)acryloyl]-4,6-dimethyl-2(1H)-pyridinone | 70% | A1 |
| | 5130037 | ethyl 2-amino-7-(hydroxyimino)-4,5,6,7-tetrahydro-1-benzothiophene-3-carboxylate | 68% | A2 |
| | 9021391 | 4-fluoro-3-methyl-N-(4-pyridinylmethyl)benzenesulfonamide | 66% | A3 |

TABLE 1-continued

| Hits found in Chembridge collection (20,000 compounds) screen | | | | |
|---|---|---|---|---|
| Structure | ID | Mol Name | % Inhib. | Key |
| | 9040737 | 3-(4-fluorophenyl)-2-methyl-5-phenylpyrazolo[1,5-a]pyrimidin-7(4H)-one | 63% | A4 |
| | 7991998 | N-[4-(allyloxy)phenyl]-4-(4-morpholinomethyl)benzamide | 60% | A5 |
| | 9019912 | 3-fluoro-N-(4-pyridinylmethyl)benzenesulfonamide | 58% | B1 |
| | 9038066 | N-{4-[(tert-butylamino)sulfonyl]phenyl}isonicotinamide | 54% | B2 |
| | 9057423 | N-methyl-2-(2-phenoxyethoxy)benzamide | 51% | B3 |
| | 7263741 | N-1H-benzimidazol-2-yl-2-bromobenzamide | 46% | B4 |
| | 9016022 | 3-benzyl-N-(4-methylphenyl)-7H-[1,2,4]triazolo[3,4-b][1,3,4]thiadiazin-6-amine | 46% | B5 |

TABLE 1-continued

Hits found in Chembridge collection (20,000 compounds) screen

| Structure | ID | Mol Name | % Inhib. | Key |
|---|---|---|---|---|
| 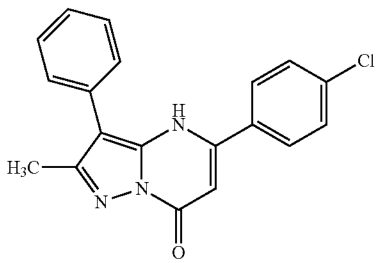 [SMILES: Cc1nn2c(=O)cc(-c3ccc(Cl)cc3)[nH]c2c1-c1ccccc1] | 9080334 | 5-(4-chlorophenyl)-2-methyl-3-phenylpyrazolo[1,5-a]pyrimidin-7(4H)-one | 41% | B6 |
| 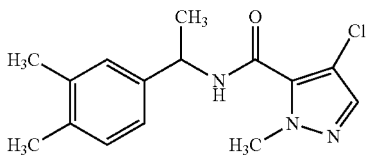 [SMILES: Cc1ccc(C(C)NC(=O)c2c(Cl)cnn2C)cc1C] | 9043411 | 4-chloro-N-[1-(3,4-dimethylphenyl)ethyl]-1-methyl-1H-pyrazole-5-carboxamide | 37% | C1 |
| 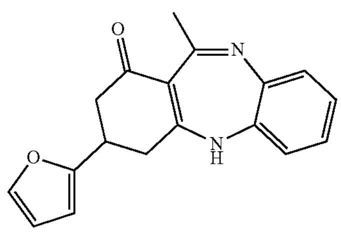 [SMILES: CC1=Nc2ccccc2NC2=C1C(=O)CC(c1ccco1)C2] | 9025733 | 3-(2-furyl)-11-methyl-2,3,4,5-tetrahydro-1H-dibenzo[b,e][1,4]diazepin-1-one | 84% | n/a |

Figure 23:
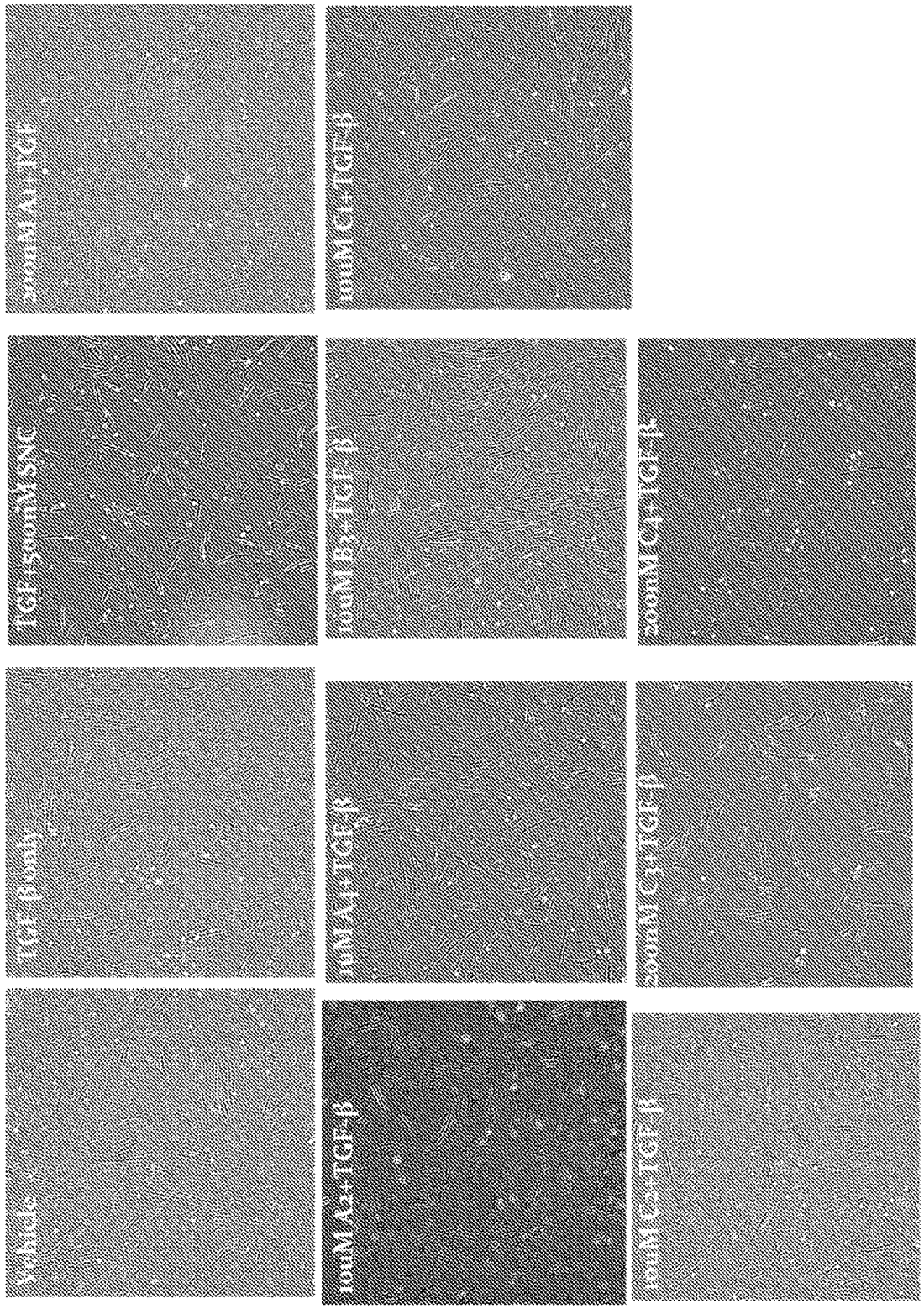
FIG. 23 is a panel of cell images showing efficacy of selected Chembridge hits in myofibroblast formation assays using human lung fibroblasts. These cell images show the powerful effect of these small molecules in preventing TGFβ induced myofibroblast formation while not causing cell death. Key: SNC: salinomycin control; A1: 5255687; A2:5130037; A4:9040737; B3:9057423; C2:9018748; C3:9048694; C4:9022265.

Selected Chembridge hits were tested in myofibroblast formation assays using human orbital fibroblasts (FIG. 22) and human lung fibroblasts (FIG. 23). These cell images show the powerful effect of these small molecules in preventing TGFβ induced myofibroblast formation while not causing cell death.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of treating fibrosis in a patient in need thereof comprising:
    administering to the patient an amount of a polyether antibiotic that is therapeutically effective to inhibit myofibroblast formation and thereby treat the fibrosis.

2. The method of claim 1, wherein the polyether antibiotic is selected from the group consisting of monensin, lasalocid, salinomycin, narasin, maduramycin, semduramycin, laidlomycin lonomycin, ionomycin, nigericin, grisorixin, dianemycin, lenoremycin, antibiotic X206, alborixin, septamycin, antibiotic A204, Compound 47,224, mutalomycin, isolasalocid A, lysocellin, tetronasin, etheromycin, antibiotic X-14766A, antibiotic A-23187, antibiotic A-32887, Compound 51,532, and K41.

3. The method of claim 1, wherein the fibrosis is liver fibrosis, heart fibrosis, pulmonary fibrosis, or kidney fibrosis.

4. The method of claim 1, wherein the fibrosis is scarring of eye tissue.

5. The method of claim 1, wherein the fibrosis is present in reconstructed breast tissue in a post-irradiated patient.

6. The method of claim 1, wherein said administering is carried out orally, parenterally, periadventitially, subcutaneously, intravenously, intramuscularly, intraperitoneally, by inhalation, by intranasal instillation, by implantation, by intracavitary or intravesical instillation, intraocularly, intraarterially, intralesionally, transdermally, or by application to mucous membranes.

7. The method of claim 1 further comprising repeating said administering.

8. The method of claim 1, further comprising:
    administering to the patient an amount of a second agent that is therapeutically effective to treat the fibrosis, wherein the second agent is different from the polyether antibiotic.

9. The method of claim 8, wherein the second agent is selected from the group consisting of calcium channel blockers, cytotoxic agents, cytokines, chemokines, integrins, growth factors, hormones, lysophosphatidic acid (LPA) receptor 1 antagonists, agents that modulate the TGF-β pathway, endothelin receptor antagonists, agents that reduce connective tissue growth factor (CTGF) activity, matrix metalloproteinase (MMP) inhibitors, agents that reduce the activity of platelet-derived growth factor (PDGF), agents that interfere with integrin function, agents that interfere with the pro-fibrotic activities of cytokines, agents that reduce oxidative stress, PDE4 inhibitors, PDE5 inhibitors, mTor inhibitors, modifiers of the arachidonic acid pathway, peroxisome proliferator-activated receptor (PPAR)-γ agonists, kinase inhibitors, inhibitors of VEGF signaling pathway, matrix metalloproteinases, tissue inhibitors of metalloproteinases (TIMPs), HGF agonists, angiotensin-converting enzyme (ACE) inhibitors, angiotensin receptor antagonists, inhibitors of advanced glycation endproducts (AGEs) or their receptors (RAGEs), Rho kinase inhibitors, PKC inhibitors, ADAM-10 inhibitor, farnesoid X receptor agonists, caspase inhibitors, anti-oxidants, inhibitors of collagen expression, LMW heparin or heparin analogs, copper chelators, TNF-α blocking agents, HMG-CoA reductase inhibitors, and Thy-1 (CD90) inhibitors.

10. The method of claim 1, wherein the fibrosis is not secondary to microbial infection.

* * * * *

UNITED STATES PATENT AND TRADEMARK OFFICE
CERTIFICATE OF CORRECTION

| | |
|---|---|
| PATENT NO. | : 10,548,911 B2 |
| APPLICATION NO. | : 15/319254 |
| DATED | : February 4, 2020 |
| INVENTOR(S) | : Phipps et al. |

Page 1 of 1

It is certified that error appears in the above-identified patent and that said Letters Patent is hereby corrected as shown below:

On the Title Page

Under (60) Related U.S. Application Data, second line, delete "No. 62/201,602" and insert --No. 62/012,602--.

In the Claims

In Claim 2, Column 85, Lines 30-31, insert --,-- after "laidlomycin".

Signed and Sealed this
Twelfth Day of May, 2020

Andrei Iancu
*Director of the United States Patent and Trademark Office*